(12) United States Patent
Wu

(10) Patent No.: US 10,835,608 B2
(45) Date of Patent: Nov. 17, 2020

(54) POLYMER-CARBOHYDRATE CONJUGATES FOR DRUG DELIVERY TECHNOLOGY

(71) Applicant: Nian Wu, North Brunswick, NJ (US)

(72) Inventor: Nian Wu, North Brunswick, NJ (US)

( * ) Notice: Subject to any disclaimer, the term of this patent is extended or adjusted under 35 U.S.C. 154(b) by 55 days.

(21) Appl. No.: 14/561,219

(22) Filed: Dec. 5, 2014

(65) Prior Publication Data

US 2015/0157721 A1     Jun. 11, 2015

Related U.S. Application Data

(60) Provisional application No. 61/912,228, filed on Dec. 5, 2013.

(51) Int. Cl.

| | |
|---|---|
| *A61K 47/26* | (2006.01) |
| *A61K 31/337* | (2006.01) |
| *C08L 71/02* | (2006.01) |
| *A61K 9/08* | (2006.01) |
| *A61K 9/00* | (2006.01) |
| *A61K 31/05* | (2006.01) |
| *A61K 31/506* | (2006.01) |
| *A61K 47/28* | (2006.01) |

(52) U.S. Cl.
CPC ............ *A61K 47/26* (2013.01); *A61K 9/0014* (2013.01); *A61K 9/0019* (2013.01); *A61K 9/0048* (2013.01); *A61K 9/0095* (2013.01); *A61K 9/08* (2013.01); *A61K 31/05* (2013.01); *A61K 31/337* (2013.01); *A61K 31/506* (2013.01); *C08L 71/02* (2013.01); *A61K 47/28* (2013.01); *C08G 2650/26* (2013.01); *C08L 2203/02* (2013.01)

(58) Field of Classification Search
None
See application file for complete search history.

(56) References Cited

U.S. PATENT DOCUMENTS

| | | | | |
|---|---|---|---|---|
| 2012/0202890 A1* | 8/2012 | Wu | ...................... | A61K 31/575 514/731 |
| 2012/0202979 A1* | 8/2012 | Wu | ...................... | A61K 31/231 536/17.4 |

FOREIGN PATENT DOCUMENTS

WO    WO2010/141069    * 12/2010

OTHER PUBLICATIONS

"Analogue", Merriam-Webster OnLine Dictionary, also available at http://www.merriam-webster.com/dictionary/analogue; last viewed May 6, 2010.*
Goodman & Gillman, The Pharmacological Basis of Therapeutics, 9$^{th}$ edition, 1996, pp. 51, 57 and 58.*

* cited by examiner

*Primary Examiner* — Bahar Craigo

(57) ABSTRACT

The invention comprises compounds, methods of making, and methods of using. The compounds may have a linear or cylic backbone and three or four appended functional groups: one or two lipohilic compounds including sterols or "fat soluble" vitamins, one or two hydrophilic polymer, and one or two carbohydrate. A group of polymer-carbohydrate conjugates having a central backbone and three appended functional groups are disclosed wherein one lipophilic compound is void of both steroid acids. The conjugate may have fatty acids as the primary lipophilic carrier, one hydrophilic polymer, and one carbohydrate. Specific functional groups may be selected for specific applications in formulating pharmaceuticals, cosmetics, nutriceuticals, and the like. Typical coupling reaction of the conjugates may involve one or more or combinations or in series of alkylation including N-alkylation or O-alkylation, etherification, esterification and amidation chemical processes. A variety of linkers between the backbone and functional groups may also be selected to modify the carriers or center backbones for the coupling reactions and optimize performance of the conjugates.

3 Claims, 1 Drawing Sheet

POLYMER-CARBOHYDRATE CONJUGATES FOR DRUG DELIVERY TECHNOLOGY

This application claims priority to the provisional patent application Ser. No. 61/912,228, entitled "Polymer-Carbohydrate Conjugates for Drug Delivery Technology" filed in the U.S. Patent and Trademark Office on Dec. 5, 2013, by Nian Wu.

FIELD OF THE INVENTION

The present invention relates to polymer-carbohydrate conjugates, detailed and specific disclosures are given for synthetic polyethyleneglycol (PEG)-carbohydrate conjugates with sterols or so called "fat solable" vitamins ("lipovitamin") as the lipophilic carriers excluding both steroid acids and fatty acids as the primary lipophilic component in the conjugates and preferably having substantially monodisperse PEG chains if used for intravenous drug administration. More particularly, the present invention relates to novel polymer-carbohydrate conjugates having sterols or steroid alcohols or lipophilic vitamin component to increase lipophilic characters in the hydrophobic portion or polymer-carbohydrate conjugates and their use for drug delivery, cosmetics and other purposes.

BACKGROUND OF INVENTION

Polyethyleneglycol (PEG) is widely used as a water soluble carrier for polymer-drug conjugates. PEG is undoubtedly the most studied and applied synthetic polymer in the biomedical field [Duncan, R. *Nature Rev. Drug Discov.* 2003, 2, 347-360]. As an uncharged, water-soluble, nontoxic, nonimmunogenic polymer, PEG is an ideal material for biomedical applications. Covalent attachment of PEG to biologically active compounds is often useful as a technique for alteration and control of biodistribution and pharmacokinetics, minimizing toxicity of these compounds [Duncan, R. and Kopecek, J., *Adv. Polym. Sci.* 57 (1984), 53-101]. PEG possesses several beneficial properties: very low toxicity [Pang, S. N. J., *J. Am. Coil. Toxicol,* 12 (1993), 429-456], excellent solubility in aqueous solutions [Powell, G. M., *Handbook of Water Soluble Gums and Resins*, R. L. Davidson (Ed.), Ch. 18 (1980), MGraw-Hill, New York], and extremely low immunogenicity and antigenicity [Dreborg, S, *Crit. Rev. Ther. Drug Carrier Syst.,* 6 (1990), 315-365]. The polymer is known to be non-biodegradable, yet it is readily excretable after administration into living organisms. In vitro study showed that its presence in aqueous solutions has shown no deleterious effect on protein conformation or activities of enzymes. PEG also exhibits excellent pharmacokinetic and biodistribution behavior. [Yamaoka, T., Tabata, Y. and Ikada, Y., *J. Pharm. Sci.* 83 (1994), 601-606].

Over last three decades, some of promising drug carriers that have been investigated in systemic delivery systems includes liposomes, polymeric nanoparticles, polymeric micelles, ceramic nanoparticles and dendrimers (Cherian et al. *Drug. Dev. Ind. Pharm,* 26: (2000) 459-463; Lian and Ho. *J. Pharm. Sci,* 90 (2001) 66T-680; Adams et al. *Pharm. Sci,* 92 (2003) 1343-1355; Na et al. *Eur. J. Med. Chem.* 41 (2006) 670-674; Kaur et al. *J. Control. Rel,* 127 (2008) 97-109). Systemic drug delivery may be achieved by intravenous or intraperipheral injection and therefore is noninvasive. The drugs may be administered repeatedly as needed. However, in order to achieve therapeutic concentrations at the target site, systemic administration requires large dosages with relatively high vehicle contents which may cause side effects such as allergic reactions ["Cremophor-based paclitaxel 'chemo' drug triggers fatal allergic reactions," *The Medical News.* 9 Jun. 2009].

In the design of safe and biocompatible delivery systems, several important factors may be taken into account including high solubilization properties and retaining power of the carrier and appropriate surface characteristics to permit interactions with potential targeting tissue sites or cell membrane permeations.

The important role of sugars in many specific interactions in living systems is well recognized. Large molecular weight carriers such as proteins or liposomes may be modified with sugars for specific drug delivery (Monsigny M, Roche A C, Midoux P and Mayer R., *Adv Drug Delivery Rev.,* 14 (1994):1-24; Palomino E. *Adv Drug Delivery Rev.,* 13 (1994) 311-323]. Lipid-sugar particles have been used for drug delivery to the brain for providing prolonged duration local anesthesia when injected at the sciatic nerve in rats [Kohane D S, Lipp M, Kinney R., Lotan N, Langer R., *Pharm. Res.* 17 (2000) 1243-1249]. Since sugar-lipids are composed of materials that occur naturally in the human body suggests potential advantages over some other polymer-based controlled-release terms of biocompatibility [Kohane D S, Lipp M, Kinney R, Anthony D, Lotan N, Langer R., *J. Biomed. Mat. Res.* 59 (2002) 450-459; Menei P, Daniel V, Montero-Menei C, Brouillard M, Pouplard-Barthelaix A, Benoit J P., *Biomaterials,* 14 (1993) 470-478]. Lipid-sugars have a good biocompatibility as shown by the results of the in vitro and in vivo studies [Kohane D S, Lipp M, Kinney R, Anthony D, Lotan N, Langer R., *J. Biomed. Mat. Res.* 59 (2002) 450-459].

Sterol is classified as a lipid in one of the eight lipid categories [Fahy E, Subramaniam S, Brown H A, et al. (2005). "A comprehensive classification system for lipids". *J. Lipid Res.* 46 (5): 839-61]. The lipid classification scheme is chemically based and driven by the distinct hydrophobic and hydrophilic elements that compose the lipid. Sterols and related compounds play essential roles in the physiology of eukaryotic organisms are a subgroup of the steroids. They occur naturally in plants, animals, and fungi, the most familiar type of animal sterol is cholesterol. Cholesterol is vital to animal cell membrane structure and function and forms part of the cellular membrane in animals, where it affects the cell membrane's fluidity and serves as secondary messenger in developmental signaling [Alberts B, Johnson A, Lewis J, Raff M, Roberts K, and Walter P (2002). *Molecular biology of the cell.* 4$^{th}$ Edition, New York: Garland Science. p. 1874]. For the distinction and clarity, sterols or steroid alcohols ultilized in the present invention, as showed in General Formula 1, are not water soluble and different chemical compounds from those of steroid acids such as cholic acid or other bile acids.

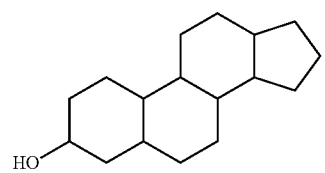

General Formula 1: Basic Structure of Sterols in the Invention

The present invention compromises one of the three carrier groups consisting of a sterol or sterol-like or "fat soluble" vitamin component including but not limited to cholesterol, stigmasterol, ergosterol, hopanoids, phytosterol, sitosterol, campesterol, brassicasterol, avenasterol adosterol, and stanols (saturated steroid alcohols or hydrogenated sterols). Sterols are biological importance as a highly compatible vehicle for drug delivery, for instance cholesterol makes up about 10-50 percent of the total lipid in natural cell membranes, the conjugates containing sterols or fat soluble vitamins may increase the drug permeation for cell targeted delivering.

The human body has a natural tendency to maintain homeostasis, and may be elaborated from substances present in the diet, sometimes exclusively, for vitamins, minerals, essential amino-acids and essential fatty acids including polyunsaturated fatty acids which play a significant role in the prevention of cardiovascular disease in human. Vitamin E is the general term for all tocopherols and tocotrienols, of which alpha-tocopherol is the natural and biologically most active form. The antioxidant function of vitamin E is considered to be critical for the prevention of oxidation of tissue. While these molecules are essential for the human body, they may be ultilized as safer ingredients to design for an ideal carbohydrate-lipid conjugate.

The present invention compromises one of the three carrier groups consisting of a sterol or fat soluble vitamin. Another carrier group is a carbohydrate molecule or water soluble vitamin such as ascorbic acid or thiamine or biotin. The third carrier is a water soluble polymer such as polyethylene glycol. The three carrier groups are attached covalently to a central backbone where at least three bonding positions or sites available. The conjugation may be achieved via one or more types of reactions or combination of alkylation including N-alkylation or O-alkylation, etherification, esterification and amidation.

The solubility of organic molecules is often summarized by the phrase, "like dissolves like." This means that molecules with many polar groups are more soluble in polar solvents, and molecules with few or no polar groups (i.e., nonpolar molecules) are more soluble in nonpolar solvents (R. Casiday and R. Frey, "Maintaining the Body's Chemistry: Dialysis in the Kidneys," http://www.chemistry.wustl.edu/~edudev/LabTutorials/Dialysis/Kidneys.html, Department of Chemistry, Washington University, St. Louis, Mo., accessed on Dec. 3, 2013).

Vitamins are either water-soluble or fat-soluble (soluble in lipids and nonpolar compounds), depending on their molecular structures. Water-soluble vitamins have many polar groups and are hence soluble in polar solvents such as water. In contrast fat-soluble vitamins are predominantly nonpolar and hence are soluble in nonpolar solvents such as the fatty (nonpolar) tissue of the body. Solubility is a complex phenomenon that depends on the change in free energy ($\Delta G$) of the process. For a process, i.e., a vitamin dissolving in a solvent, to be spontaneous, the change in free energy may be negative (i.e., $\Delta G<0$) [M. Traverso, "Vitamin Solubility," http://www.chemistry.wustl.edu/~edudev/LabTutorials/CourseTutorials/Tutorials/Vitamins/molecularbasis.htm, Washington University, St. Louis, Mo., accessed on Dec. 3, 2013].

Unlike steroid acids, a sterol-like chemical structures have negligible solubility in water, but soluble in nonpolar solvents such as hexane. Sterols containing a double bond are slightly more polar than those of stanols for two reasons: the pi bond electrons are more polarizable, thus contributing to instantaneous dipole moments, and the vinylic bond tends to be slightly polar, contributing to the permanent dipole moment. In a symmetrical trans disubstituted double bonds, the sum of the dipole moments is zero. In the analogous cis double bonds, the vector sum of the two dipoles is directed perpendicular to the double bond. This results in a non-zero molecular dipole. The permanent dipole results in an increased boiling temperature and lower melting points. Lipophilic vitamins have a general structure of conjugated double bonds which increase non-polar interactions with hydrophobic molecules.

Narrow molecular weight distribution of drug delivery polymers is crucially important for biomedical applications, especially if used for intravenous injections. For instance, PEG-8 Caprylic/Capric Glycerides are mixtures of monoesters, diesters, and triesters of glycerol and monoesters and diesters of polyethylene glycols with a mean relative molecular weight between 200 and 400. Partially due to allergic reactions observed in animals, the application of PEG-8 CCG for parenteral administration of many water-insoluble drugs is restricted and hence is limited usable for human drug formulations.

BRIEF SUMMARY OF THE INVENTION

The present invention comprises compounds having a Backbone and three or four appended functional groups as showed in FIG. 1: one or two lipophilic vitamins or sterols or alike, one or two hydrophilic polymers, one or two carbohydrates which may be substituted by a water soluble vitamin. Specific functional groups may be selected for specific applications in formulating pharmaceuticals, cosmetics, nutriceuticals, and the like. A variety of linkers between the backbone and functional groups may also be selected to optimize performance. The coupling reaction is one or combination or series of alkylation, esterification, etherification and amidation chemical process.

DETAILED DESCRIPTION OF PREFERRED EMBODIMENTS

Embodiments of the present invention are described herein in the context of varying polymer-carbohydrate conjugates for drug delivery. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementation of the present invention.

In the interest of clarity, not all of the routine features of the implementations herein are described. It will be appreciated that in the development of such actual implementation, numerous implementation-specific details may need to be made in order to achieve the developer's specific goals, and that these specific goals may vary.

United States Patent Publications 2012/202,979 and 2012/202,890, which are hereby incorporated by reference, teach the aqueous formulations of poor water soluble agents by employing certain polymer-carbohydrate-lipid (PCL) conjugates. The patents described how to prepare the polymer-carbohydrate-lipid conjugates and its applications by simply adding the conjugate to an aqueous solution. It has been demonstrated that PCLs are useful for solubilizing hydrophobic drugs without the formation of liposomes or microemulsions.

Differentiating from the previous inventions published in US2012/202,979 and US2012/202,890, the present invention comprises the lipophilic portion of the polymer-carbohydrate conjugates excluding steroid acids or fatty acids while those conjugates remains a basic structure having a backbone and three or four appended functional groups: one or two lipophilic vitamins or sterols, one or two hydrophilic polymers, and one or two carbohydrates which may be substituted by a water soluble vitamin. By combining these functionalities all into one compound, it is possible to achieve improved formulations of many active agents. The general structure of the family of compounds is shown as FIG. 1 or the three-dimensional Chemical Structure 1, where Backbone or B indicates the backbone, P indicates the polymer, H indicates lipophilic vitamin or sterol or alike, and S or Sugar indicates the carbohydrate. In aqueous solutions, the new conjugates act as a solubility enhancer of poor water soluble agents resulting in either a true solution or a very stable emulsified suspension with those of active agents. In certain cases, the carbohydrate may be substituted by a water soluble vitamin such as ascorbic acid, which is also classified as aldonic acids, the sugar acid.

Figure 1:
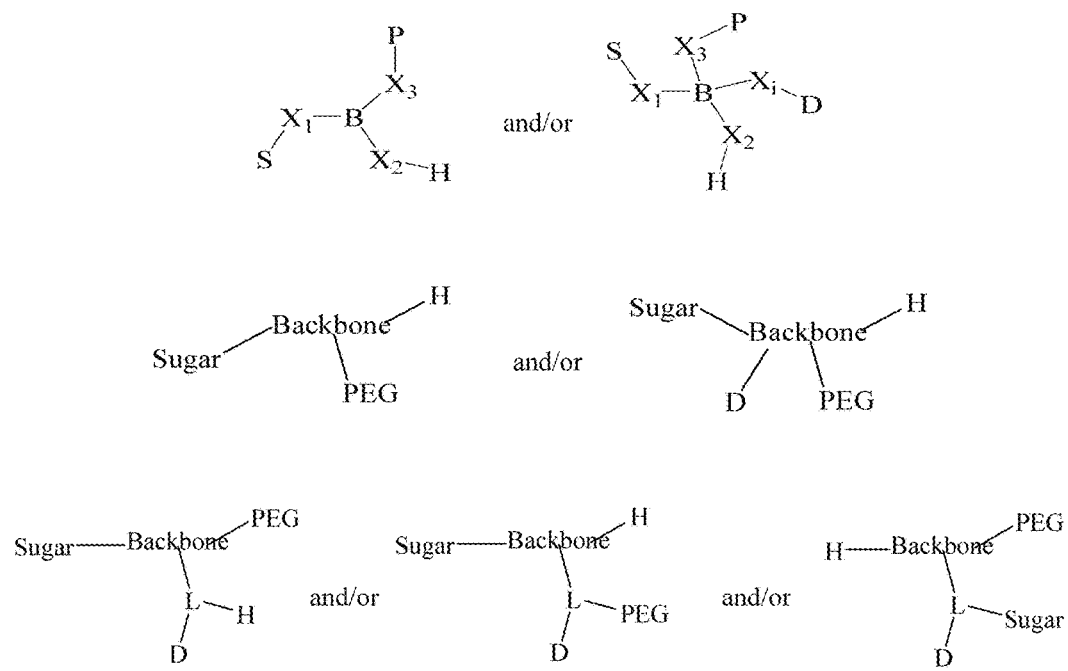
FIG. 1 shows a representation of the conjugates of the present invention.

In another aspect, the invention comprises compounds having a backbone and three or appended functional groups with four carriers: one or two sterols, one or two hydrophilic polymers, and one or two carbohydrates which may be substituted by a water soluble vitamin. By doubling one of these three functionalities all into one compound, it may be possible to achieve more enhanced formulations of many poor water soluble or poor permeable active agents. The general structure of the family of compounds is also shown in FIG. 1, where B indicates the backbone, P indicates the polymer, H indicates the lipophilic vitamin or sterol or alike, S indicates the carbohydrate, and D as duplicates one of the three carriers or a water soluble vitamin. The conjugate with four carriers is as showed in Chemical Structure 2, in the three-dimensional drawing where ascorbic acid (as D) is bonded to the central backbone

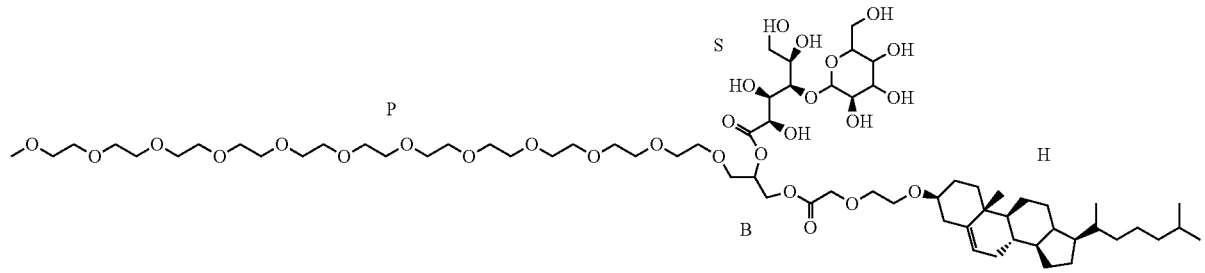

In another aspect, the invention comprises compounds having a backbone and three or four carrier groups Chemical Structure 2

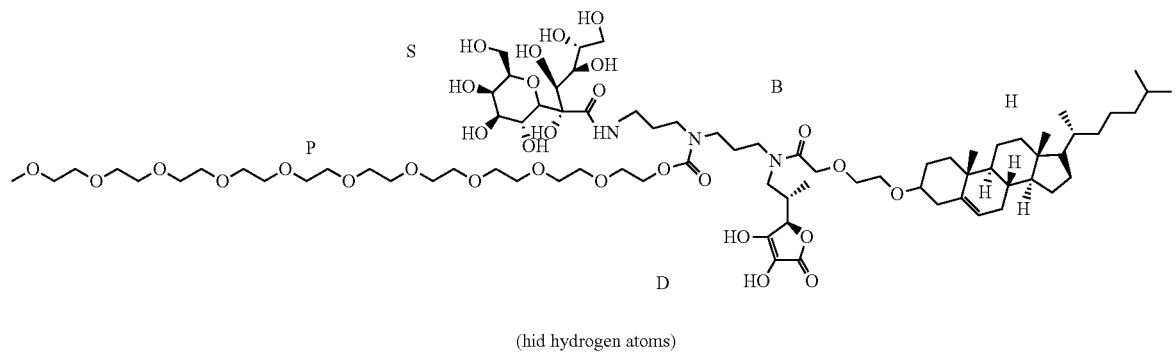

(hid hydrogen atoms)

Another differentiation from our previous inventions published in US2012/202,979 and US2012/202,890, the present invention comprises sterols or sterol-like compounds to significantly reduce potential hemolytic activity induced by fatty acids [Mimura, T. "Fatty acids and sterols of the tunicate, *Salpa thompsoni*, from the Antarctic Ocean: chemical composition and hemolytic activity". *Chemical & pharmaceutical bulletin*, 34 (1986) 4562]. Combination of sterols and fatty acids may also reduce the hemolytic effects of fatty acids alone, thus it may be possible to include a fatty acid as the fourth carrier group when necessary. Unlike sterols, water soluble steroid acids (bile acids) are more likely inducing hemolytic anemia [Ilani, A. "The pH dependence of the hemolytic potency of bile salts". *Biochimica et biophysica acta*, 1027 (1990) 199]. For this particular reason, no steroid acid or fatty acids will be selected as the primary lipophilic carrier in the current invention. In case there are two lipophilic carriers, one may be cholesterol or a non-hemolytic sterol or "fat soluble" vitamin.

In one aspect of the present invention, the present invention comprises nonfatty acid and nonsteroid acid lipophilic component including sterols or sterol-like compounds to significantly reduce potential hemolytic activity as compared to commercial available PEG-lipids including polyethylene glycol sorbites, polyoxyethylated castor oil (Cremophor) and mono/diglycerides of caprylic/capric acid in glycerol (Capmul®) polyglycolized glycerides (Labrafac®), PEG-6 glyceryl monoleate or PEG-6 glyceryl linoleate (Labrafil®), PEG-8 glyceryl caprylate/caprate (Labrasol®). While these fatty acid based lipid-polymers may increase poor water soluble agents, hemolysis is induced at higher lipid-drug ratios [G. D. Noudeh, P. Khazaeli and P. Rahmani. "Study of the Effects of Polyethylene Glycol Sorbitan Esters Surfactants Group on Biological Membranes." *International Journal of Pharmacology*, 4 (2008) 27-33; A. O. Nornooa, D. W. Osborneb, D. S. L. Chow "Cremophor-free intravenous microemulsions for paclitaxel: I: Formulation, cytotoxicity and hemolysis." *International Journal of Pharmaceutics*. 349 (2008) 108-116].

Further differentiation from our previous inventions published in US2012/202,979 and US2012/202,890, the present invention comprises sterols or tocopherol carriers which are a rigid component in the conjugate construction, not having the same freedom of movement that the fatty acid tails of the conjugates possess. Adjacent carrier groups, i.e., polymers may be partially restricted in their freedom of movement throughout the length of their polymer chains that are abutting, e.g., the sterol molecules. However, since the sterol or tocopherol components have certain effect of creating spaces in the uniform hydrophobic morphology of the bilayer, the portion of the polymer chains below the abutted regions are increased in their freedom of movement. There is a neglect steric hindrance for carrier groups apart from the cyclic ring portion.

Another differentiation from our previous inventions published in US2012/202,979 and US2012/202,890, the present invention comprises sterols or "fat soluble" vitamin carriers are more lipophilic. Based on the same center backbone, polymer, carbohydrate, and the linker between the center backbone and the lipophilic group, the oil/water phase partition (LogP) or distribution coefficients (Log D) are largely difference between the sterols or "fat soluble" vitamins utilized in present invention and those of steroid acids or fatty acids used in previous inventions as indicated in the Tale 1, where the Log Ps and Log Ds were calculated with a computer program of Marvin Sketch (ChemAxon Kft, Budapest, Hungary). A positive value indicates more oil soluble and a negative value indicates more water soluble. Thus the water solubility or lipophilicity is solely based on the inherited character of the hydrocarbon carrier groups, which showed a magnitude difference between PEG-carbohydrate-sterol conjugates and PEG-carbohydrate-steroid acid conjugates or between sterols and steroic acids. The further chemistry difference between steroid acids and sterols is that sterols contain only have a single hydroxyl group and steroid acids contain a carbolytic and multiple hydroxyl groups which are more water soluble or hemolytic. While the difference in the LogP values is smaller between fatty acids and sterols, they are different molecules in the chemical structures and hemolytic sensitivity.

Table 1. Solubility comparison between different type carrier groups based on an identical structural design:

TABLE 1

Solubility comparision between different type carrier groups based on an identical structural design: PEG-carbohydrate structural base

| | Carrier Group (R) | Log P | pH | Log D |
|---|---|---|---|---|
| 1 | Cholesterol | 7.11 | 1.50 | 7.11 |
| | | | 7.40 | 7.11 |
| | PEG$_{11}$-Carbohydrate-Cholesterol (R) | 0.29 | 1.50 | -3.21 |
| | | | 5.00 | -3.09 |
| | | | 6.50 | -2.18 |
| | | | 7.40 | -1.33 |
| 2 | Cholic Acid | 2.48 | 1.50 | 2.48 |
| | | | 5.00 | 1.84 |
| | | | 6.50 | 0.47 |
| | | | 7.40 | -0.35 |
| | PEG$_{11}$-Carbohydrate-Cholate (R) | -4.98 | 1.50 | -5.36 |
| | | | 7.40 | -5.36 |
| 3 | Oleic Acid | 6.78 | 1.50 | 6.78 |
| | | | 5.00 | 6.48 |
| | | | 6.50 | 5.26 |
| | | | 7.40 | 4.40 |
| | PEG$_{11}$-Carbohydrate-Oleate (R) | -1.06 | 1.50 | -1.06 |
| | | | 7.40 | -1.06 |
| 4 | α-Tocopherol | 8.94 | 1.50 | 8.94 |
| | | | 7.40 | 8.94 |
| 5 | PEG$_{11}$-Carbohydrate-Tocopherol (R) | 2.12 | 1.50 | -1.39 |
| | | | 5.00 | -1.27 |
| | | | 6.50 | -0.35 |
| | | | 7.40 | 0.50 |
| 6 | Cholecalciferol | 7.13 | 1.50 | 7.12 |
| | | | 7.40 | 7.13 |

TABLE 1-continued

Solubility comparision between different type carrier groups based on an identical structural design: PEG-carbohydrate structural base

| | Carrier Group (R) | Log P | pH | Log D |
|---|---|---|---|---|
| | PEG$_{11}$-Carbohydrate-Cholecalciferol (R) | 0.54 | 1.50 | −2.96 |
| | | | 5.00 | −2.84 |
| | | | 6.50 | −1.93 |
| | | | 7.40 | −1.08 |
| | Retinoic acid | 5.01 | 1.50 | 5.01 |
| | | | 5.00 | 4.71 |
| | | | 6.50 | 3.50 |
| | | | 7.40 | 2.64 |
| 7 | PEG$_{11}$-Carbohydrate-Retinoate (R) | −2.83 | 1.50 | −2.83 |
| | | | 7.40 | −2.83 |

As showed in Table 1, while the oil/water phase partition (LogP) coefficient of the sterol is significantly different from the steroid acids from same structural configuration of a conjugate, the LogP may be altered with longer polyethylene glycol chains. However an extensive PEG chain is required for a sterol based PEG-carbohydrate conjugate to match those LogP vales of steroid acid based conjugates. For example, a LogP of −4.79 is calculated for a PEG-carbohydrate-cholesterol with a PEG chain of approximate 107 subunits, in comparison, a LopP of −4.98 is obtained for a PEG-carbohydrate-cholate with a PEG chain approximately 10 times shorter, only 11 subunits. This demonstrates the significant differences in chemical and physical properties between sterols and steroid acids.

In one aspect of the present invention, the hydrophobic interaction may be increased significantly by incorporating a cyclic lipophilic group such as sterols into the polymer-carbohydrate conjugates. The water solubility is enhanced for those hydrophobes where the encapsulation of the lipophilic molecules into the sterol-polymer conjugates is improved. Differentiated from previous described fatty acid-carbohydrate-polymer conjugates, the current invention presents a sterol-like cyclic structural carrier having stronger hydrophobic interactions with lipophilic solutes. The same hydrophobic interaction may not be achieved with steroid acids due to large interferences from the hydroxyl groups of steroid acids. As showed in the General Formula 1, sterol such as cholesterol does not have any free hydroxyl group after bonding to the central backbone.

In one aspect of the present invention comprises sterol or sterol-like molecules with single hydroxy group available for the conjugation to reduce potential interferences caused by free hydroxyl(s) to hydrophobic interactions between the lipophilic carriers and hydrophobic solutes.

In watery-aqueous environment, the interior of polymer-carbohydrates is largely non-polar and the principle to use when determining hydrocarbon solubility is "like dissolves like." Most poor water soluble compounds contain at least one cyclic ring such as phenyl groups; thus the hydrophobic steroyl or tocopheryl head of a conjugate and lipophilic solute are clumped together "like dissolves like." On the outside of the polymer-carbohydrates are largely polar groups which are able to interact with the polar water molecule, thus the entire polymer-carbohydrate incorporating lipophilic solutes is then water soluble.

In the novel polymer-carbohydrate conjugates, the central backbones have two sites with polar groups attached and another site with nonpolar groups are good solubility enhancers. They may aid in the formation of stable solution or emulsions or blends of water and lipophilic agents. These polymer conjugates reduce the interfacial tension between hydrophobic molecules and water by adsorbing the energy at the liquid-liquid interface.

In one aspect of the present invention, sterols or tocopherols or alike with double bonds are the preferable component of the polymer-carbohydrate conjugates. When two molecules come together, the variations in charge may create a situation where one end of a molecule might be slightly negative and the other end of that molecule could be slightly positive. This would add more attraction of the two molecules. As chemical properties are considered, ring structured and linear compounds differ greatly. The ring structures with double bonds may be considered as a "molecular handle" with increased intermolecular forces that hold molecules together in a liquid or solution phase. The amount of difference in intermolecular forces between a cyclic compound and a linear molecule is based on the polarizability of a particular molecule.

The hydrophobic interaction is defined as an entropic effect generating from the disruption of highly dynamic hydrogen bonds between molecules of liquid water by the hydrophobic solute [T. P. Silverstein, "The Real Reason Why Oil and Water Don't Mix". *Journal of Chemical Education*. 75 (1998) 116-346]. When a hydrophobic solute is mixed in an aqueous medium, hydrogen bonds between water molecules will be broken to make room for the hydrophobic solute; since water molecules do not react with the hydrophobic solute. Such hydrophobic effect may be quantified by measuring the partition coefficients of non-polar molecules between water and non-polar solvents. The partition coefficients may be transformed to free energy ($\Delta G$) of transfer which includes enthalpic ($\Delta H$) and entropic ($\Delta S$) components. The hydrophobic effect has been found to be entropy ($\Delta S$)-driven at room temperature because of the reduced mobility of water molecules in solvation shell of the non-polar solute. The change in enthalpy ($\Delta H$) of the system may be zero, negative or positive because the formation of the new hydrogen bonds may partially, completely, or over compensate for the hydrogen bonds broken by the entrance of the hydrophobic solute. The change in enthalpy, however, may be insignificant in determining the spontaneity of mixing hydrophobic molecules and water because the change in entropy ($\Delta S$) is very large. According to the Gibbs free energy Equation, $\Delta G = \Delta H - T \Delta S$, with a small unknown value of $\Delta H$ and a large negative value of $\Delta S$, the value of $\Delta G$ will turn out to be positive. A positive $\Delta G$ indicates that the mixing of the hydrophobe and water molecules is not spontaneous which results in a phase separation or precipitation.

In another aspect of the current invention, the hydrophilic-lipophilic interaction is well balanced with the polymer-carbohydrate-sterol conjugates [Griffin W C. "Calculation of HLB Values of Non-Ionic Surfactants," *Journal of the Society of Cosmetic Chemists*. 5 (1954) 259]. For example, hydrophilic-lipophilic balance number remains greater than 12 due to the large polymer portion in the conjugates to form translucent microemulsions spontaneously. Unlike microemulsions formed by a mixture of surfactants or lipid polymers, co-surfactants and/or co-solvents which a surfactant or lipid polymer concentration is several times higher that significantly exceeds the concentration of the dispersed phase or mechanically produced translucent microemulsions which specialized equipment is required, the polymer-carbohydrate-sterol/lipophilic vitamin conjugates in the present invention are able to form transparent solution or nanoemulsions spontaneously by a single polymer-carbohydrate-sterol or polymer-carbohydrate-tocopherol polymer-carbohydrate-retinol and typically without co-solvent and external high energy required [Mason T G, Wilking J N, Meleson K, Chang C B, Graves S M. "Nanoemulsions: formation, structure, and physical properties", *Journal of Physics: Condensed Matter*, 18 (2006) R635-R666].

In one aspect of the current invention, a stable aqueous solution or emulsion may be formed with minimal amounts of the polymer-carbohydrate conjugates, this is superior over convertional surfactants or other lipid-polymers since many undesirable side effects caused by surfactants or lipid-polymers, higher concentrations of surfactants are disadvantageous or prohibitive in many applications. In addition, the stability of a microemulsion or mechanically formed nanoemulsion is often easily compromised by dilution, by heating, or by changing pH levels.

Though it is possible to use a variety of hydrophilic polymers in practicing the invention, polyethyleneglycol (PEG) is preferred because of its long history of effectiveness and its status of being generally regarded as safe (GRAS). Incorporating PEG, the General Structure 1 of the new polymer-carbohydrate-sterol conjugate is:

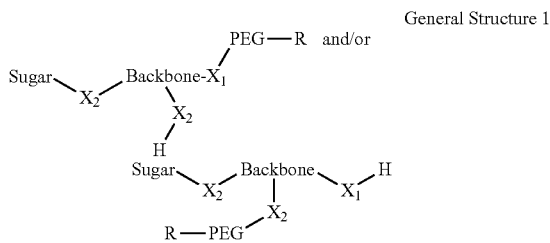

General Structure 1

In General Structure 1, the backbone may be selected from a compound comprises at least three available binding positions or sites for the conjugation of a first carrier, a second carrier and a third carrier, each available binding position or site comprising an expendable amino, hydroxyl, or carboxylic group. The backbone may be selected from the group consisting of glycerol or glycerol-like analogues, polyamines, diamines, triamines, tetraamines, aminodiol, aminotriols, aminoalcohols and amino acids having three available binding positions or sites, triols, tetraols, erythritol, triacids, tetracid, tetraacetic acid, glucoheptonic acid, and tartaric acid, including but not limited to ethanediamine, propanediamine, butanediamine, pentanediamine, hexanediamine, diethylenetriamine, 1,2-diaminoethane, 1,3-diaminopropane (propane-1,3-diamine), 4-amino-3-hydroxybutyric acid, N-(2-hydroxyethyl)ethylenediamine, 4-amino-2-hydroxybutyric acid, 2-hydroxy-4-aminobutylic acid, 1-β-homoserine, 1-threonine, N-β-aminoethyl-glycine, putrescine (butane-1,4-diamine), cadaverine (pentane-1,5-diamine), hexamethylenediamine (hexane-1,6-diamine), 1,2-diaminopropane, diphenylethylenediamine, diaminocyclohexane. diethylenetriamine, bis(3-aminopropyl)amine, triethylenetetramine, tris(2-aminoethyl)amine, spermine, spermidine, norspermidine, bis(3-aminopropyl)-1,3-propanediamine, 1,2-bis(3-aminopropylamino)ethane, N,N'-bis(3-aminopropyl)-1,3-propanediamine, tris(hydroxymethyl)-aminomethane, diaminobenzidine, N-ethyl-N'-(3-dimethylaminopropyl)carbodiimide, mesoerythritol, triazacyclononane, tetraazacyclododecane, threitol, dithiothreitol, trimethylcyclo-hexane-1,3,5-tricarboxylic acid, trimethylbis(hexamethylene)triamine, bis(hexamethylene)-triamine, arginine, oxylyldiamino-propionic acid, 3-amino-1,2-propanediol, 3-bromo-1,2-propanediol, 3-chloro-1,2-propanediol, 3-fluoro-1,2-propanediol, DL-glyceric acid, diaminopropionic acid, glucoheptonic acid and, 1,2,4-butanetriol, 2,2-bis(hydroxymethyl)butyric acid, 1,3-diamino-2-propanol and 2-(3-aminopropylamino)ethanol, and 3-((3-aminopropyl)-amino)propanol; aspartic acid, glutamic acid, asparagine, glutamine, lysine, ornithine, serine, and threonine or benzyl triols or aminohydroxybenzoic acids or benzenetriol, dihydroxybenzoic acid, diaminobenzoic acid, diaminophenol, diaminobenzoic acid, aminohydroxybenzoic acid, aminosalicylic acid, hydroxyanthranilic acid, hydroxyisophthalic acid, aminoisophthalic acid, 4-(hydroxymethyl)cyclopentane-1,3-diol, deoxyfuconojirimycin, deoxynojirimycin, prostaglandins, hydroxylmethylpiperidinol, dihydroxy(hydroxymethyl)aminocyclopentane, diaminophenol, benzenetetracarboxylic acid, benzenetricarboxylic acid, aminobenzenediol, dihydroxybenzoic acid, aminohydroxybenzoic acid, trihydroxyaniline, benzenetriol, dimethoxybenzenediamine, trihydroxyphenol, (diaminophenoxy)benzenediamine and aminobromophenol. The carbohydrate is a sugar including monosaccharides or disaccharides or oligosaccharides or amino sugar or sugar acids. The H is a lipophilic compound or their diesters including but not limited to sterol or sterol-like compound or lipovitamin, $X_1$, $X_2$ and $X_3$ are the same or different linkers of carbon-nitrogen bond, ester or ether or amide between carrier groups and center backbones. Each linker may be as simple as oxygen or nitrogen or other single atom to form an ester or ether or amide bond between the carrier and center backbone. Alternatively, each linker may be single or replicate linkers selected from Table 1 or Table 2. In some cases, the linker may be co-extensive with or a part of the backbone or functional group component used to synthesize the conjugates.

Typical coupling reaction of the conjugates involves with one or more or combination or in series of alkylation including N-alkylation or O-alkylation, etherification, esterification and amidation chemical processes. The general structure is meant to include all racemers or structural isomers of the structure, as they may be functionally equivalent. The PEG chain preferably consists of between about 5 and 45 subunits, and is preferably substantially monodisperse. R is the terminal group on the PEG chain may be selected from a wide variety of chemical moieties. Hydroxy or methoxy is commonly selected as the terminal groups. R preferably has a molecular weight of less than about 650. Commercially available PEG-lipid monoesters may be used to formulate many compounds by directly linking new moieties to the available positions on the central backbone.

In one aspect of the present invention, no drug or peptide or biomolecule will be selected as the center backbone. Unlike prodrugs modified from bioactive agents, one of major applications of the present invention is for drug delivery, therefore the conjugates themselves as a delivery vehicle are chemically stable and preferably having less or no toxic to the body.

The terminal group on the PEG chain may be selected from a wide variety of chemical moieties. Such moieties preferably have a molecular weight of less than 650. Such moieties include —OH, —OCH$_3$, —NH$_2$, —COOH, —OCH$_2$CH$_3$, —OCH$_2$CH$_2$OH, —COCH=CH$_2$, —OCH$_2$CH$_2$NH$_2$, —OSO$_2$CH$_3$, —OCH$_2$C$_6$H$_6$, —OCH$_2$COCH$_2$CH$_2$COONC$_4$H$_4$O$_2$, —CH$_2$CH$_2$=CH$_2$, $C_{10}H_{16}N_2O_3S$ and —OC$_6$H$_6$. The terminal group may be a functional group that facilitates linking therapeutic or targeting agents to the surface of lipid vesicle aggregates. Amino acids, amino alkyl esters, biotins, maleimide, diglycidyl ether, maleinimido propionate, methylcarbamate, tosylhydrazone salts, azide, propargyl-amine, propargyl alcohol, succinimidyl (NHS) esters (e.g., propargyl NHS ester, NHS-biotin, sulfo-NHS-LC-biotin, or NHS carbonate), hydrazide, succinimidyl ester, succinimidyl tartrate, succinimidyl succinate, and toluenesulfonate salt are useful for such linking. Linked therapeutic and targeting agents may include Fab fragments, cell surface binding agents, and the like. Additionally, the terminal group may include functional cell-targeting ligands such as folate, transferrin and molecules such as monoclonal antibodies, ligands for cellular receptors or specific peptide sequences may be attached to the liposomal surface to provide specific binding sites. The terminal group may be neutral or include either negatively or positively charged head-groups such as decanolamine, octadecylolamine, octanolamine, butanolamine, dodecanolamine, hexanolamine, tetradecanolamine, hexadecanolamine, oleylamine, decanoltrimethylaminium, octadecyloltrimethylaminium, octanoltrimethylaminium, butanoltrimethylaminium, dodecanoltrimethylaminium, hexanoltrimethylaminium, tetradecanoltrimethylaminium, hexadecanoltrimethylaminium, oleyltrimethylaminium, for example. Other useful R groups include fatty acids or alkyl groups such as alkoxy moieties, amino acids, and sugars including monosaccharides, disaccharides, trisaccharides and the oligosaccharides containing 1, 2, 3, and 4 or more monosaccharide units respectively. Additionally, targeting moieties such as antibody fragments and vitamins may also be used as R groups. The molecular weight of the R group is preferably less than about 650, and for most applications the R group is preferably easily polarized, in order to increase the binding and interaction with proteins at the targeted sites. However, well balanced ionic R groups are advantageously employed for certain modes of administrations such as topical gels and oral solutions targeting the mouth and throat.

The present invention includes linking chemical groups that may be selected to optimize and improve PEG-carbohydrate-lipophilic group based formulations. Selecting an appropriate linker between lipo-portion or PEG or carbohydrate and backbone may be important for several reasons, as described below.

It is well understood that a drug or compound as a xenobiotic, the normal human body doesn't need it. Ideally, a drug should reach the site of action intact, cure the disease, and leave the body after it completes its mission. However, drug developers often face the dilemma that 70 to 90% of drugs under development have water solubility or permeability problem [Thayer, A M. *Chemical & Engineering News*. 88 (2010) 13-18], so that the drug may not reach its site of action and achieve its therapeutic effect, or too slow, so that it stays in the body for a long time causing side effects. An object of this invention is to develop the polymer-carbohydrate-lipids with unique linkers to help drugs to achieve therapeutic goals.

Xenobiotics follow metabolic processes to be removed from the body. This process most commonly involves cytochrome P450 enzymes. These enzymes are a super family of proteins found in all living organisms. In humans, as well as all other mammalian species, this enzyme system is found principally in the liver but exists in all other organs and tissues. These enzymes catalyze the following reactions: aromatic hydroxylation; aliphatic hydroxylation; N-, O-, and S-dealkylation; N-hydroxylation; N-oxidation; sulfoxidation and deamination. Of particular importance to the present invention are the breakdown processes that the vesicles formed from news lipids, and the new lipids themselves, are expected to undergo. Methoxyl and methylamine groups are expected to undergo demethylation. Amines are expected to undergo N-oxidation or deamination. Sulfur bonds are expected to undergo S-oxidation. Esters and amides are expected to undergo hydrolysis. Since different organs and tissues have differing abilities to perform these different reactions, it is a further objective of the present invention to provide linkers with optimal degradation properties.

Similarly different microenvironments within the body favor different breakdown processes. For example, acidic gastric fluids favors breakdown of thiol linkages. Therefore, it is still another object of this invention to provide new molecules for improving the biocompability of a therapeutic agent and for designing drug delivery formulations for diverse physiological microenvironments.

Of the three linked PEG, carbohydrate and lipophilic components, carbohydrate and sterol or lipo-vitamins are digestible by humans while PEG is not. Breaking the linkage among the three components may result in increased clearance for all. It is therefore an object of the invention to use varying biodegradable linkers for optimizing clearance rates of lipid vesicles and lipids used for drug delivery.

When attached to a polymer, any inherit property of the molecules may be inactive. It is therefore an object of the invention to use less biodegradable linkers for stabilizing the bond between the central backbone and the carrier groups, especially when a portion of the conjugates alone may be relatively toxic.

In one aspect of the present invention involves coupling reactions of the conjugates with one or more or combination or in series of alkylation including N-alkylation or O-alkylation, etherification, esterification and amidation chemical processes. For practical and economic reasons, it is preferable making those conjugates from simple processes whenever possible at low costs.

Retaining power of lipids may be important in drug formulations and preventing drug precipitation from dilution or cyclation in the body fluids. The present invention provides the means of enhancing retaining power by inclusion more hydrophobic carrier groups into polymer-carbohydrate conjugates. In addition, with increased retaining power of the conjugates, the use of preservative may be eliminated for parenteral products since the sterile filtration is possible with a relative low concentration of the polymer conjugates in the dosage forms which typically form a true solution product.

The sugar groups in the conjugates of the invention have larger surface polarity than polymer chains or lipophilic carriers. For instance, those PEG-carbohydrate conjugates provide a better drug dispersion for their applications in nano-suspension or nanoparticles, especially for some amphiphatic drugs or other compounds; this provides a better equilibrium for the drug or other compounds to partition into the lipophilic bilayers of the vesicles.

When using existing PEG-lipids such as Capmul®, Centrophase®, Cremophor®, Labrafac®, Labrafil®, Labrasol® and Myverol® for oral liquid formulations, a taste masking agent may be used which may have additional issues for manufacturing processes and costs. PEG-carbohydrate conjugates generally taste better than other types of PEG-lipids conjugates, and elimination of the need for taste making agents is possible.

PEG-carbohydrate conjugates in the present invention may be formulated into injectable preparations free from sugars which are commonly used to stabilize lyophilized proteins and peptides for injectables. Injectables prepared with PEG-carbohydrate conjugates are very stable even under high temperature or high humidity conditions. Reducing or eliminating the use of sugars in pharmaceutical preparation is especially beneficial for patients with diabetes mellitus.

The polymer chains in the conjugates of the present invention are preferably monodisperse PEG. Materials and methods for synthesizing such monodisperse PEG chains are disclosed in U.S. patent application Ser. No. 12/802,197, which is hereby incorporated by reference in its entirety. Preferably more than 30% of the PEG chains in a particular conjugate have the same molecular weight. More preferably, more than 50% have the same molecular weight. Most preferably, more than 80% have the same molecular weight.

Generally, the present invention includes compositions and methods for synthesizing PEG-carbohydrate-sterol/(or lipophilic vitamin) conjugates comprising a central backbone with one PEG chain and one carbohydrate group and one lipophilic group bonded to the backbone. The conjugation undergoes alkylation including N-alkylation or O-alkylation, etherification, esterification and amidation chemical processes. Selected linkers may be used to form ester or ether or amide bonds between the backbone and the PEG chain or the carbohydrate or the lipophilic group or prior to the conjugation to the center backbones. The backbone comprises glycerol or glycerol-liking having three available binding positions or diamines, triamines, tetraamine and polyamines or diaminoalcohol or amino acids having three available binding positions and the lipophilic carrier group comprises cholesterol or cholesterol-like having a single hydroxyl group or tocopherol or tocotrienol or cholecalciferol or retinol, retinal, and retinoic acid.

Variations of the invention include a variety of compounds as for the central backbone with at least three available binding positions. Molecules having two available binding positions, such as diamines, aminoalcohols or amino acids may be chemically extended to three binding sites.

While positional isomers may be produced during synthesis of the polymer-carbohydrate-lipid conjugates, such isomers may be functionally equivalent. However, the choice of isomer may have implications in a variety of delivery process such as intracellular transport of lipophilic molecules as well as their use as vehicles in pharmaceutical applications. For example, isomers may differ in the ability to stabilize a compound during solubilizing and storage.

Though it is possible to use a variety of central backbone for the preparation of a polymer-carbohydrate conjugates, incorporating linear or cyclic central backbones in practicing the invention is demonstrated to be very powerful, because of a sterol or tocopherol or cholecalciferol may largely increase handling ability of "like dissolves like." In General Structure 1, the backbone may be selected from glycerol or glycerol-like analogues, polyamines (di- or tri- or tetra- or penta-amines), amino acids having three available binding sites, and triols and triacids such as glucoheptonic acid and tartaric acid. The lipophilic component may be selected from a group of compounds including but not limited to cholesterol, stigmasterol, ergosterol, hopanoids, phytosterol, sitosterol, campesterol, brassicasterol, avenasterol adosterol, and stanols (saturated steroid alcohols or hydrogenated sterols), retinoids, retinals, retinoic acid, tretinoin, carotenoids, β-carotene, α-tocopherol, tocotrienols, cholecalciferol, ergocalciferol, astaxanthin, auroxanthin, capsanthin, capsorubin, chrysanthemaxanthin, cryptoxanthin, fucoxanthin, lutein, neoxanthin, rubixanthin, violaxanthin, zeaxanthin. The carbohydrate is a sugar including monosaccharides or disaccharides or oligosaccharides or amino sugars or sugar acids. $X_1$, $X_2$ and $X_3$ are the same or different linkers of carbon-nitrogen bond, ester or ether or amide between carrier groups and center backbones. Each linker may be as simple as oxygen or other single atom. Alternatively, each linker may be single or replicate linkers selected from Table 2 or Table 3. In some cases, the linker may be co-extensive with or a part of the backbone or functional group component used to synthesize the conjugate. Though not shown, the invention also includes compounds in which the carbohydrate is in the center position of the backbone. However, it is more practical to have carbohydrates at the terminus instead of the center of the backbones due to the routes of synthetic chemistry. The general structure is meant to include all racemers or structural isomers of the structure, as they may be functionally equivalent. The PEG chain preferably consists of between about 5 and 45 subunits, and is preferably substantially monodisperse. R is the terminal group on the PEG chain may be selected from a wide variety of chemical moieties. R preferably has a molecular weight of less than about 650.

Table 2 describes amino acid linkers ("X") useful in practicing the invention.

TABLE 2

Amino Acid Linkers

| No | Amino Acid | Side chain charge at pH 7.4 [a] |
|---|---|---|
| 1 | Alanine | Neutral |
| 2 | Arginine | Positive |
| 3 | Asparagine | Neutral |
| 4 | Aspartic acid | Negative |
| 5 | Cysteine | Neutral |
| 6 | Glutamic acid | Negative |
| 7 | Glutamine | Neutral |
| 8 | Glycine | Neutral |
| 9 | Histidine | Positive/neutral |
| 10 | Isoleucine | Neutral |
| 11 | Leucine | Neutral |
| 12 | Lysine | Positive |
| 13 | Methionine | Neutral |
| 14 | Phenylalanine | Neutral |
| 15 | Proline | Neutral |
| 16 | Serine | Neutral |
| 17 | Threonine | Neutral |
| 18 | Tryptophan | Neutral |
| 19 | Tyrosine | Neutral |
| 20 | Valine | Neutral |

[a] Hausman, Robert E.; Cooper, Geoffrey M. (2004). The cell: a molecular approach. Washington, D.C: ASM Press. p. 51

Preferable amino acid linkers are proline, glycine, alanine, lysine, cysteine, valine, isoleucine, leucine, methionine, phenylalanine, histidine, tryptophan, tyrosine, selenocysteine, and arginine, more preferable are proline, glycine, alanine, lysine, cysteine, valine, isoleucine, leucine, methionine, most preferable are proline, glycine, and alanine.

Conjugates of the present invention may comprise the linkers as listed in Table 3. The structures shown in the table were mainly named by ChemDraw (CambridgeSoft, Cambridge, Mass., USA). In the event of minor variations of chemical names, the structures shown are meant to be controlling.

TABLE 3

Other linkers use in the invention

| No | Symbol | Linker |
|---|---|---|
| 1 | $N_1$ | 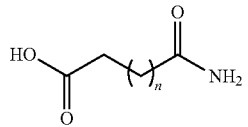<br>n = 1 to 18, carbamoyl-carboxylic acid |
| 2 | $N_2$ | 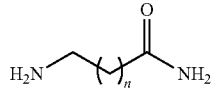<br>n = 1 to 18: n-amino-alkyl-amide |

TABLE 3-continued

Other linkers use in the invention

| No | Symbol | Linker |
|---|---|---|
| 3 | $N_3$ | HO-(CH2)n-C(=O)-NH2<br>n = 1 to 18: n-hydroxyl-alkyl-amide |
| 7 | $N_7$ | H2N-C(=O)-(CH2)n-C(=O)-NH2<br>n = 1 to 18, alkyl diamide |
| 8 | $N_8$ | H2N-(CH2)n-CH(NH2)-COOH<br>n = 1 to 18, diamino-carboxylic acid |
| 9 | $N_9$ | HO-(CH2)n-NH2<br>n = 2 to 18: n-aminoalcohol |
| 10 | $N_{10}$ | H2N-(CH2)n-NH2<br>n = 2 to 18: diamine |
| 11 | $N_{11}$ | HO-C(=O)-NH-(CH2)n-NH2<br>n = 1 to 18: n-amino-alkyl-carbamic acid |
| 12 | $N_{12}$ | H2N-C(=O)-(CH2)-S-(CH2)n-NH2<br>n = 1 to 12: n-amino(methyl-thio)$_n$-propanamide |
| 13 | $S_1$ | HS-(CH2)n-COOH<br>n = 1 to 18: n-mercaptocarboxylic acid |
| 14 | $S_2$ | HS-(CH2)n-CH(NH2)-COOH<br>n = 1 to 18: n-mercapto-alpha-aminocarboxylic acid |
| 15 | $S_3$ | HO-C(=O)-NH-(CH2)n-SH<br>n = 1 to 18: n-mercapto-alkyl-carbamic acid |
| 16 | $S_4$ | HOOC-CH(R)-S-(CH2)n-SH<br>R = H or Alkyl group, n = 0 to 18 |
| 17 | $S_5$ | HOOC-CH(R)-S-(CH(OH))-(CH2)n-CH(OH)-SH<br>R = H or Alkyl group<br>n = 0 to 12: n-mercaptopropylthio)carboxylic acid |
| 18 | $S_6$ | HS-(CH2)n-NH2<br>n = 1 to 18: Amino-thiol |
| 19 | $S_7$ | HS-(CH2)n-OH<br>n = 1 to 18: n-mercapto-alcohol |
| 20 | $S_8$ | HS-(CH2)n-SH<br>n = 1 to 18: dithiol |
| 21 | $S_9$ | HO-C(=O)-(CH2)-S-(CH2)n-NH2<br>n = 1 to 18: n-amino-(methyl-thio)$_n$-propanoic acid |
| 22 | $Aa_1$ | CH2=CH-COOH<br>acrylic acid |
| 23 | $Aa_2$ | CH2=CH-C(=O)-O-CH3<br>methyl acrylate |
| 24 | $Ac_1$ | HO-(CH2)n-COOH<br>n = 1 to 18: n-hydroxy-carboxylic acid |
| 25 | $Ac_2$ | H2N-(CH2)n-COOH<br>n = 1 to 18: n-amino-carboxylic acid |
| 26 | $Ac_3$ | HOOC-(CH2)n-COOH<br>n = 1 to 18: di-carboxylic acid, n = 1: succinyl |

TABLE 3-continued

Other linkers use in the invention

| No | Symbol | Linker |
|---|---|---|
| 27 | $Ac_4$ | 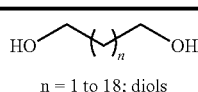 n = 1 to 18; diols |
| 28 | $Ac_5$ | 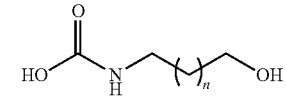 n = 1 to 18: n-hydroxy-alkyl-carbamic acid |
| 29 | $Ac_6$ | 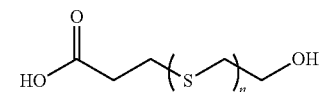 n = 1 to 18: n-hydroxyl-(methyl-thio)$_n$-propanoic acid |

In this aspect of the invention, in the general structure 1, X may comprise one or more carbon atoms in addition to the linker forming an N-alkylation or O-alkylation, ester or ether or amide bond between the carriers and center backbone. Whenever suitable, a simple and low cost coupling process should be chosen to void multiple linkers such as forming a peptide and the linker is preferably oriented so that the backbone is readily coupling to the carrier groups.

The present invention may be practiced using a variety of central backbones void drug moieties. Preferable backbones have at least three available or two expandable positions for carbohydrate or lipid or PEG attachments through alkylation, esterification, etherification or amidation. For those suitable molecules may be used as the backbone including but not limited to the group consisting of ethylenediamine (1,2-diaminoethane, 1,3-diaminopropane (propane-1,3-diamine), putrescine (butane-1,4-diamine), cadaverine (pentane-1,5-diamine), hexamethylenediamine (hexane-1,6-diamine), ethylenediamine, 1,3-diaminopropane, 1,2-diaminopropane, 1,4-diaminobutane, diphenylethylenediamine, diaminocyclohexane, 3-amino-1,2-propanediol, 3-bromo-1,2-propanediol, 3-chloro-1,2-propanediol, 3-fluoro-1,2-propanediol, DL-glyceric acid, diaminopropionic acid, tartaric acid, glucoheptonic acid and, 1,2,4-butanetriol, 2,2-Bis(hydroxymethyl)butyric acid, 1,3-diamino-2-propanol and 2-(3-aminopropylamino)ethanol, 3-((3-aminopropyl)amino)propanol, diethylenetriamine, spermidine, triethylene-tetramine, spermine, norspermidine, bis(3-aminopropyl)-1,3-propanediamine, and bis(hexamethylene)triamine, aspartic acid, glutamic acid, asparagine, glutamine, ornithine, serine and threonine, benzyl triols or aminohydroxybenzoic acids or phenol-like analogues, phenyl diols with a carboxy group or amine, and diamines with a hydroxyl or carboxy group, diaminobenzoic acid, aminohydroxybenzoic acid, aminosalicylic acid, hydroxyanthranilic acid, hydroxyisophthalic acid, aminoisophthalic acid. For example, a suitable center backbone may be selected from 4-(hydroxymethyl)cyclopentane-1,3-diol, deoxyfuconojirimycin, deoxynojirimycin, prostaglandins, hydroxymethylpiperidinol, dihydroxy(hydroxymethyl)aminocyclopentane, diaminophenol, benzene-tetracarboxylic acid, benzenetricarboxylic acid, aminobenzenediol, dihydroxybenzoic acid, aminohydroxybenzoic acid, trihydroxyaniline, benzenetriol, dimethoxybenzenediamine, trihydroxyphenol, (diaminophenoxy)-benzene-diamine or aminobromophenol.

In the present invention, suitable carbohydrates for the polymer-carbohydrate conjugates include mono-saccharides or disaccharides or oligosaccharides as listed in Table 4. In addition to carbohydrates listed in Table 4, their analogues or derivatives are also suitable for making the conjugates including but not limited to sugar alcohol, sugar acids (saccharides with a carboxyl group), ascorbic acid, steviol glycoside (Rebaudioside A), sucralose, lactitol, maltitol, isomalt, maltotriitol, maltotetraitol, mogrosides, glycyrrhizin, inulin, glucoheptonic acid and osladin.

TABLE 4

Carbohydrates for use in the Invention

| Monosaccharide | trioses | ketotriose (dihydroxyacetone) · aldotriose (glyceraldehyde) |
|---|---|---|
| | tetroses | ketotetrose (erythrulose) · aldotetroses (erythrose, threose) |
| | pentoses | ketopentose (ribulose, xylulose), aldopentose (ribose, arabinose, xylose, lyxose), deoxy carbohydrate (deoxyribose) |
| | hexoses | ketohexose (psicose, fructose, sorbose, tagatose), aldohexose (allose, altrose, glucose, mannose, gulose, idose, galactose, talose), deoxy carbohydrate (fucose, fuculose, rhamnose) |
| | others | heptose (sedoheptulose), octose, nonose (neuraminic acid) |
| Multiple | disaccharides | sucrose, lactose, maltose, trehalose, turanose, cellobiose |
| | trisaccharides | raffinose, melezitose, maltotriose |
| | tetrasaccharides | acarbose, stachyose |
| | other oligosaccharides | Fructooligosaccharide, galactooligosaccharides, mannan-oligosaccharides |
| | polysaccharides | polyglycitol, n-acetylglucosamine, chitin, |

The polymer-carbohydrate conjugates of the present invention may be used for many applications. Formulation and delivery of pharmaceutical and cosmetic agents have been described. Additionally, the polymer-carbohydrate conjugates of the present invention may be used in other contexts where water soluble lipids are advantages, for example industrial and food processes The terminal group on the PEG chain may be selected from a wide variety of chemical moieties. Such moieties preferably have a molecular weight of less than 650. Such moieties include —$NH_2$, —COOH, —$OCH_2CH_3$, —$OCH_2CH_2OH$, —$COCH=CH_2$, —$OCH_2CH_2NH_2$, —$OSO_2CH_3$, —$OCH_2C_6H_6$, —$OCH_2COCH_2CH_2COONC_4H_4O_2$, —$CH_2CH_2=CH_2$, $C_{10}H_{16}N_2O_3S$ and —$OC_6H_6$. The terminal group may be a functional group that facilitates linking therapeutic or targeting agents to the surface of micro vesicle aggregates. Amino acids, amino alkyl esters, biotins, maleimide, diglycidyl ether, maleinimido propionate, methylcarbamate, tosylhydrazone salts, azide, propargyl-amine, propargyl alcohol, succinimidyl (NHS) esters (e.g., propargyl NHS ester, NHS-biotin, sulfo-NHS-LC-biotin, or NHS carbonate), hydrazide, succinimidyl ester, succinimidyl tartrate, succinimidyl succinate, and toluenesulfonate salt are useful for such linking. Linked therapeutic and targeting agents may include Fab fragments, cell surface binding agents, and the like. Additionally, the terminal group may include functional cell-targeting ligands such as folate, transferrin and molecules such as monoclonal antibodies, ligands for cellular receptors or specific peptide sequences may be attached to the liposomal surface to provide specific binding sites.

The terminal group may be neutral or include either negatively or positively charged head-groups such as decanolamine, octadecylolamine, octanolamine, butanolamine, dodecanolamine, hexanolamine, tetra-decanolamine, hexadecanolamine, oleylamine, decanoltrimethylaminium, octadecyloltrimethylaminium, octanoltrimethyl-aminium, butanoltrimethylaminium, dodecanoltrimethylaminium, hexanoltrimethylaminium, tetradecanoltrimethylaminium, hexadecanoltrimethylaminium, oleyltrimethylaminium, for example. Other useful R groups include alkyl groups such as alkoxy moieties, amino acids, and sugars including monosaccharides, ascorbic acid, gluconic acid, glucaric acid, glucuronic acid, galacturonic acid, disaccharides, trisaccharides and the oligosaccharides containing 1, 2, 3, and 4 or more monosaccharide units respectively. Additionally, targeting moieties such as antibody fragments and vitamins may also be used as R groups. Generally, the R group is highly soluble in water. The molecular weight of the R group is preferably less than about 650, and for most applications the R group is preferably easily polarized, in order to increase the binding and interaction with proteins at the targeted sites. However, well balanced ionic R groups are advantageously employed for certain modes of administrations such as topical gels and oral solutions targeting the mouth and throat.

Depending on the choice of backbone, functional groups and linkers, the compounds of the invention may be categorized into several classes. These classes include cholesterylglycerolcarbohydrate-polyethylene glycols (CGC-PEGs); tocopherylglycerolcarbohydrate-polyethylene glycols (TGC-PEGs); cholesteryldiethylenetetramine-carbohydrate-polyethylene glycols (CDC-PEGs); tocopheryldiethylenetetramine-carbohydrate-polyethylene glycols (TDC-PEGs); cholesteryltriethylenetetramine-carbohydrate-polyethylene glycols (CTC-PEGs); and tocopheryltriethylenetetramine-carbohydrate-polyethylene glycols (TTC-PEGs).

In another aspect the invention includes a PEG-carbohydrate conjugate with three carriers having the General Structures:

| General Structure 2 | |
|---|---|
| Formula | Structure |
| General Structure 2 | Sugar–Backbone–H, PEG–R |
| General Structure 3 | Sugar–Backbone-X–H, PEG–$R_i$ |
| General Structure 4 | Sugar–Backbone-$X_1$–H, $X_2$, PEG–$R_i$ |
| General Structure 5 | Sugar–Backbone-$X_1$–$H_2$–PEG–$X_2$, PEG–$H_1$ |
| General Structure 6 | Sugar-$PEG_2$, $X_2$, Backbone-$X_1$–H, $PEG_1$–R |

| General Structure 2 -continued | |
|---|---|
| Formula | Structure |
| General Structure 7 | Sugar-$PEG_2$, $X_2$, Backbone-$X_1$, $X_3$, H—$PEG_3$, $PEG_1$—$R_i$ | where the backbone is selected from glycerol or glycerol-like analogues or linear amines (di- or tri- or tetra-amines) or amino acids having three available binding sites including and not limited to selected from the group consisting of diethylenetriamine, bis(3-aminopropyl)-amine or bis(3-aminopropyl)-1,3-propanediamine or N,N'-bis(3-aminopropyl)-1,3-propanediamine, triethylenetetramine or 1,2-bis(3-aminopropylamino)ethane, spermine, tris(2-aminoethyl)amine, spermidine, norspermidine, bis(hexamethylene)triamine, tris(hydroxymethyl)aminomethane, diaminobenzidine, triazacyclononane, tetraazacyclododecane, threitol, meso-erythritol, dithiothreitol, trimethylcyclohexane-1,3,5-tricarboxylic acid or 1,3,5-cyclohexanetricarboxylic acid, trimethylbis(hexa-methylene)triamine, arginine, oxylyldiaminopropionic acid having three or four available binding positions or sites, triols, triacids, glucoheptonic acid, and tartaric acid; where the H ($H_1$ or $H_2$ may be the same or different lipophilic group) is sterol or fat soluble vitamin or alike selected from a group of lipophilic compounds or their diesters including and not limited to cholesterol, stigmasterol, ergosterol, hopanoids, phytosterol, sitosterol, campesterol, brassicasterol, avenasterol adosterol, and stanols (saturated steroid alcohols or hydrogenated sterols), retinoids, retinals, retinoic acid, tretinoin, carotenoids, β-carotene, tocopherols, tocotrienols, cholecalciferol, ergocalciferol, astaxanthin, auroxanthin, capsanthin, capsorubin, chrysanthemaxanthin, cryptoxanthin, fucoxanthin, lutein, neoxanthin, rubixanthin, violaxanthin, zeaxanthin; the Sugar is a carbohydrate including monosaccharides ascorbic acid, gluconic acid, glucaric acid, glucuronic acid, galacturonic acid or disaccharides or oligosaccharides; where the three substitutable groups are covalently bond to the backbone through a etherification or esterification or amidification or similar substitution reactions. The General Structure is meant to include all racemers or structural isomers of the structure, as they may be functionally equivalent. Where the PEG ($PEG_1$ or $PEG_2$ or $PEG_3$ may be the same of different polymer) chain may consist of between about 5 and 45 subunits. More preferably the PEG chain consists of between about 4 and 25 subunits. Where R (or $R_i$) is the terminal group on the PEG chain may be selected from a wide variety of chemical moieties. R preferably has a molecular weight of less than about 650. The PEG-carbohydrate-sterol conjugates are useful for applications other than liposomes, e.g., as a solubility enhancer in water solution. Even though no linker group is presented in the General Structures, modifications of carrier groups or center backbones may be necessary prior to the coupling reactions, those chemical modifications may be required for alkylation, etherification, esterification or amidation chemical processes between the carrier groups and the center backbone. Ideally selected carriers or center backbones may be used for the coupling reactions directly without a modification. Where X ($X_1$, $X_2$ or $X_3$ may be the same or different linkers) is one or more linkers selected from the Table 2 or 3 or groups consisting of oxy, amino acids, amino, succinylamino, acetamido, aminopentanamido, aminoacetyl, thiopropanoayl, N-(mercapto-methyl)propionamido, mercapto-propylthio) propanoyl, (1,2-dihydroxy-3-mercapto-propythio)-propanoyl, succinyl, acetyl, oxopentanoyl, carbamoyl, aminoalkyl, glutaramido, aminoethanethiol, mercaptopropanol, (hydroxypropylthio)propanoayl, 3-((2-propion-amidoethyl) disulfanyl)-propanoayl, (((acetamido-ethyl)disulfanyl)propanoyloxy)glutaramido, aminoethanethioate, and 2-hydroxyacetic proprionic anhydride.

In another aspect the invention includes a molecule comprising a compound represented by the following General Structure 8:

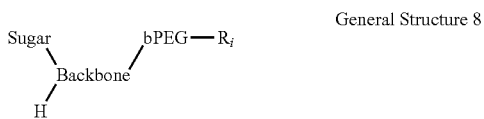

General Structure 8

Where the backbone is selected from glycerol or glycerol-like analogues or linear amines (di- or tri- or tetra-amines) or amino acids having three available binding sites selected from a group of molecules including but not limited to glycerol or glycerol-like analogues, polyamines, triamines, tetraamines, aminodiol, aminotriols, aminoalcohols and amino acids having three available binding positions or sites, triols, tetraols, erythritol, triacids, tetracid, tetraacetic acid, glucoheptonic acid, and tartaric acid, including but not limited to ethylenediamine (1,2-diaminoethane, 1,3-di-aminopropane (propane-1,3-diamine), 4-amino-3-hydroxy-butyric acid, N-(2-hydroxyethyl)-ethylenediamine, 4-amino-2-hydroxybutyric acid, 2-hydroxy-4-aminobutylic acid, 1-β-homoserine, 1-threonine, N-β-aminoethyl-glycine, putrescine (butane-1,4-diamine), cadaverine (pentane-1,5-diamine), hexamethylenediamine (hexane-1,6-diamine), ethylenediamine, 1,3-diaminopropane, 1,2-diaminopropane, 1,4-diaminobutane, diphenylethylenediamine, diaminocyclohexane. diethylenetriamine, bis(3-aminopropyl)-amine, triethylenetetramine, tris(2-aminoethyl)amine, spermine, spermidine, norspermidine, bis(3-aminopropyl)-1,3-propanediamine, 1,2-bis(3-aminopropylamino)ethane, N,N'-bis (3-aminopropyl)-1,3-propanediamine, 3-amino-1,2-propanediol, aminoalcohols, tris(hydroxymethyl) aminomethane, diaminobenzidine, N-ethyl-N'-(3-dimethylaminopropyl)carbodiimide, mesoerythritol, triazacyclononane, tetraazacyclododecane, threitol, dithiothreitol, trimethylcyclohexane-1,3,5-tricarboxylic acid, trimethylbis(hexa-methylene)triamine, bis(hexamethylene) triamine, arginine, oxylyldiaminopropionic acid, 3-bromo-1,2-propanediol, 3-chloro-1,2-propanediol, 3-fluoro-1,2-propanediol, DL-glyceric acid, diaminopropionic acid, glucoheptonic acid and, 1,2,4-butanetriol, 2,2-bis(hydroxymethyl)-butyric acid, 1,3-diamino-2-propanol and 2-(3-Aminopropylamino)-ethanol, and 3-((3-aminopropyl)-amino)propanol; aspartic acid, glutamic acid, asparagine, glutamine, lysine, ornithine, serine, and threonine or benzyl triols or aminohydroxybenzoic acids or benzenetriol, dihydroxybenzoic acid, diaminobenzoic acid, diaminophenol, diaminobenzoic acid, aminohydroxybenzoic acid, aminosalicylic acid, aminohydroxyanthranilic acid, hydroxyisophthalic acid, aminoisophthalic acid, 4-(hydroxymethyl)cyclopentane-1,3-diol, deoxyfuconojirimycin, deoxynojirimycin, prostaglandins, hydroxylmethylpiperidinol, dihydroxy(hydroxymethyl)-aminocyclopentane, diaminophenol, benzenetetracarboxylic acid, benzenetricarboxylic acid, aminobenzenediol, dihydroxybenzoic acid, aminohydroxybenzoic acid, trihydroxyaniline, benzenetriol, dimethoxybenzenediamine, trihydroxyphenol, (diaminophenoxy)benzenediamine and aminobromophenol; where the H is selected from a group of lipophilic compounds or their diesters including and not limited to cholesterol, stigmasterol, ergosterol, hopanoids, phytosterol, sitosterol, campesterol, brassicasterol, avenasterol adosterol, and stanols (saturated steroid alcohols or hydrogenated sterols), retinoids, retinoic acid, tretinoin, carotenoids, β-carotene, α-tocopherol, tocotrienols, cholecalciferol, ergocalciferol, astaxanthin, auroxanthin, capsanthin, capsorubin, chrysanthemaxanthin, cryptoxanthin, fucoxanthin, lutein, neoxanthin, rubixanthin, violaxanthin, zeaxanthin; Sugar is a carbohydrate including monosaccharides or disaccharides or oligosaccharides or amino sugars or sugar acids including but not limited to ascorbic acid, gluconic acid, glucaric acid, glucuronic acid, galacturonic acid; where the three substitutable groups are covalently bond to the backbone through a etherification or esterification or amidification or similar substitution reactions. The General Structure is meant to include all racemers or structural isomers of the structure, as they may be functionally equivalent. Where the bPEG is a branched PEG with 2 or more PEG chains and each PEG chain may consist of between about 5 and 45 subunits. For example, a branched PEG contains two linear methoxy PEG chain attached to a central core is so called "Y-shaped" PEG. While a 2-branched PEG is more common, 3-branched and 4-branched are also commercially available. Where $R_i$ is the terminal group on each PEG chain which may be the same or different and that may be selected from a wide variety of chemical moieties. $R_i$ preferably has a molecular weight of less than about 650. The PEG-carbohydrate conjugates are useful for applications other than liposomes, e.g., as a solubility enhancer of poor water soluble agents in aqueous solutions.

In another aspect the invention includes a PEG-carbohydrate conjugate with four carriers having the following General Structures:

| General Structures 9-14 | |
|---|---|
| Formula | Structure |
| General Structure 9 | Sugar\Backbone/PEG—R, $H_1$, $H_2$ |
| General Structure 10 | Sugar\Backbone-X/PEG—R, $H_1$, $H_2$ |
| General Structure 11 | Sugar\Backbone-$X_1$/PEG—R, $H_2$—$X_2$, $X_2$—$H_2$ |
| General Structure 12 | Sugar\Backbone-$X_1$/$PEG_1$—$R_1$, H—$X_2$, $X_1$\$PEG_2$—$R_2$ |

-continued

General Structures 9-14

| Formula | Structure |
|---|---|
| General Structure 13 | 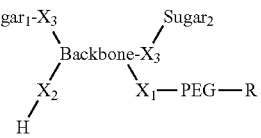 |
| General Structure 14 | 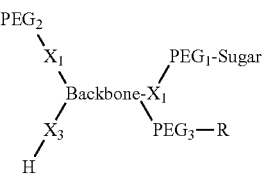 | where H ($H_1$ and $H_2$ may be the same or different lipophilic carrier) is sterols or "fat soluble" vitamins or alike selected from a group of lipophilic compounds or their diesters including and not limited to cholesterol, stigmasterol, ergosterol, hopanoids, phytosterol, sitosterol, campesterol, brassicasterol, avenasterol adosterol, and stanols (saturated steroid alcohols or hydrogenated sterols), retinoids, retinals, retinoic acid, tretinoin, carotenoids, β-carotene, tocopherols, tocotrienols, cholecalciferol, ergocalciferol, astaxanthin, auroxanthin, capsanthin, capsorubin, chrysanthemaxanthin, cryptoxanthin, fucoxanthin, lutein, neoxanthin, rubixanthin, violaxanthin, zeaxanthin; if $H_1$ and $H_2$ are different carriers other than sterols or fat soluble vitamins, one (the fourth carrier) of the two may be selected from fatty acids saturated or unsaturated lipid or polyunsaturated fatty acids as listed in Table 5 or polyunsaturated fatty alcohols including native polyunsaturated alcohols such as farneol, solanesol and dodecaprenol, however fatty acids may only be selected as the secondary lipophilic carrier in the presence of a sterol as the primary lipophilic carrier and restrically avoided to be utilized as the primary lipophilic carrier due to their potential hemolytic property; where the backbone is selected from triamines, tetramines or polyamines or compounds having four available binding sites; where the fourth carrier is selected from diesters including and not limited to sterol-acylglycerols or disterolglycerols; Sugar is a carbohydrate including monosaccharides, ascorbic acid, gluconic acid, glucaric acid, glucuronic acid, galacturonic acid or disaccharides or oligosaccharides or amino sugars and sugar acids; where the three substitutable groups are covalently bond to the backbone through a etherification or esterification or amidification or similar substitution reactions. The General Structure is meant to include all racemers or structural isomers of the structure, as they may be functionally equivalent. Where the PEG chain (($PEG_1$, $PEG_2$ and $PEG_3$ chain may be the same or different in length) may consist of between about 5 and 45 subunits. Where R ($R_1$ and $R_2$ may be the same of different) is the terminal group on the PEG chain may be selected from a wide variety of chemical moieties. R preferably has a molecular weight of less than about 650. The PEG-carbohydrate conjugates are useful for applications other than liposomes, e.g., as a solubility enhancer in water solutions.

TABLE 5

Polyunsaturated fatty acids for the fourth carrier in the invention

| Common name | Lipid name | Chemical name |
|---|---|---|
| Hexadecatrienoic acid | 16:3 (n-3) | all-cis 7,10,13-hexadecatrienoic acid |
| Stearidonic acid | 18:4 (n-3) | all-cis-6,9,12,15,-octadecatetraenoic acid |
| Eicosatrienoic acid | 20:3 (n-3) | all-cis-11,14,17-eicosatrienoic acid |
| Eicosatetraenoic acid | 20:4 (n-3) | all-cis-8,11,14,17-eicosatetraenoic acid |
| Eicosapentaenoic acid | 20:5 (n-3) | all-cis-5,8,11,14,17-eicosapentaenoic acid |
| Heneicosapentaenoic acid | 21:5 (n-3) | all-cis-6,9,12,15,18-heneicosapentaenoic acid |
| Docosapentaenoic acid | 22:5 (n-3) | all-cis-7,10,13,16,19-docosapentaenoic acid |
| Docosahexaenoic acid | 22:6 (n-3) | all-cis-4,7,10,13,16,19-docosahexaenoic acid |
| Tetracosapentaenoic acid | 24:5 (n-3) | all-cis-9,12,15,18,21-tetracosapentaenoic acid |
| Tetracosahexaenoic acid | 24:6 (n-3) | all-cis-6,9,12,15,18,21-tetracosahexaenoic acid |
| Docosadienoic acid | 22:2 (n-6) | all-cis-13,16-docosadienoic acid |
| Adrenic acid | 22:4 (n-6) | all-cis-7,10,13,16-docosatetraenoic acid |
| Docosapentaenoic acid | 22:5 (n-6) | all-cis-4,7,10,13,16-docosapentaenoic acid |
| Tetracosatetraenoic acid | 24:4 (n-6) | all-cis-9,12,15,18-tetracosatetraenoic acid |
| Tetracosapentaenoic acid | 24:5 (n-6) | all-cis-6,9,12,15,18-tetracosapentaenoic acid |
| Rumenic acid | 18:2 (n-7) | 9Z,11E-octadeca-9,11-dienoic acid |
| Rumenic acid | 18:2 (n-6) | 10E,12Z-octadeca-9,11-dienoic acid |
| α-Calendic acid | 18:3 (n-6) | 8E,10E,12Z-octadecatrienoic acid |
| β-Calendic acid | 18:3 (n-6) | 8E,10E,12E-octadecatrienoic acid |
| Jacaric acid | 18:3 (n-6) | 8Z,10E,12Z-octadecatrienoic acid |
| α-Eleostearic acid | 18:3 (n-5) | 9Z,11E,13E-octadeca-9,11,13-trienoic acid |
| β-Eleostearic acid | 18:3 (n-5) | 9E,11E,13E-octadeca-9,11,13-trienoic acid |
| Catalpic acid | 18:3 (n-5) | 9Z,11Z,13E-octadeca-9,11,13-trienoic acid |
| Punicic acid | 18:3 (n-5) | 9Z,11E,13Z-octadeca-9,11,13-trienoic acid |
| Rumelenic acid | 18:3 (n-3) | 9E,11Z,15E-octadeca-9,11,15-trienoic acid |
| α-Parinaric acid | 18:4 (n-3) | 9E,11Z,13Z,15E-octadeca-9,11,13,15-tetraenoic acid |
| β-Parinaric acid | 18:4 (n-3) | all trans-octadeca-9,11,13,15-tretraenoic acid |
| Bosseopentaenoic acid | 20:5 (n-6) | 5Z,8Z,10E,12E,14Z-eicosanoic acid |

Similar to the three carrier conjugates, synthesis of the new conjugates may be controlled so that there is a single linker in each PEG-carbohydrate conjugate. In some situations, however, it may be useful to have multiple copies of the same linker, or combinations of different linkers in a single molecule in the following General Structures, where $X_1$ and $X_2$ are the same or different linkers that consist of one or more linkers selected from the Table 2 or 3 or the group of oxy, amino, succinylamino, acetamido, aminopentanamido, aminoacetyl, thiopropanoayl, acryloyl, N-(mercaptomethyl)propionamido, mercaptopropylthiopropanoyl, (1,2-dihydroxy-3-mercapto-propylthio)propanoyl, succinyl, acetyl, oxopentanoyl, carbamoyl, aminoalkyl, glutaramido, aminoethanethiol, mercaptopropanol, (hydroxypropylthio) propanoayl, 3-((2-propionamidoethyl)-disulfanyl)propanoayl, (((acet-amidoethyl)disulfanyl)propanoyloxy)glutaramido, aminoethanethioate, and 2-hydroxyacetic proprionic anhydride. More preferably R ($R_1$ and $R_2$ may be the same or different) has a molecular weight of less than about 650. $H_1$ and $H_2$ are the same or different. The secondary H may be selected from the group consisting of saturated fatty acid) or unsaturated fatty acid and polyunsaturated fatty acids as listed in Table 5 or polyunsaturated fatty alcohols including native polyunsaturated alcohols such as farnesol, solanesol and dodecaprenol. However no fatty acid may be selected as the first or primary lipophilic carrier. Sugar may preferably be selected from Table 4, the group consisting of aldose, ketose, pyranose, furanose, trioses, tetroses, pentoses, hexoses, sucrose, lactose, maltose, trehalose, turanose, cellobiose, raffinose, melezitose, maltotriose, acarbose, stachyose and sugar acids. The PEG chain may consist of between about 6 and 45 subunits. More preferably the PEG chain consists of between about 8 and 25 subunits. Still more preferably the PEG chain consists of between about 12 and 25 subunits.

In another aspect the invention includes a molecule comprising a compound represented by the following General Structure 15:

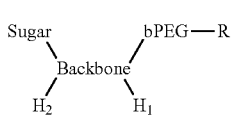

General Structure 15 where $H_1$ and $H_2$ may be the same or different selected from a group of lipophilic compounds including and not limited to cholesterol, stigmasterol, ergosterol, hopanoids, phytosterol, sitosterol, campesterol, brassicasterol, avenasterol adosterol, and stanols (saturated steroid alcohols or hydrogenated sterols), retinals, retinoids, retinoic acid, tretinoin, carotenoids, β-carotene, tocopherols, tocotrienols, cholecalciferol, ergocalciferol, astaxanthin, auroxanthin, capsanthin, capsorubin, chrysanthemaxanthin, cryptoxanthin, fucoxanthin, lutein, neoxanthin, rubixanthin, violaxanthin, zeaxanthin; if $H_1$ and $H_2$ are different, the fourth carrier group may be selected from other hydrocarbons of fatty acids or polyunsaturated or cyclic compounds or their diesters including and not limited to saturated fatty acids and unsaturated fatty acids or polyunsaturated fatty acids as listed in Table 5 or polyunsaturated fatty alcohols including native polyunsaturated alcohols such as farnesol, solanesol and dodecaprenol; where the backbone is selected from polyamine or compounds having four available binding sites; sugar is a carbohydrate including monosaccharides or disaccharides or oligosaccharides or amino sugar or sugar acids including but not limited to ascorbic acid, gluconic acid, glucaric acid, glucuronic acid, galacturonic acid; where the four substitutable groups are covalently bond to the backbone through a etherification or esterification or amidification or similar substitution reactions. The General Structure is meant to include all racemers or structural isomers of the structure, as they may be functionally equivalent. Where the bPEG is a branched PEG with 2 or more PEG chains and each PEG chain may consist of between about 5 and 45 subunits. Where R is the terminal group and may be selected from a wide variety of chemical moieties. R preferably has a molecular weight of less than about 650. The PEG-carbohydrate conjugates are useful for applications other than liposomes, e.g., as a solubility enhancer in water solutions.

In one aspect of the current invention, coupling reactions of alkylation, etherification, esterification or amidation between the carriers and center backbone may be achieved with or without added-on linker groups depending on particular center backbones and carrier groups of the conjugates as summarized in the General Structure 16;

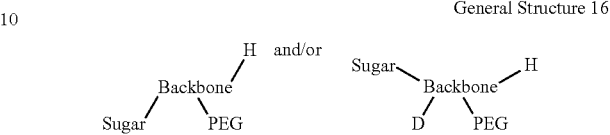

General Structure 16

Where H is a lipophilic carrier carrier void of either steroid acids or fatty acids. H may be selected from a group comprises cholesterol or sterols having a single hydroxyl group or tocopherols or cholecalciferols or retinols; Sugar is a carbohydrate comprises saccharide; PEG is a polymer of polyethylene glycols, D is a secondary sterol or lipophilic vitamin carbohydrate or PEG or carbohydrate or a fatty acid. Backbone is a molecule void of a drug moiety comprises glycerol or glycerol-liking having three available binding positions or diamines, triamines, tetraamine or diaminoalcohol or aminoalcohols or aminodiol or aminotriols or amino acids having three available binding positions and polyamines having at least three available binding sites or positions.

A further aspect of the invention, the third and fourth carriers of the carbohydrate-polymers may be formed through a linked conjugation as presented in the General Structure 17.

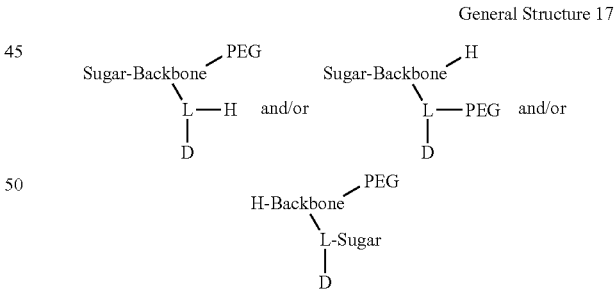

General Structure 17 where D is a secondary sterol or lipophilic vitamin carbohydrate or PEG or carbohydrate or a fatty acid; L is a coupler selected from a group of molecules included but not limited to glycerol or glycerol-liking having three available binding positions or diamines, triamines, tetraamine or diaminoalcohol or aminoalcohols or aminodiol or aminotriols or amino acids having three available binding positions. As showed in Chemical Structure 3, N-bis-monomethoxy-PEG-ether-serinol-N-cholesterol-N'-lactobionoyl-propanediamine, the coupler is 3-Amino-1,2-propanediol (serinol) and the "D" is a secondary mPEG.

Chemical Structure 3

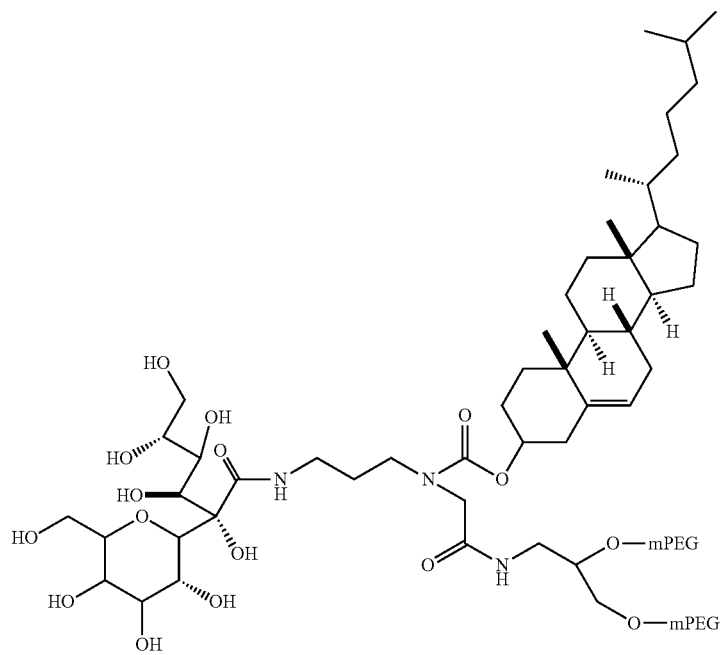

Another aspect of the invention includes a method of delivering a compound, where the method comprises preparing a PEG-carbohydrate conjugate based formulation of the compound, where the formulation comprises a PEG-carbohydrate conjugates having an amino acid linker and possible secondary linker(s) selected from the group consisting of amino, succinylamino, acetamido, aminopentanamido, aminoacetyl, acryloyl, thiopropanoayl, N-(mercaptomethyl)-propionamido, mercaptopropylthiopropanoyl, (1,2-dihydroxy-3-mercaptopropylthio)propanoyl, succinyl, acetyl, oxopentanoyl, carbamoyl, aminoalkyl, glutaramido, aminoethanethiol, mercaptopropanol, (hydroxypropylthio)propanoayl, 3-((2-propionamidoethyl)disulfanyl)-propanoayl, (((acetamidoethyl)disulfanyl)propanoyloxy)glutaramido, aminoethanethioate, and 2-hydroxyacetic proprionic anhydride; and providing a release agent, where the release agent causes the linker to degrade. The release agent may be an acid, light, hypoxia, or a catalyst.

In one aspect, the invention is a method of linking the central backbone to any of the three carrier groups via an amino acid linkage (alkylation or amidation process). The hydroxyl in the carrier groups may be activated by reacting it with disucccimidylcarbonate (DCS) or mesylate or tosylate or strong base (etherification or esterification).

Example of the synthesis of the PEG-carbohydrate conjugates from amino acids is shown below in Reaction Scheme 1. The reaction scheme is applicable to carrier groups having all kinds of hydrocarbon groups and amino acids with three available binding positions as demonstrated in the in Reaction Scheme 2 where the center backbone is serine.

The cholesteryl chloroformate is commercially available which may be directly reacted with an amino acid (AA) having a hydroxy group to produce a conjugate having an ester linkage. The carboxyl group of amino acid from Sterol-AA may react with the terminal hydroxy group of mPEG and then the protection group on the primary amine is removed and reacted with the activated carbohydrate to form the PEG-carbohydrate-sterol conjugates as depicted in Chemical Structure 4, where the sterol may be cholesterol. This reaction scheme is suitable for carrier groups with all kinds of lipophilic compounds or PEG chains. The general structures shown in the application are meant to include all racemers and structural isomers of the structures, as they may be functionally equivalent.

Reaction Scheme 1

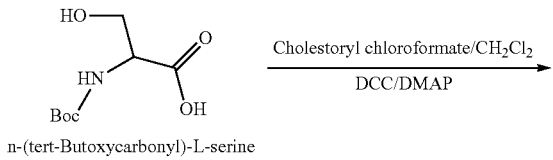

n-(tert-Butoxycarbonyl)-L-serine

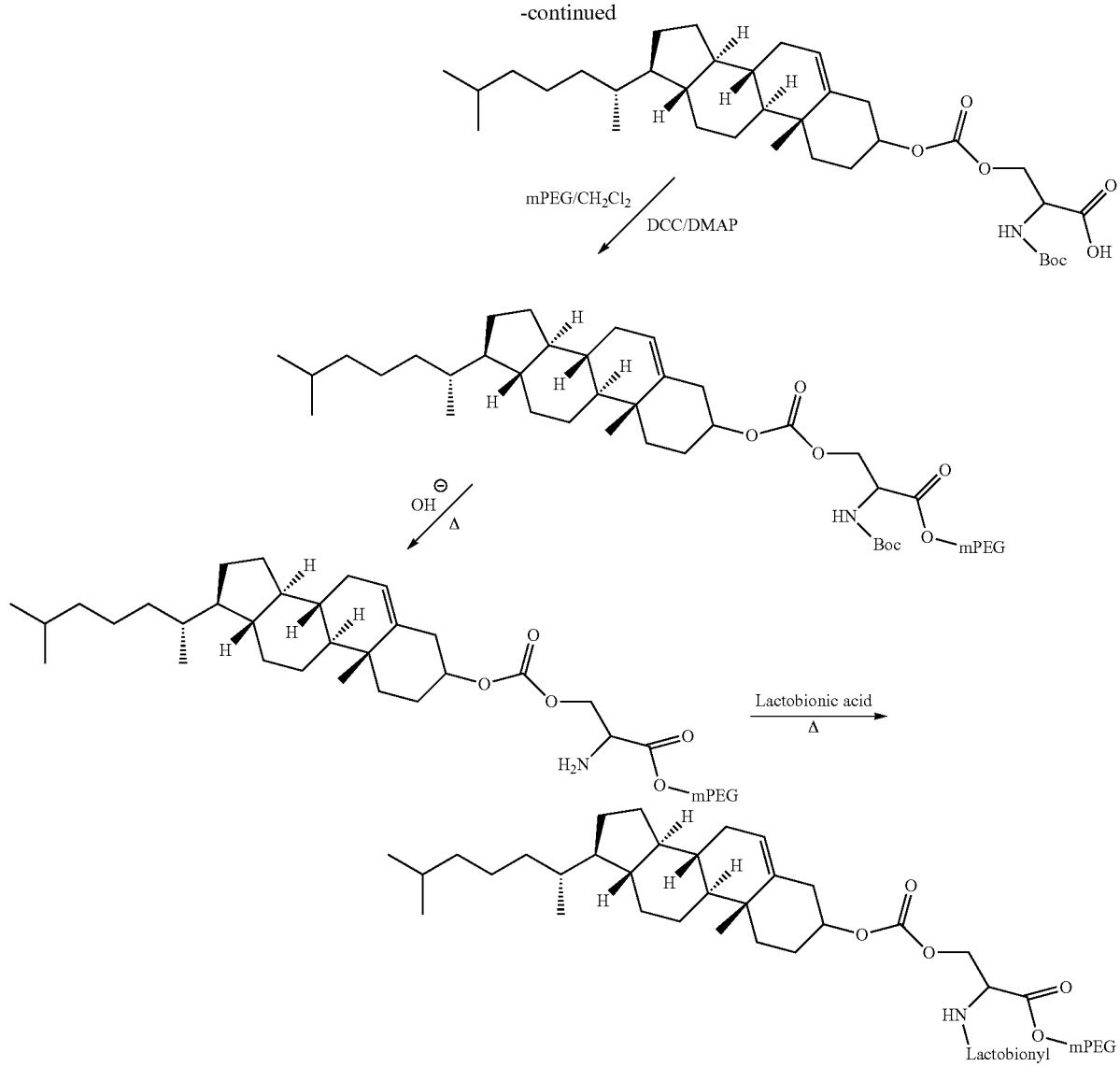
Chemical Structure 3: N-lactobionylserine-cholestryl-PEG$_{11}$
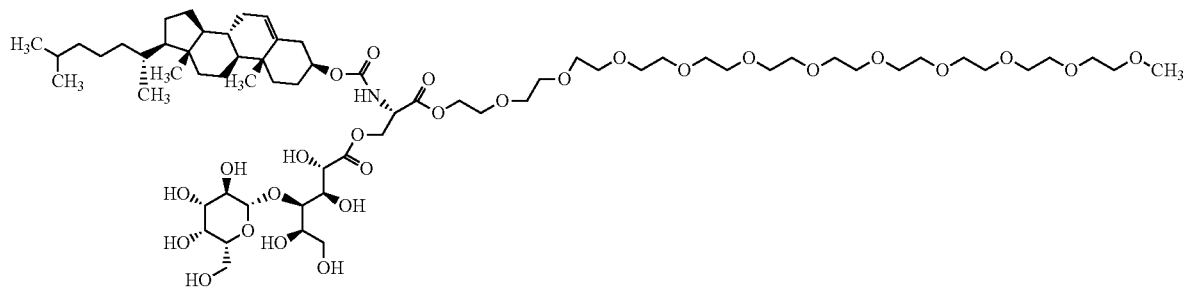

Example of the synthesis of the PEG-carbohydrate-sterol conjugates from glycerol or glycerol-like central backbones is shown below in Reaction Scheme 3. This reaction scheme is suitable for carrier groups with all kinds of lipophilic compounds or PEG chains.

Example of the synthesis of the PEG-carbohydrate-sterol conjugates from linear multiamine central backbones is shown below in Reaction Scheme 4. Again, this reaction scheme is suitable for amines or carrier groups with all kinds of lipophilic compounds or PEG chains or carbohydrates as demonstrated in Reaction Scheme 5.

As showed in the Reaction Scheme 6, O-acetylation procedures are one of the most common synthetic strategies for the protection and purification of various natural and synthetic carbohydrate substructures [G. Stork, T. Takahashi, I. Kawamoto, and T. Suzuki. *J. Am. Chem. Soc.* 100 (1978) 8272; A. P. Abbott, T. J. Bell, S. Handa, and B. Stoddart, *Green Chemistry,* 7 (2005) 705-707; M. Adinolfi, G. Barone, A. Iadonisi, and M. Schiattarella. *Tetrahedron Letters,* 44 (2003) 4661-4663]. The free hydroxide groups may react with acetic anhydride of acetic chloride in the presence of acid scavenger i.e. pyridine or Et3N, smoothly at room temperature overnight to form acetate ester (ROAc) in high yield. If catalytic amount of 4-Dimethylaminopyridine (~5%) was applied, the reaction was completed in less than 2 hours. The final product was further purified by washed with saturated NH$_4$Cl aqueous solution, followed by saturated NaHCO3 aqueous solution, dried over MgSO$_4$ or Na$_2$SO$_4$ and condensed. This reaction scheme is suitable for carbohydrates or sugar carrier groups with all kinds of lipophilic compounds or PEG chains or backbones.

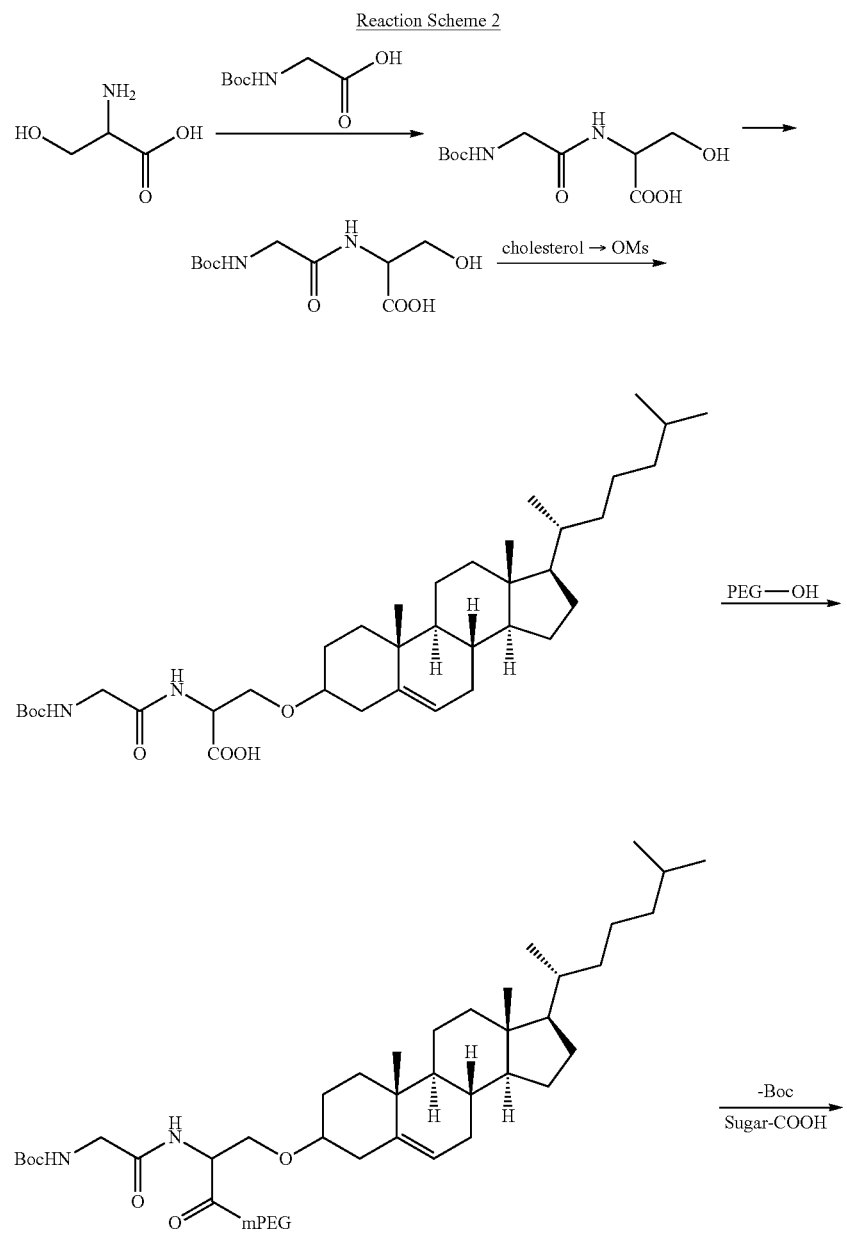

Reaction Scheme 2

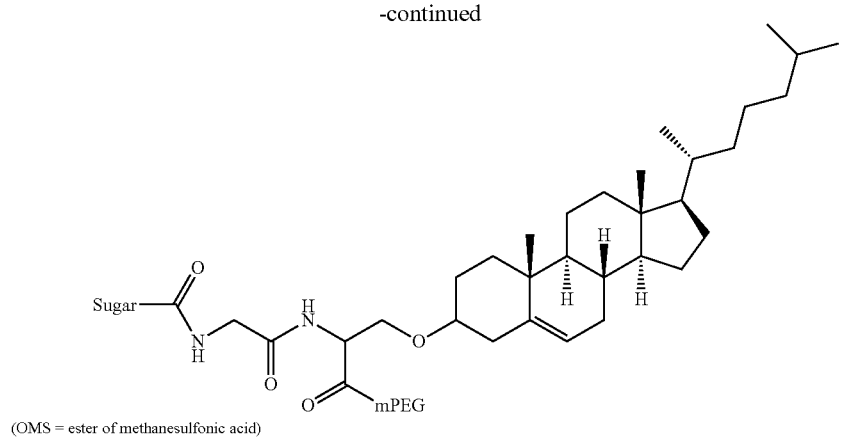
(OMS = ester of methanesulfonic acid)
Reaction Scheme 3
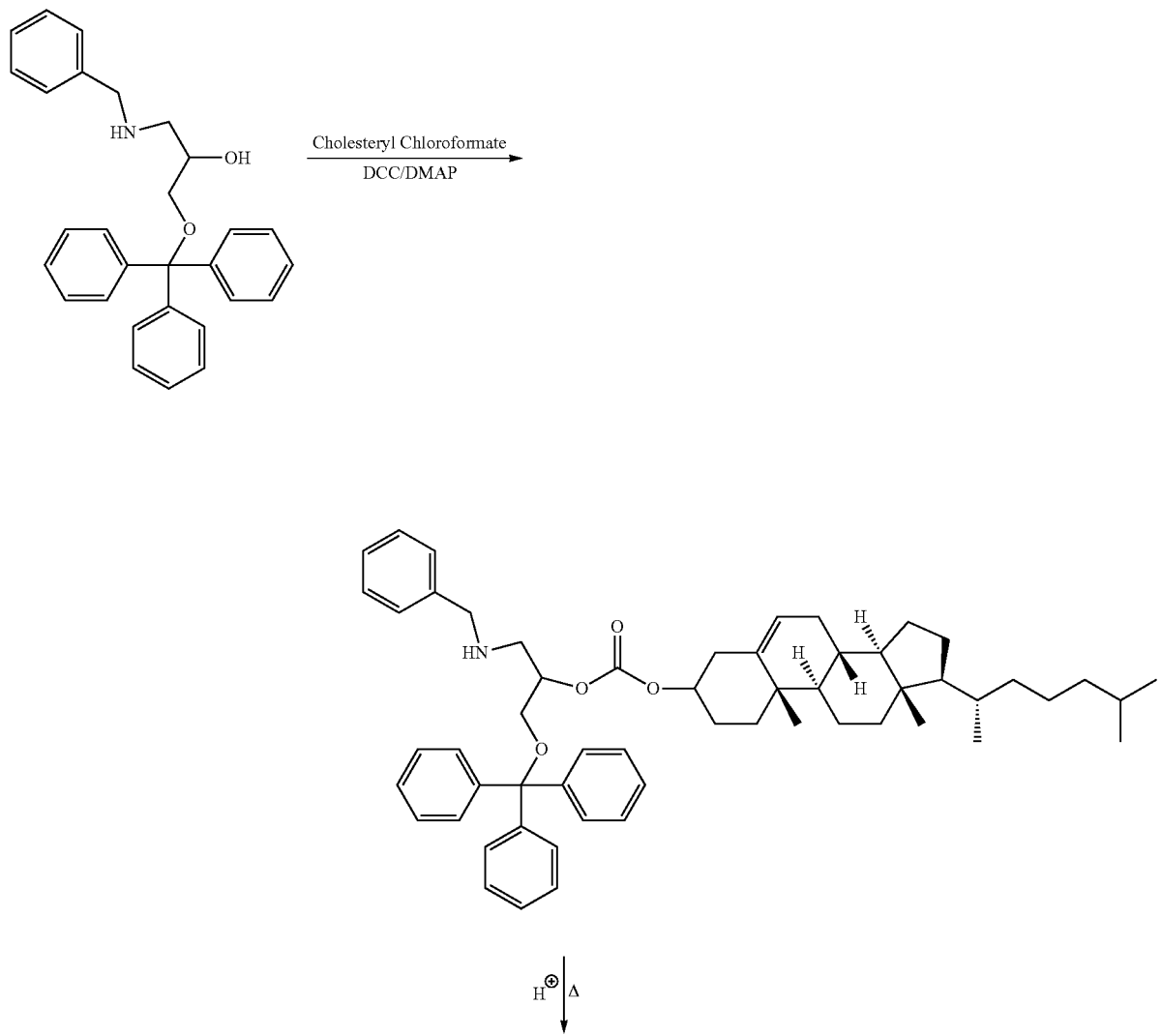

-continued
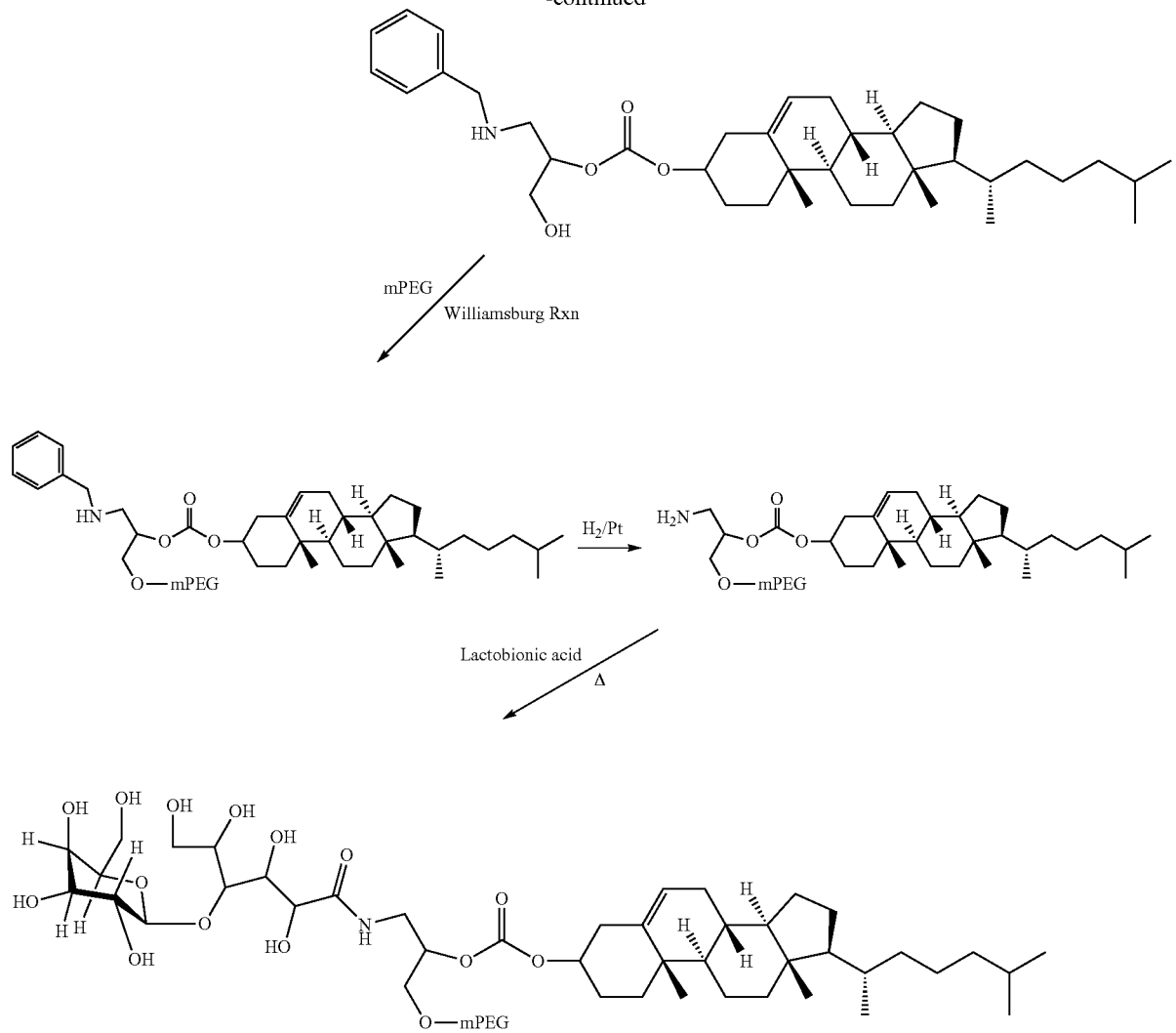
Reaction Scheme 4
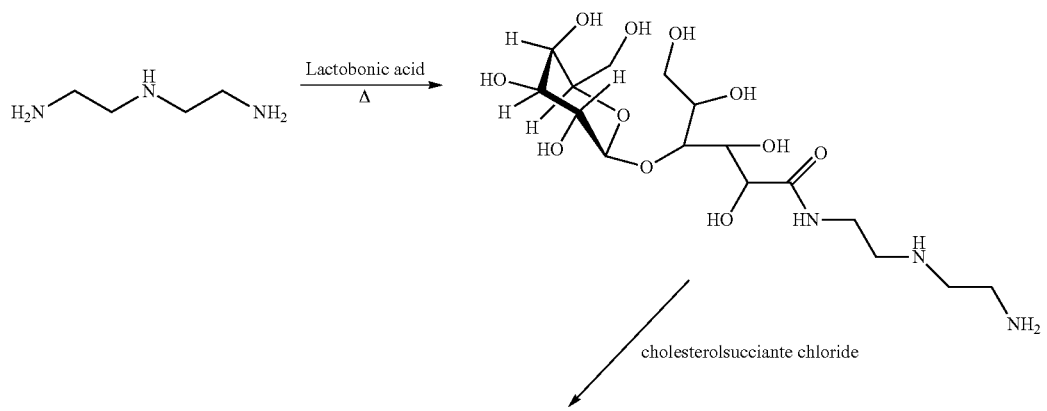
cholesterolsucciante chloride -continued
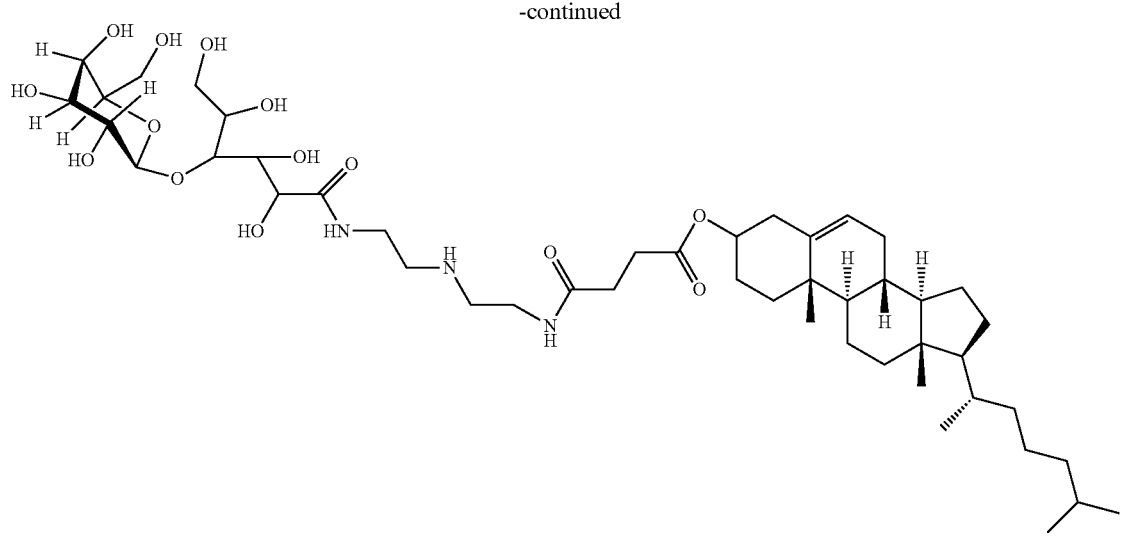
 mPEG (16)-carboxylic chloride
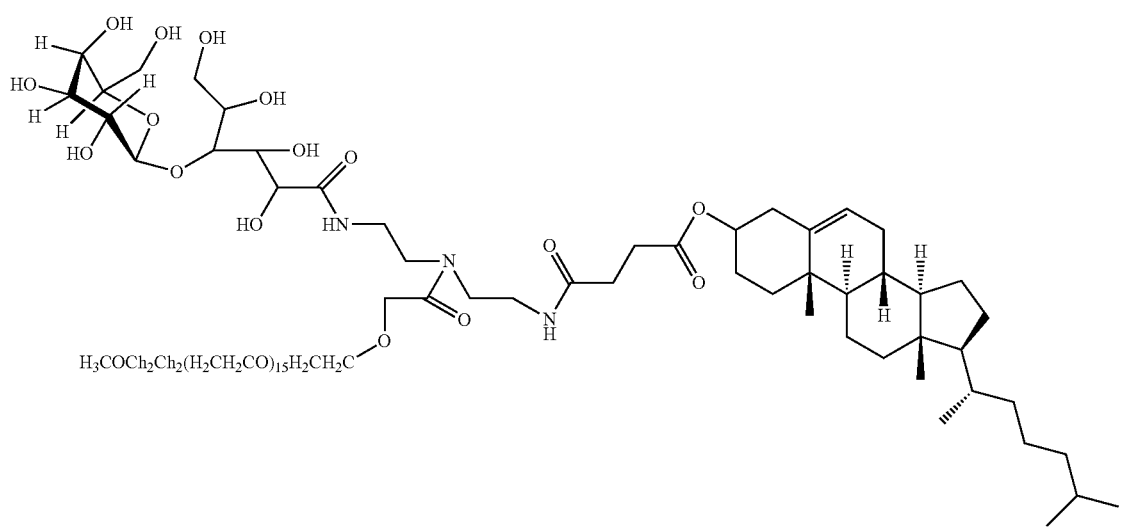
Reaction Scheme 5
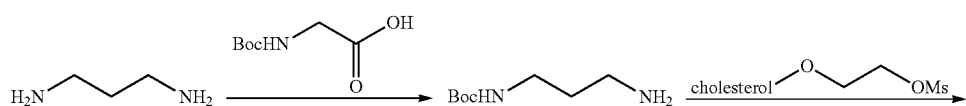

-continued
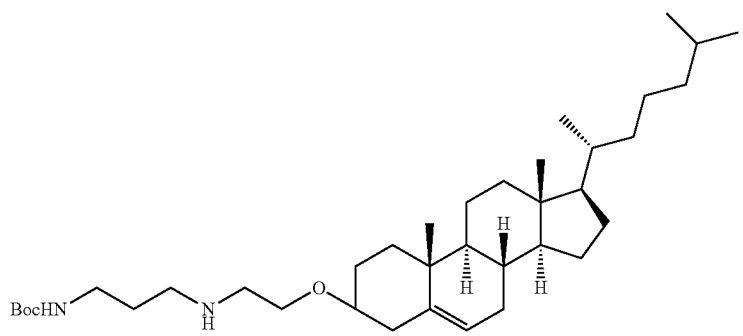
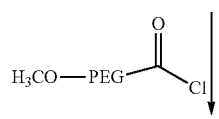
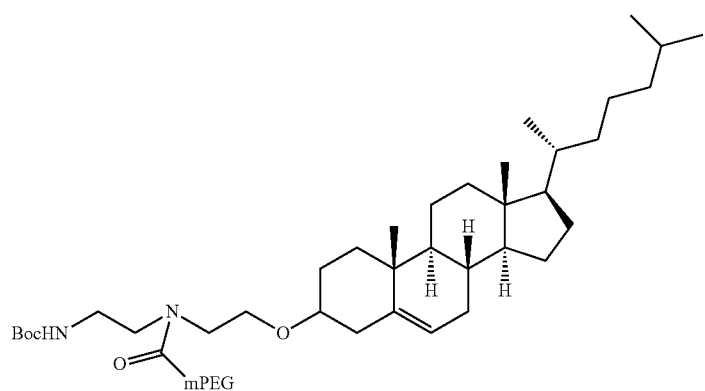
1) -Boc
2) +Sugar-COOH
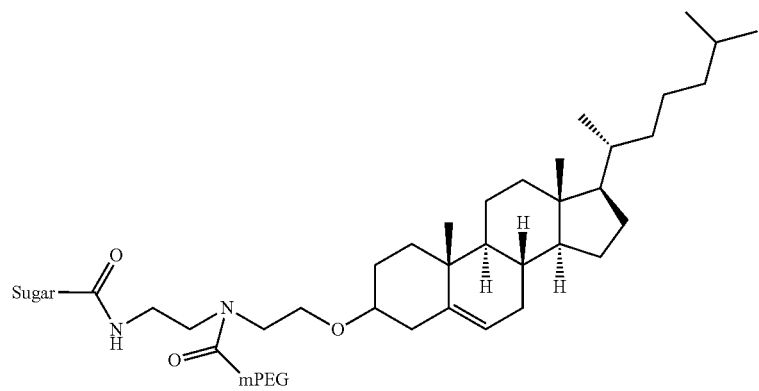

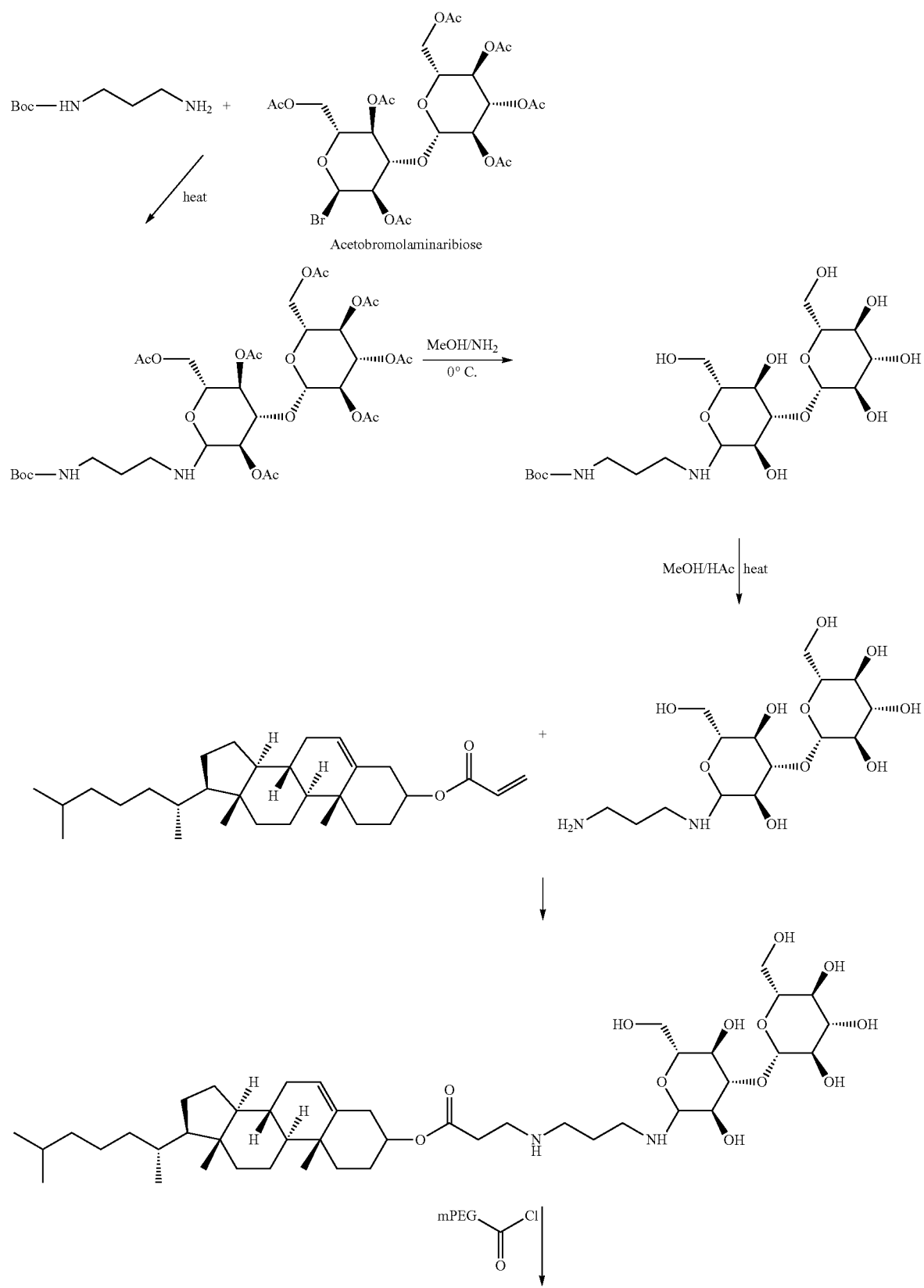
Reaction Scheme 6

-continued
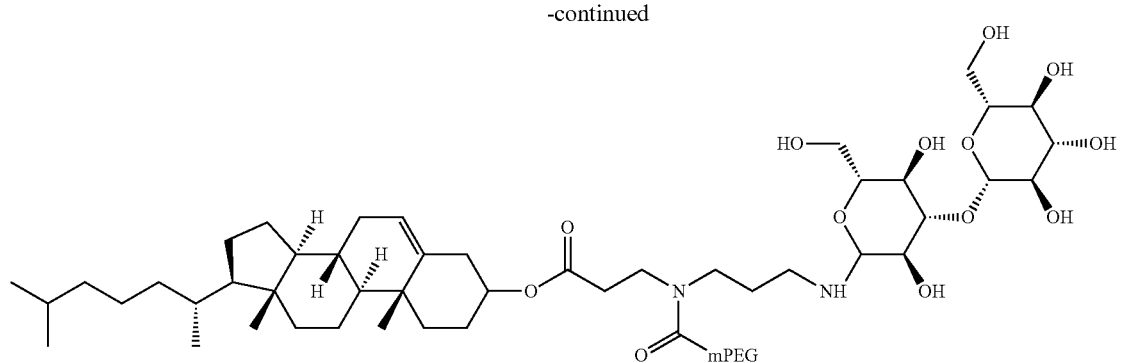
Reaction Scheme 7
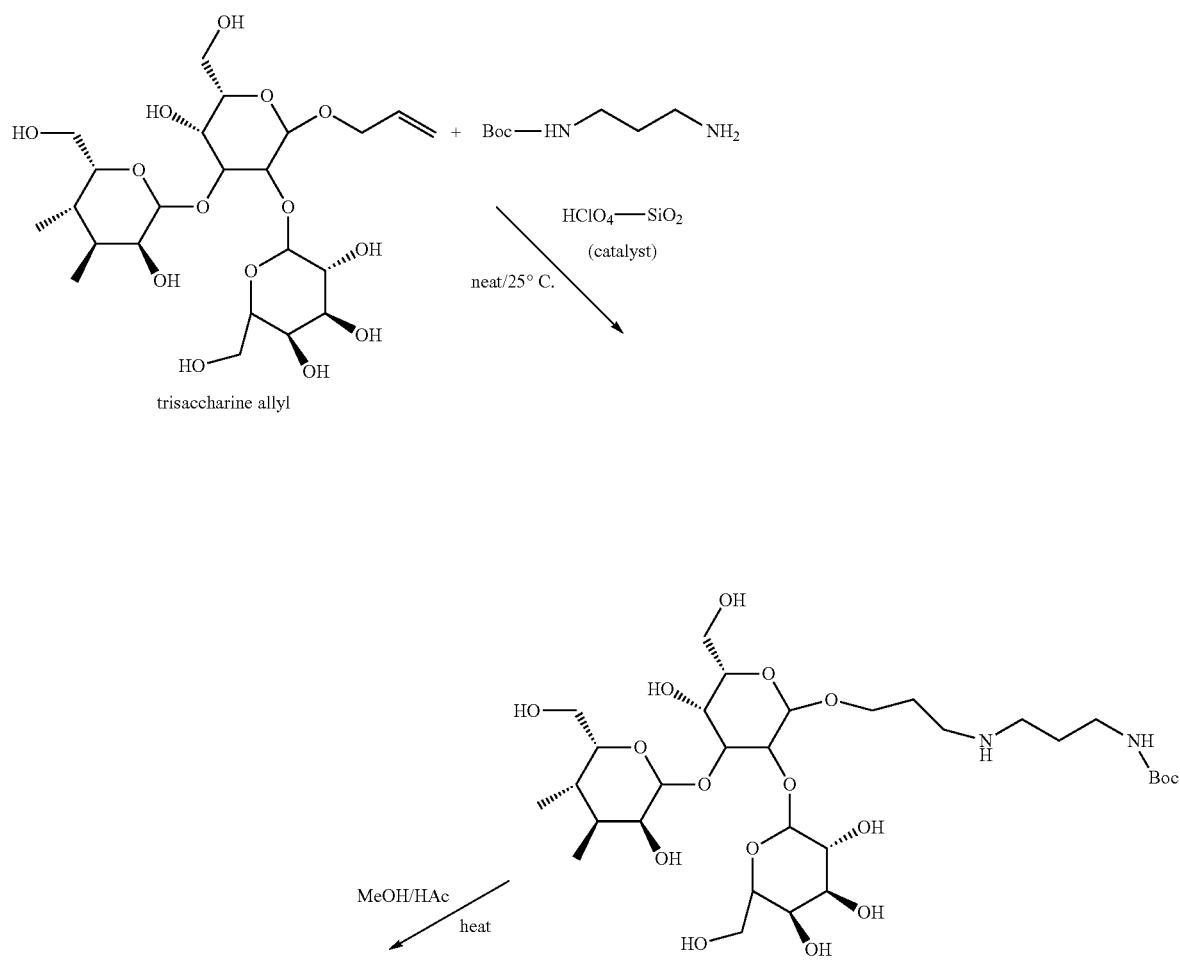

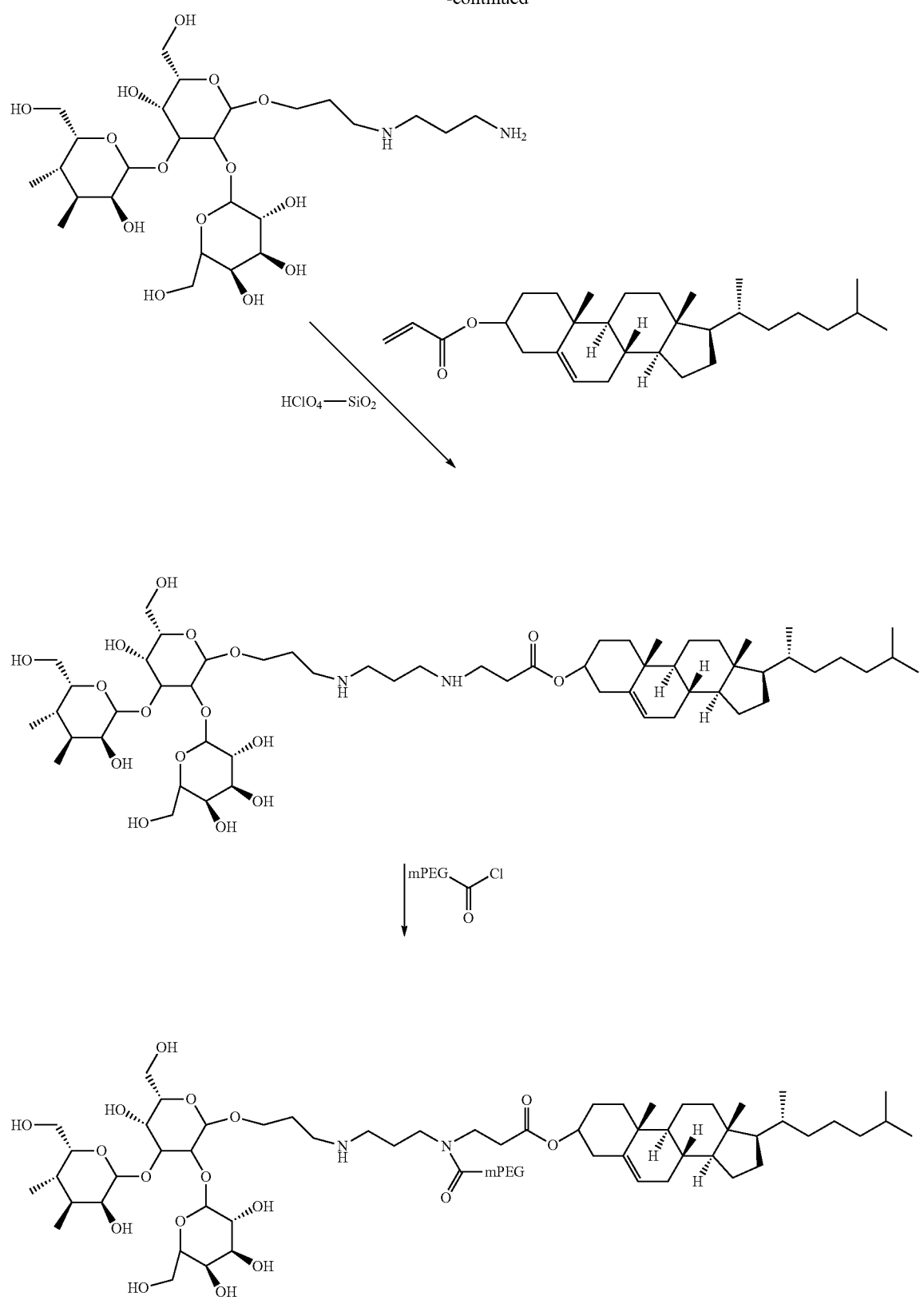

Reaction Scheme 8

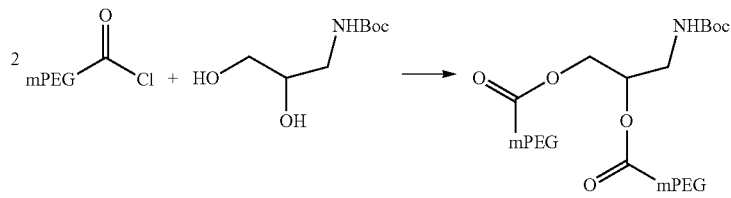

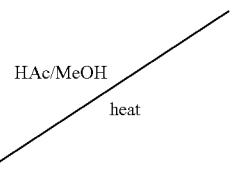

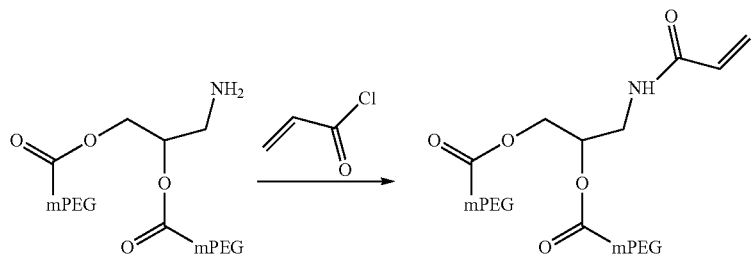

The present invention also demonstrated the using of a branched-PEG as the polymer carrier. Branched-PEGs are commercially available with relative large molecular weights. Thus branched PEGs with smaller PEG chains may be prepared according to the Reaction Scheme 8, consequentially. the activated branched PEG was used to make a branched PEG-carbohydrate conjugate as showed in the Reaction Scheme 9. As demonstrated in the Reaction Scheme 1 to 9, there are multiple chemical processes of alkylation, etherification, esterification or amidation involved for making each final product, the steps of each conjugation were designed accordingly.

Reaction Scheme 9

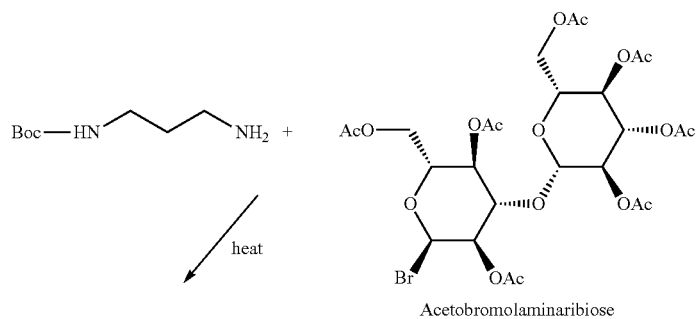

Acetobromolaminaribiose 55   56
-continued
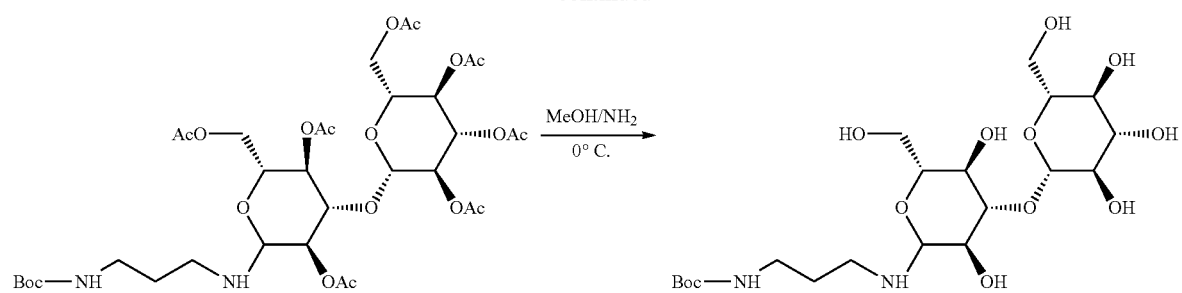
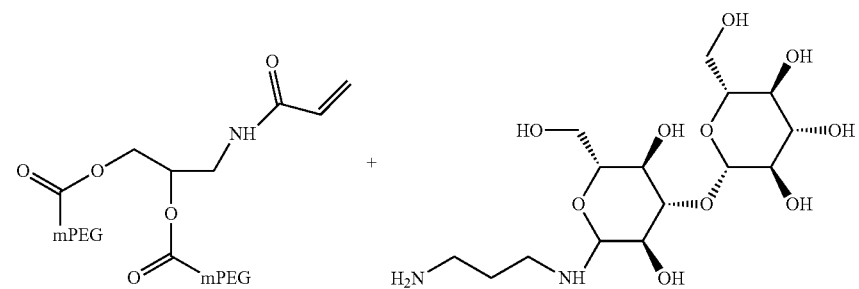
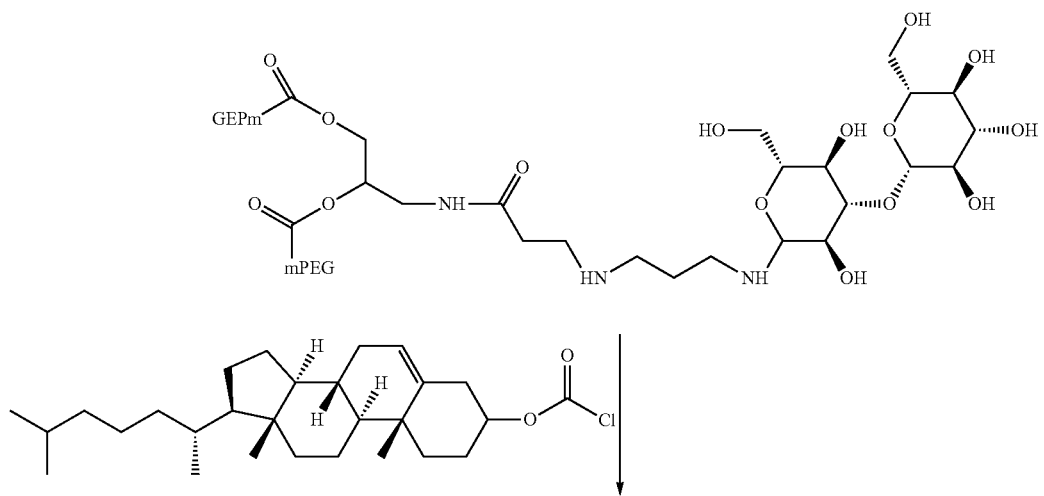

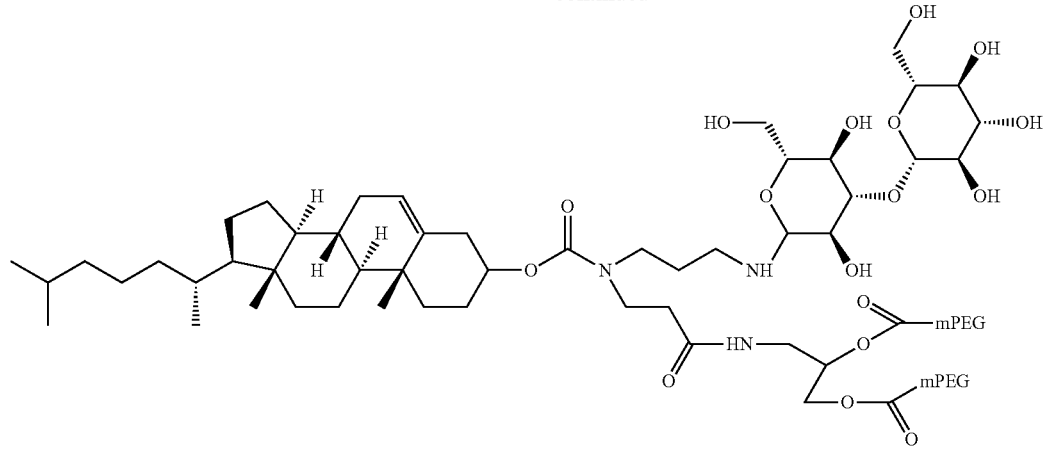

In another aspect, the invention includes PEG-carbohydrate conjugates comprised of three carrier groups and a central backbone having at three positions available for the conjugation, and one or more linker(s) between one of the carrier groups and the central backbone. Such PEG-carbohydrate conjugates are represented by the General Structures 1 to 15, where X may comprise a linker selected from Table 2 and 3 or a group consisting of amino, succinylamino, acetamido, aminopentanamido, aminoacetyl, acryloyl, thiopropanoayl, N-(mercaptomethyl)-propionamido, mercaptopropylthio)propanoyl, (1,2-dihydroxy-3-mercaptopropylthio)propanoyl, succinyl, acetyl, oxopentanoyl, carbamoyl, aminoalkyl, glutaramido, aminoethanethiol, mercaptopropanol, (hydroxypropylthio)propanoayl, 3-((2-propionamidoethyl)disulfanyl)-propanoayl, (((acetamido-ethyl)disulfanyl)propanoyloxy)glutaramido, amino-ethanethioate, and 2-hydroxyacetic proprionic anhydride. The Table 6 shows certain samples of the PEG-carbohydrate conjugates and in the event of variations of chemical names, the structures shown are meant to be controlling.

TABLE 6

Sample of PEG-Carbohydrate-Sterol Conjugates

| Name | Chemical Structure |
|---|---|
| CDL-mPEG: Cholesteryldiethylene-triaminemonomexyl-PEG lactobionate; n = 6 to 45. Conjugation via: esterification, etherification and amidation | |

TABLE 6-continued

Sample of PEG-Carbohydrate-Sterol Conjugates

| Name | Chemical Structure |
| --- | --- |
| CPL-mPEG: Cholesterylpropanediamine-monomexyl-PEG lactobionate; n = 6 to 45 Conjugation via: alkylation, esterification, etherification and amidation | 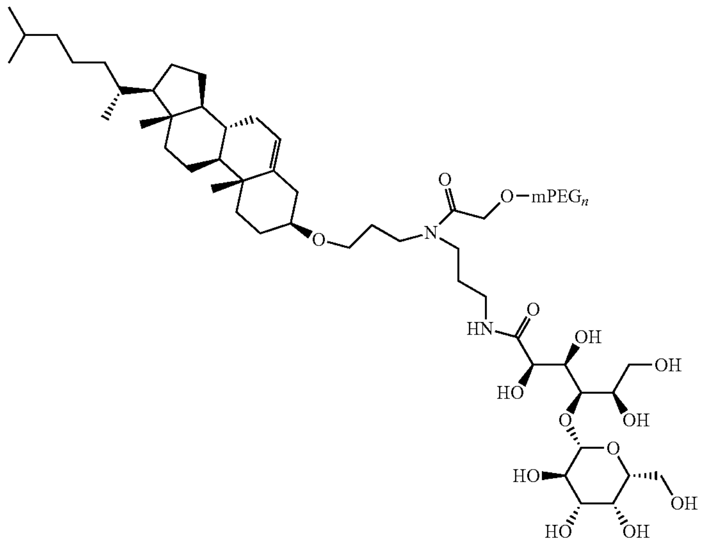 |
| CPG-mPEG: Cholesterylpropanediamine-monomexyl-PEG gluconate; n = 6 to 45 Conjugation via: alkylation, etherification and amidation | 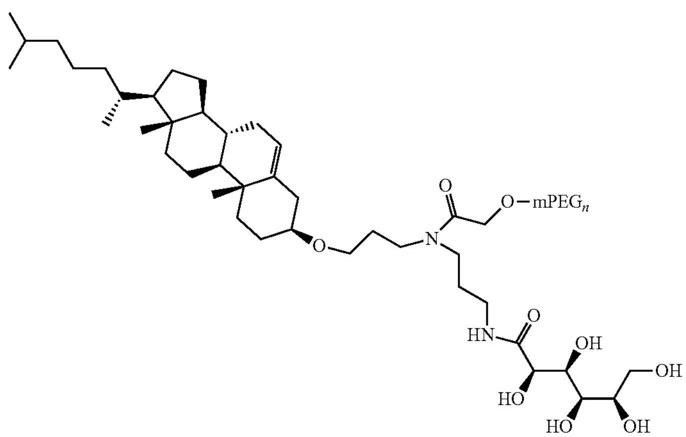 |
| CLL-mPEG: $^\varepsilon$N-Lactobionoyl-$^\alpha$N-cholesteryl-monomethoxyl PEG ether lysinate; n = 6 to 45. Conjugation via: etherification and amidation | |

TABLE 6-continued

Sample of PEG-Carbohydrate-Sterol Conjugates

| Name | Chemical Structure |
|---|---|
| CDG-mPEG: Cholesteryldiethylenetriamine-monomethoxyl polyethylene glycol ether glucuronate; n = 6 to 45. Conjugation via: alkylation, etherification and amidation | 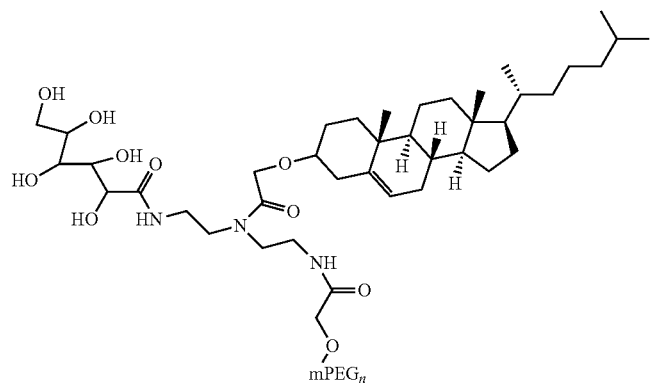 |
| TDL-mPEG: a-Tocopheryl diethylenetriamine-monomethoxyl polyethylene glycol ether lactobionate; n = 6 to 45. Conjugation via: alkylation, etherification and amidation | 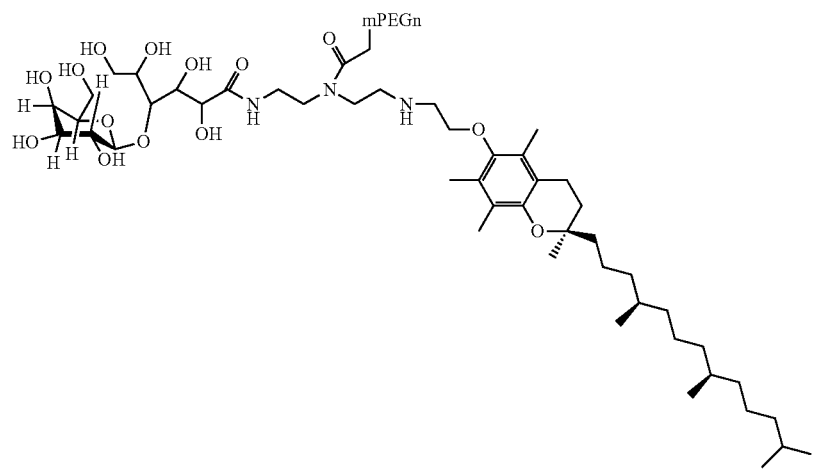 |
| TEL-mPEG: a-Tocopheryl ethylenediamine-monomethoxyl polyethylene glycol ether ascorbate; n = 6 to 45. Conjugation via: alkylation, etherification and amidation | 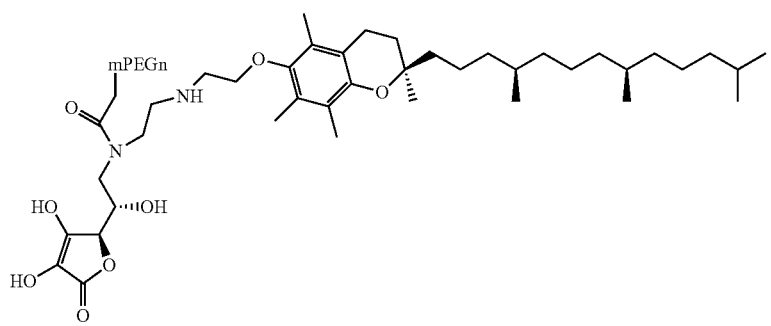 |
| ATES-mPEG: N-ascorboyl-a-Tocopheryl ethylenediamine-monomethoxyl polyethylene glycol ether aminosalicylate; n = 6 to 45. Conjugation via: alkylation, esterification and etherification | 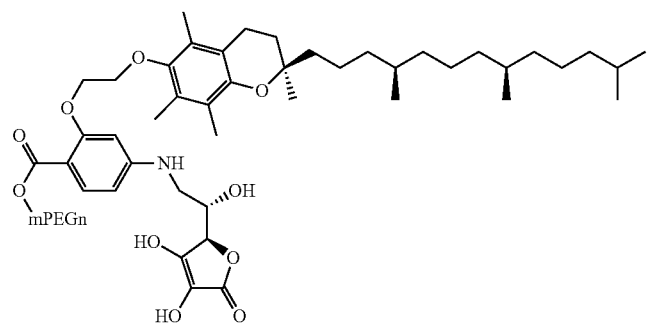 |

TABLE 6-continued

Sample of PEG-Carbohydrate-Sterol Conjugates

| Name | Chemical Structure |
| --- | --- |
| CFADL-mPEG: Cholecalciferolascorboyldiethylenetriamine-monomethoxyPEG ether lactobionate, n = 6 to 45. Conjugation via: alkylation, etherification and amidation | |
| CFDL-mPEG: Cholecalciferoladiethylenetriamine-monomethoxyPEG ether lactobionate, n = 6 to 45. Conjugation via: alkylation, etherification and amidation | |
| CDL-TrpPEG: Cholesteryldiethylenetriamine-tryptophanyl polyethylene glycol ether lactobionate; n = 6 to 45. Conjugation via: alkylation, esterification, etherification and amidation | |
| CPDL-mPEG: Cholesterol-mPEG-propanediamino-lactobionate, n = 6 to 45. Conjugation via: alkylation, esterification amidation | |

TABLE 6-continued

Sample of PEG-Carbohydrate-Sterol Conjugates

| Name | Chemical Structure |
|---|---|
| CPDA-mPEG: Cholesterol-mPEG-propanediamino-ascorbate, n = 6 to 45. Conjugation via: alkylation, esterification, etherification and amidation | 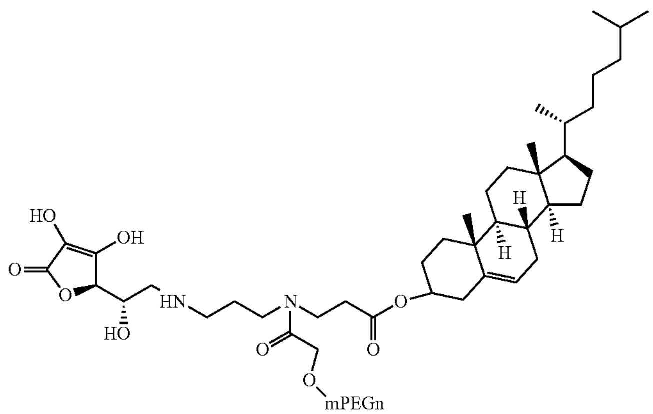 |
| CASPL-mPEG: N-cholesterolaspartate-mPEG lactobionate, n = 6 to 45. Conjugation via: alkylation, esterification, etherification and amidation | 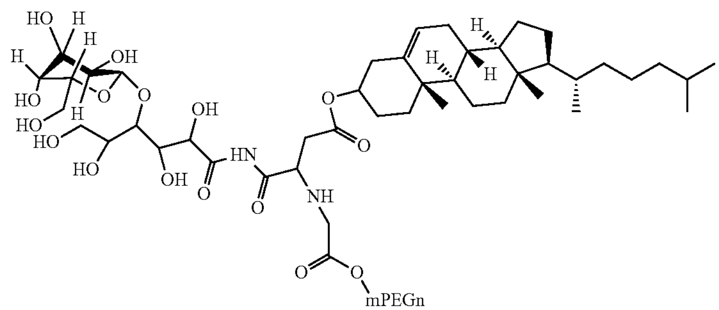 |
| CODL-mPEG: Cholesteryloleoyldi-ethylenetriamine-mPEG lactobionate, n = 6 to 45. Conjugation via: alkylation, esterification, etherification and amidation | 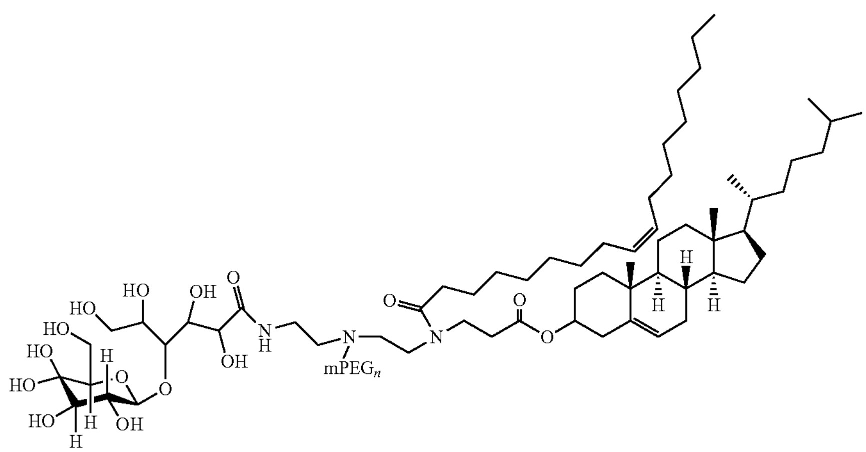 |
| CODL-mPEG: Cholesterylretinoyldi-ethylenetriamine-mPEG lactobionate, n = 6 to 45. Conjugation via: alkylation, esterification, etherification and amidation | |

TABLE 6-continued

Sample of PEG-Carbohydrate-Sterol Conjugates

| Name | Chemical Structure |
| --- | --- |
| CTL-bisPEG: Cholesteroltri-ethylenetetramine-bismonomethoxylPEG ether lactobionate, n = 6 to 45. Conjugation via: alkylation, esterification, etherification and amidation | 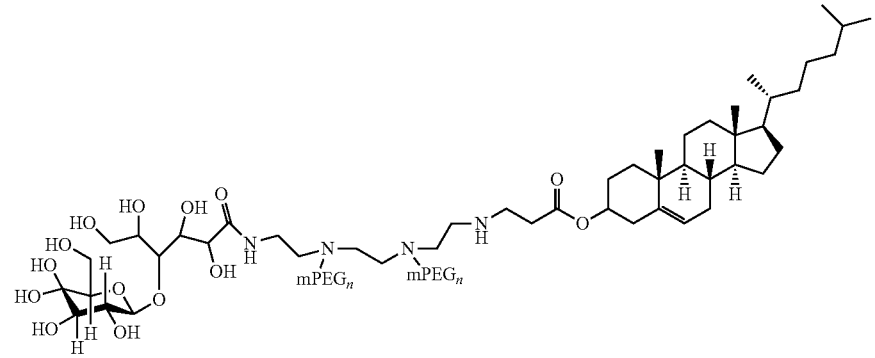 |
| LTL-mPEG: $^\varepsilon$N-Lactobionoyl-$^\alpha$N-a-tocopherol-monomethoxyl PEG ether lysinate; n = 6 to 45. Conjugation via: alkylation, esterification, etherification and amidation | 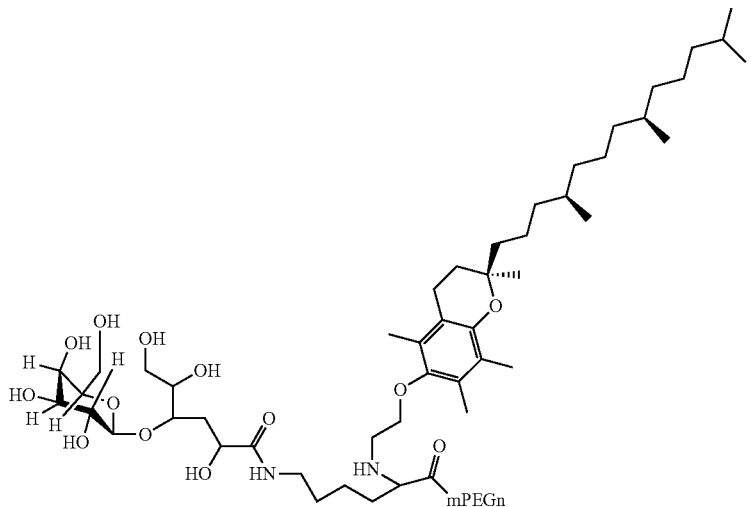 |
| TTL-bisPEG: a-tocopheroltriethylenetetramine-bismonomethoxyl-PEG ether lactobionate, n = 6 to 45. Conjugation via: alkylation, esterification, etherification and amidation | 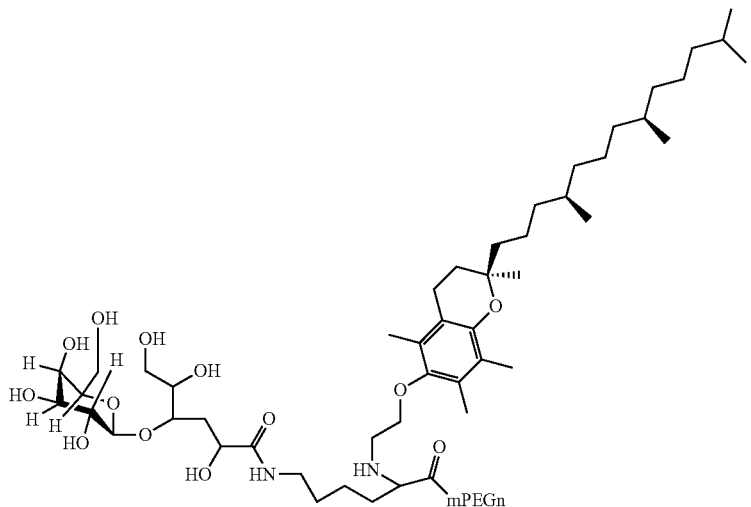 |

TABLE 6-continued

Sample of PEG-Carbohydrate-Sterol Conjugates

| Name | Chemical Structure |
|---|---|
| CADTL-mPEG: Cholesterolascorboyldi-ethylenetriamine-monomethoxyPEG ether lactobionate, n = 6 to 45. Conjugation via: alkylation, esterification, etherification and amidation | 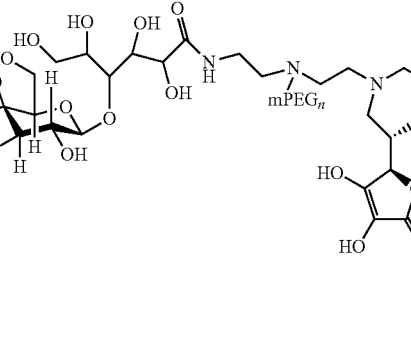 |
| BLDPCP-mPEG: N,N-1,3-bislactobionoyldiamino-2-propanol-cholesterol-monomethoxy-PEG-ether-propanediamine. n = 6 to 45. Conjugation via: alkylation, esterification, etherification and amidation | 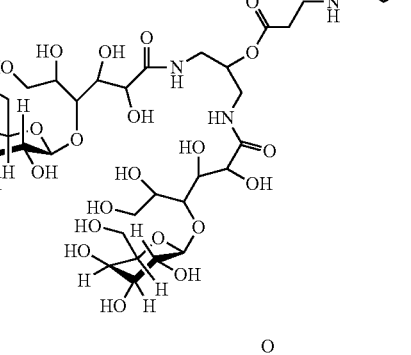 |
| Cholecalciferol-diethylene-triamineisomal-totriose-mPEG n = 6 to 45. Conjugation via: alkylation, esterification, etherification and amidation | 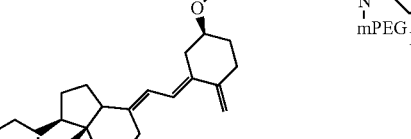 |

In Table 8 the types of coupling reaction between the carriers and the center backbone as well as any chemical modification of a carrier or center backbone prior to the conjugation are alkylation including N-alkylation or O-alkylation, esterification, etherification and amidation. For example, a monomethoxyl polyethylene glycol may be modified with acryloyl chloride then reacted with center backbone, thus two types of reaction may be involved; esterification and N-alkylation (Michael addition) as below (Reaction Scheme 10):

Reaction Scheme 10

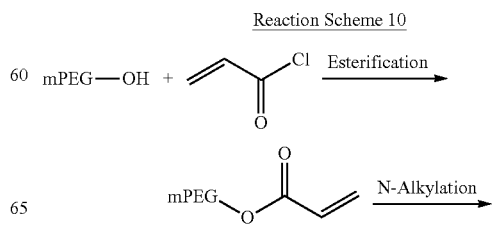

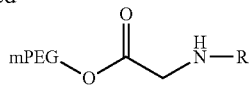

(R is a center backbone)

Embodiments of the present invention are described herein in the context of preparation of pharmaceutical compositions including polymer-carbohydrate conjugates or polymer-carbohydrate conjugates for increasing the solubility and enhancing the delivery of active agents. The approximate preferable compositions for formulated drug products are generally described herein, though different drugs typically have differing optimal formulations.

For IV solutions, the preferable concentration of drug is 0.1% to 30%. More preferable is 0.5 to 10%. Most preferable is 0.5 to 5%. The preferable weight ratio of PEG-carbohydrate conjugate (PC) to the drug (PC/drug) in the final drug solution for the injection is 1 to 30, w/v (weight/volume). More preferable is 1 (drug) to 25 (PC). Most preferable is 1 to 10.

It is preferable PEG-carbohydrate conjugates having marrow-disperse PEG chains for intravenous administration of pharmaceutical agents. The monodisperse PEG chains may consist of one or more PEG oligomers where the total oligomer purity from individual oligomers may be as high as 80%. For instance, a monodisperse PEG chain may contain 40% of PEG-12 and 40% of PEG-15. It is preferable to have a monodisperse PEG chain containing a few numbers of oligomers. The preferable number of oligomers is 1 to 20, more preferable is 1 to 10. Most preferable is 1 to 5.

For oral solutions, the preferable concentration of drug is 1% to 40%. More preferable is 2.5 to 30%. Most preferable is 5 to 30%. The preferable ratio of PEG-carbohydrate conjugates to the drug (PC/drug) is 0.5 to 25, w/v. More preferable is 1 (drug) to 20 (PC). Most preferable is 1 to 10.

For ophthalmic preparations, the preferable concentration of drug is 0.01 to 5%. More preferable is 0.05 to 2%. Most preferable is 0.1 to 2%. The preferable ratio of PEG-carbohydrate to the drug (PC/drug) is 1 to 30 w/w (weight/weight). More preferable is 3 (drug) to 20 (PC). Most preferable is 1 to 3.

For topical solutions, the preferable concentration of drug is 0.05 to 5%. More preferable is 0.1 to 5%. Most preferable is 0.1 to 2%. The preferable ratio of PEG-carbohydrate conjugates to the drug (PC/drug) is 1 to 30, w/v. More preferable is 3 (drug) to 20 (PC). Most preferable is 3 to 10.

For oral capsules, the preferable capsule content of drug is 2 mg to 500 mg. More preferable is 2 mg to 200 mg. Most preferable is 2 mg to 100 mg. The preferable ratio of PEG-carbohydrate conjugates to the drug (PC/drug) is 1 to 50, w/w. More preferable is 1 (drug) to 15 (PC). Most preferable is 1 to 5.

For topical preparations, the preferable concentration of active is 0.5 to 5%, more preferable is 0.5 to 2%, and most preferable is 1 to 2%. The preferable ratio of PEG-carbohydrate conjugates to the drug (PC/drug) is 1 to 30, w/w, more preferable is 1 (drug) to 20 (PC), most preferable is 3 to 10.

EXAMPLES

Chemicals and Reagents: N,N'-dicyclohexylurea, N,N'-dicyclohexylcarbo-diimide (DCC), ascorbic acid, lactobionic acid, cholecalciferol, cholesteryl chloroformate, cholesterol, glucuronic acid, polyethylene glycol (PEG), retinoic acid, α-tocopherol and other chemicals were obtained from Sigma-Aldrich (St. Louis, Mo., USA) or Alfa Aesar (Ward Hill, Mass., USA). Activated PEG or biotinylated PEG were obtained from Quanta BioDesign (Powell, Ohio, USA) or Thermo Fisher Scientific (Rockford, Ill.).

Example 1. Preparation of tert-Butyl Carbamates (Boc)-Protected Amino Groups

A high yield and effective synthetic method under a catalyst-free and room temperature was reported previously [Chankeshwara, S V and Chakraborti, A K. Org. Lett., (2006); 8, 3259] and used with slightly modification. To a solution of starting compound containing amino benzoate in MeOH, di-t-butyl dicarbonate was added as one to one molar ratio. The resulting mixture was stirred overnight at room temperature. When the reaction was done, solvent was removed under vacuum; the residue was dissolved into EtOAc and washed with saturated $NH_4Cl$ aqueous solution once, then dried over $Na_2SO_4$ and condensed to yield the expected product (>90%). Example of this reaction is demonstrated in Reaction Scheme 11, where R is a main structure of the central backbone. This method gives N-t-Boc derivatives chemoselectively without any side products (such as isocyanate, urea, N,N-di-t-Boc).

Reaction Scheme 11

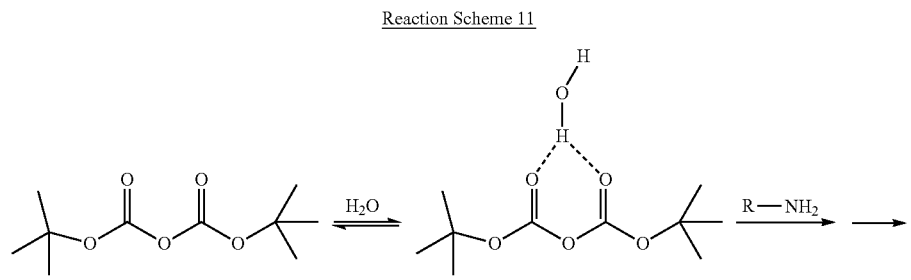

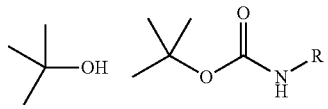

Example 2. Deprotection of Boc-Protected Amino Groups

Effective reagents for the deprotection of tert-butyl carbamates or tert-butyl esters include phosphoric acid and trifluoroacetic acid. The reactions give high yields and very convenient [Li, B. Berliner, M. etc, *J. Org. Chem.*, 2006; 71, 9045]. Equal volumes of trifluoroacetic acid were added to a solution of Boc-carbamate (10% of crude product) in $CH_2Cl_2$. The resulting solution was stirred at room temperature for overnight and the solvent was evaporated and the residue was redissolved into $CH_2Cl_2$, then washed with saturated $NaHCO_3$ and dried over $MgSO_4$. Solvent was evaporated and was used in next step without further purification.

Example 3. Preparation of N-Boc-cholesterylserinate 0.03 moles of N-Boc-serine was constantly stirred under nitrogen in 100 mL of chloroform. 0.03 mole of cholesteryl chloroformate was dissolved with 100 mL of chloroform and added to this heterogeneous mixture of N-tert-butyloxycarbonylserine and followed by adding 10 mL of anhydrous pyridine. The reaction for 30 minutes under constantly stirring at room temperature, the mixture turned to homogeneous and the reaction was completed when no detectable cholesteryl chloroformate was in the mixture. The bulk solvent was removed under vacuum and the crude product was used to next step without further purification. The resulting product (% of yields 70-80) is showed in Chemical Structure 5.

Chemical Structure 5

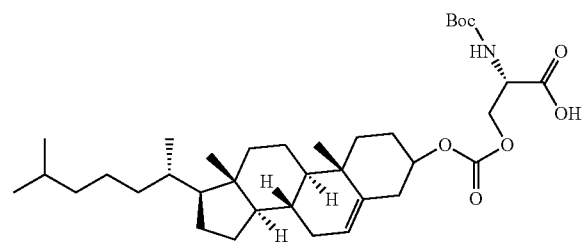

Example 4. Preparation of N-Boc-cholesterylmonomethoxyldodecaethylene Glycol Ether Serinate 0.01 moles of monomethoxyldodecaethylene glycol ether (0.01 mmol) was dissolved with 50 mL of anhydrous $CH_2Cl_2$, 0.01 mole of dicyclohexylcarbodiimide and cholesterylserinate were added. The resulting mixture was stirred at 0° C. for 2 hours, then allowed to warm up to room temperature and stirred for additional 48 hours. When the reaction was complete, the white precipitate was filtered off over celite. The residue was rinsed with small amount of $CH_2Cl_2$ twice and washed with sutured $NH_4Cl$, then dried over $MgSO_4$. Solvent was evaporated to afford pale yellowish oil as showed in Chemical Structure 6. The crude product's purity was determined by $^1H$ NMR and UPLC-MS, ESI-MS (>70%).

Chemical Structure 6

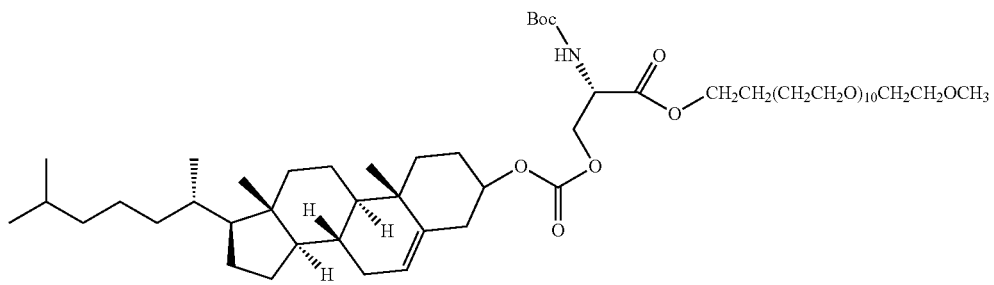

Example 5. Preparation of Cholesterylserinylmonomethoxyldodecaethylene-glycol Ether Lactobionate The protection group of tert-butylcarbonyl on the amino group was removed according to the method described in Example 2. 0.01 moles of N-Boc-cholesterylserinylmonomethoxyldodecaethylene glycol ether (0.01 mmol) front Example 4 was dissolved with 50 mL of anhydrous N-methyl-2-pyrrolidinone, 0.01 moles of Lactobionolactone was added. The resulting mixture was stirred at 50-60° C. for overnight, and allowed to cool to the room temperature. The reaction solution was precipitated into isopropyl alcohol (IPA) and methyl t-butyl ether (MTBE) was added to maximize the isolated yield of precipitate. The crude product was washed well with 50/50 (v/v) IPA/MTBE and dried under vacuum at 30-40° C. The purity (>90%) of the final product (Chemical Structure 7) was determined by $^1H$ NMR and UPLC-MS.

Chemical Structure 7

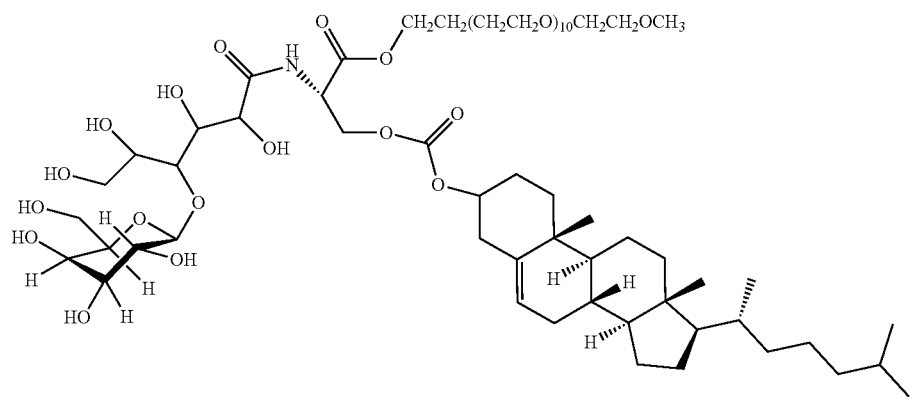

Example 6. Preparation of Lactobionyldiethylenetriamine

Diethylenetriamine (0.01 mol) was dissolved in 50 mL of dry (molecular sieve) N-methyl-2-pyrrolidinone and lactobionolactone (0.005 mol) was added. The resulting mixture was stirred for 6 hours at 50-60° C. and allowed to cool to the room temperature when the reaction was completed. The reaction solution was precipitated into isopropyl alcohol (IPA) and methyl t-butyl ether (MTBE) was added to maximize the isolated yield of precipitate. The cake was washed well with 50/50 (v/v) IPA/MTBE and dried under vacuum at 30-40° C. The crude product (Chemical Structure 8) and was used in next step without further purification.

Chemical Structure 8

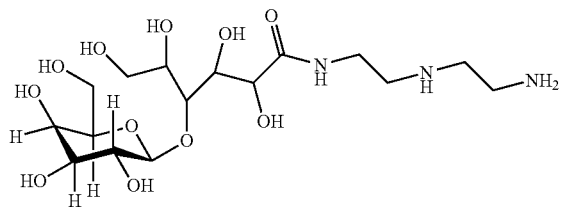

Example 7. Preparation of Lactobionylcholesteryldiethylenetriamine-mPEG 0.01 mole of the starting material from Example 6, lactobionyldiethylenetriamine, was dissolved in 20 mL of dimethylformamide (DMF) at 20 to 30° C. The slightly excess active oleic acid N-hydroxysuccinimide ester (0.011 mol) was dissolved in 20 mL of tetrahydrofuran (THF), then mixed with lactobionyldiethylenetriamine and adding triethylamine (TEA, 3%, v/v) as a base, stirred for 2 hrs at room temperature. An assay was performed to verify the yield and moves to next step without purification. The active mPEG$_{24}$-NHS (0.01 mol) was dissolved in DMF, and then mixed with the above reactants, stirred for overnight at room temperature. After the completion of the reaction, solvents were removed by vacuo and 50 mL of acetone was added to the crude product and filtered and washed with 30 mL of acetone three times. The reaction solution was precipitated into isopropyl alcohol (IPA) and methyl t-butyl ether (MTBE) was added to maximize the isolated yield of precipitate. The crude product was washed well with 50/50 (v/v) IPA/MTBE and dried under vacuum at 30-40° C. The purity (>95%) of the final product (Chemical Structure 9) was determined by $^1$H NMR and UPLC-MS.

Chemical structure 9

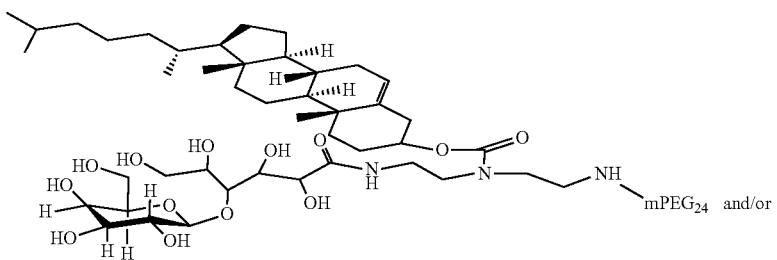

-continued

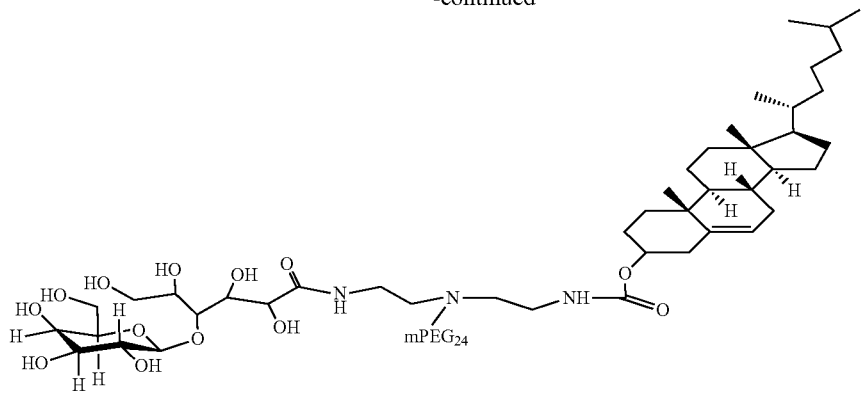

Example 8. Preparation of Lactobionyltriethylenetetramine

Triethylenetetramine (0.01 mol) was dissolved in 50 mL of dry (molecular sieve) N,N-Dimethylformamide (DMF) and lactobionic acid (0.01 mol) was added. The resulting mixture was stirred for 6 hours at 50-60° C. and allowed to cool to the room temperature when the reaction was completed. The reaction solution was precipitated into isopropyl alcohol (IPA) and methyl t-butyl ether (MTBE) was added to maximize the isolated yield of precipitate. The cake was washed well with acetone, then 50/50 (v/v) IPA/MTBE and dried under vacuum at 30-40° C. The crude product (Chemical Structure 10) was used in next step without further purification.

Chemical Structure 10

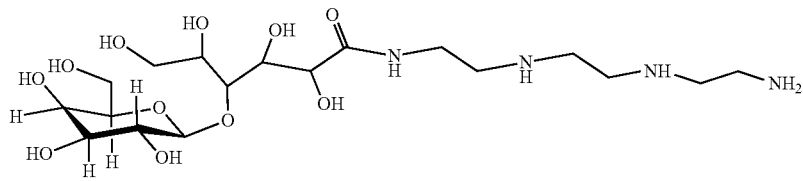

Example 9. Preparation of Lactobionylcholesteryltriethylenetetramine 0.01 mole of lactobionyltrethylenetetramine from Example 8 was dissolved with 50 mL of anhydrous N-methyl-2-pyrrolidinone, 0.01 moles of cholesteryl chloroformate was added. The resulting mixture was stirred at 45-50° C. for overnight, and allowed to cool to the room temperature. The reaction solution was precipitated into isopropyl alcohol (IPA) and methyl t-butyl ether (MTBE) was added to maximize the isolated yield of precipitate. The crude product was washed well with 50/50 (v/v) IPA/MTBE and dried under vacuum at 30-40° C. The purity (>80%) of the final product (Chemical Structure 11) was determined by $^1$H NMR and UPLC-MS.

Chemical Structure 11

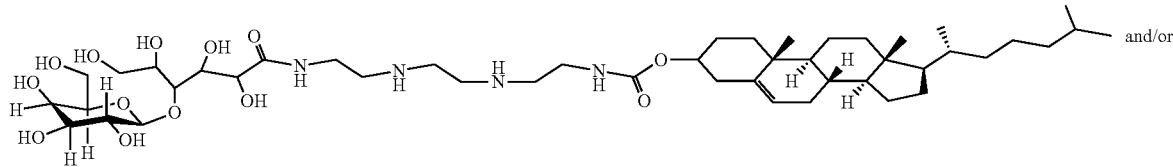

and/or

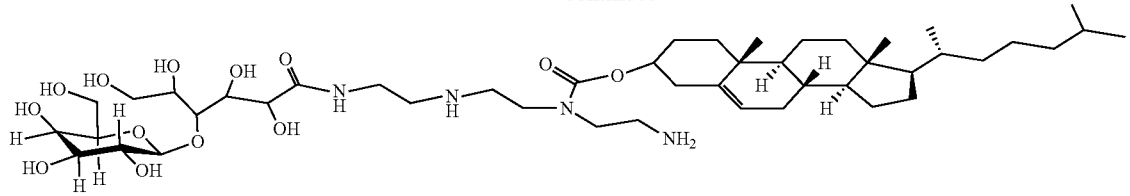

Example 10. Preparation of Lactobionylretinoyltriethylenetetramine-mPEG 0.01 mole of the starting material from Example 9, lactobionylcholesteryltriethylenetetramine, was dissolved in 20 mL of dimethylformamide (DMF) at 20 to 30° C., a slightly excess of the active mPEG$_{24}$-NHS (0.021 mol in 10 mL DMF) was added, stirred for overnight at room temperature. 300 mL of acetone was added at the end of the reaction and solvents were removed by vacuo. The crude product washed with acetone and filtered. The wet product (60-65%) was further lyophilized to a wax as showed in Chemical Structure 12.

Example 12. Preparation of Cholesteryl Ethylylene Glycol Acetic Acid

Product of cholesteryl ethylylene glycol ether from Example 11 (0.02 mol) in tetrahydrofuran (100 mL) was placed into a round-bottomed flask equipped with a mechanic stirrer and a heating mantle. The solution was sparged with nitrogen (50-100 psi). Sodium strip (0.05 g) is added slowly at ambient room temperature. After the addition was completed, the reaction mixture was heated up gradually to 60° C. under constant stirring for 6 hours and sodium chloroacetate (0.03 mol) and NaI (0.005 mol) was added into the reaction flask and the reaction mixture was allowed to continue at 55-60° C. under constant stirring overnight. The reaction was quenched with sodium hydroxide solution (100 mL of 5%, w/v) and concentrated by remove tetrahydrofuran under vacuo, then extracted with methylene chloride (50 mL). The aqueous layer was acidified with HCl (36%) to pH 3-4. The aqueous phase was extracted with methylene chloride (25 mL) twice. The combined organic layers were dried over sodium sulfate for 1 hour. The salt was removed by paper filtration and the solvent was removed in vacuo to yield an oil products (45-73%) as showed in Chemical Structure 14.

Chemical Structure 12

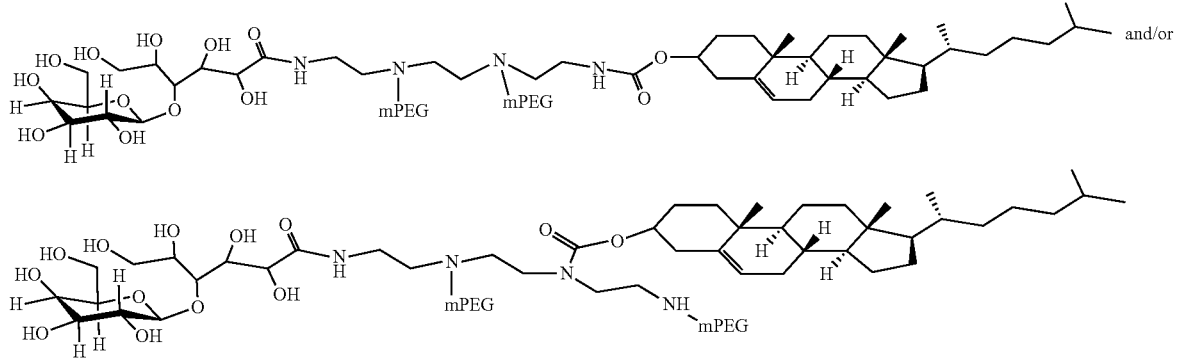

Example 11. Preparation of Cholesteryl Ethylylene Glycol Ether

Cholesteryl tosylate (0.1 mol) in tetrahydrofuran (100 mL) was mixed with ethylene glycol (1 mol) a round-bottomed flask equipped with a mechanic stirrer and heating mantle. The reaction mixture was stirred under reflux for 12 hours under protection of nitrogen and solvent was removed in vacuo, the residual was redissolved in 200 mL of methylene chloride and washed with 200 mL of water three times. The crude product in methylene chloride was dried in vacuo to yield a solid (90-105%) as showed Chemical Structure 13.

Chemical Structure 13

Chemical Structure 14

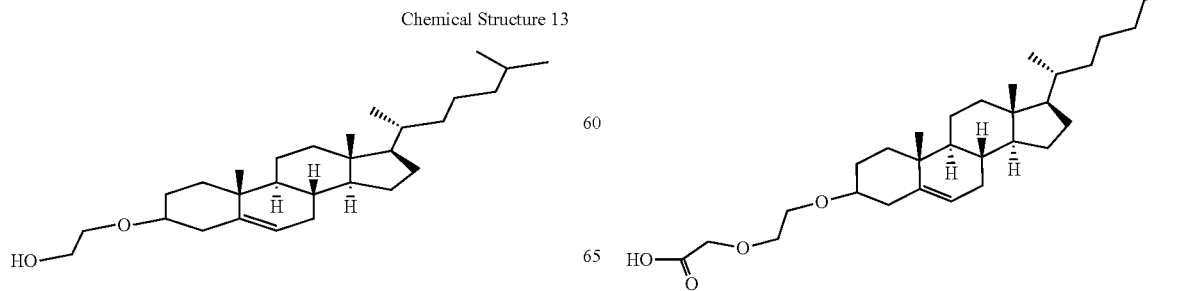

Example 13. Preparation of Lactobionyldiaminepropane 1,3-diaminepropane (0.01 mol) was dissolved in 50 mL of dry (molecular sieve) N-methyl-2-pyrrolidinone and lactobionolactone (0.005 mol) was added. The resulting mixture was stirred for 6 hours at 50-60° C. and allowed to cool to the room temperature when the reaction was completed. The reaction solution was precipitated into isopropyl alcohol (IPA) and methyl t-butyl ether (MTBE) was added to maximize the isolated yield of precipitate. The cake was washed well with 50/50 (v/v) IPA/MTBE and dried under vacuum at 30-40° C. The crude product (Chemical Structure 15) was used in next step without further purification.

Chemical Structure 15

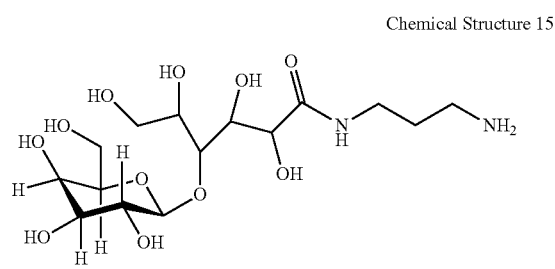

Example 14. Preparation of Lactobionyldiaminepropanyl-mPEG 0.01 mole of the starting material from Example 14, lactobionyldiaminepropane, was dissolved in 20 mL of dimethylformamide (DMF) at 20 to 30° C. The active mPEG$_{24}$-NHS (0.01 mol) was dissolved in DMF, and then mixed with the above reactants, stirred for overnight at room temperature. After the completion of the reaction, solvents were removed by vacuo and 50 mL of acetone was added to the crude product and filtered and washed with 30 mL of acetone three times. The wet product (60-70%) was further lyophilized to a wax as showed in Chemical Structure 16.

Chemical structure 16

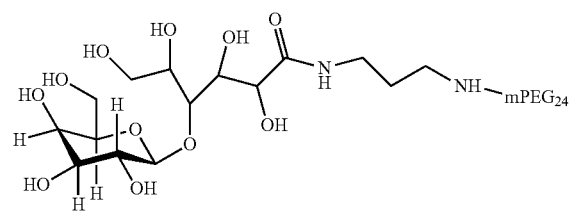

Example 15. Preparation of Lactobionylcholesteryldiaminepropyl-mPEG 0.01 moles of lactobionyldiethylenetriamine-mPEG (0.01 mmol) from Example 14 was dissolved with 50 mL of anhydrous N-methyl-2-pyrrolidinone, cholesteryl ethylylene glycol acetic acid (0.01 mole) from Example 13 in tetrahydrofuran (50 mL) and slightly excess active N-hydroxysuccinimide ester (0.011 mol) dissolved in 20 mL of tetrahydrofuran (THF) were mixed with of lactobionyldiethylenetriamine-mPEG and adding triethylamine (TEA, 3%, v/v) as a base, stirred for 2 hrs at room temperature. Assays were performed to verify the yield periodically. The resulting mixture was stirred at 45-50° C. for overnight, and allowed to cool to the room temperature. The reaction solution was precipitated into isopropyl alcohol (IPA) and methyl t-butyl ether (MTBE) was added to maximize the isolated yield of precipitate. The crude product was washed well with 50/50 (v/v) IPA/MTBE and dried under vacuum at 30-40° C. The purity (>93%) of the final product (Chemical Structure 17) was determined by $^1$H NMR and UPLC-MS.

Chemical structure 17

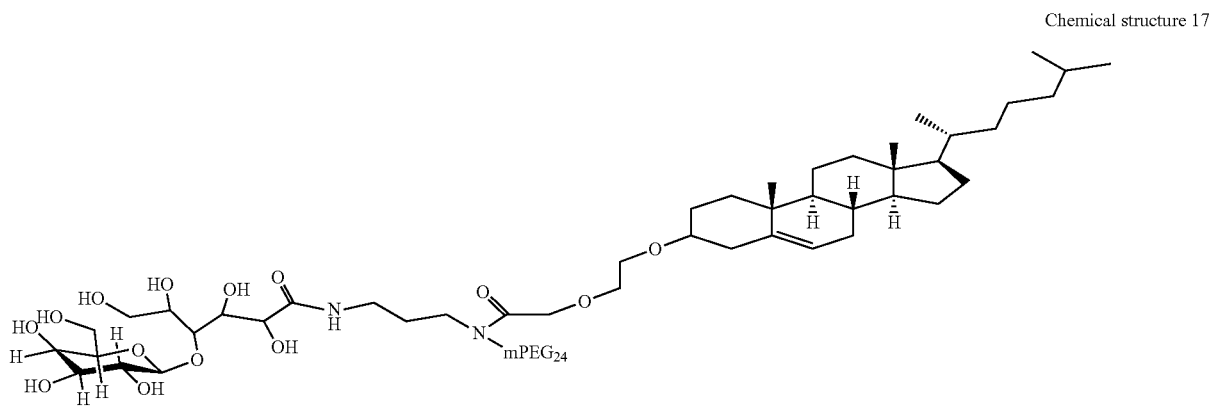

Example 16. Preparation of Boc-Glycinylserinate (Boc-Gly-Ser)

Boc-Glycine (0.1 mol) and N,N'-Dicyclohexylcarbodiimide (0.1 mol) in methylene chloride (50 mL) was stirred for 30 minutes, and the mixture was added into a methylene chloride solution (50 mL) of (0.1 mol) slowly. The mixture was stirred for 2 hours. The solution was filtrated and solvent was removed under vacuo to yield a crude product of Boc-Gly-Ser which was transferred to the next step without further purification.

Example 17. Preparation of Cholesterylmesylate (oMsChol)

Mesyl chloride (0.1 mol) was added to a mixture of cholesterol (0.1 mol) and triethylamine (0.1 mol) in methylene chloride (100 mL) placed in an ice-bath. The mixture was stirred for 1 hour and the resulting product was washed with saline and dried over sodium sulfate. The solution was filtered and solvent was removed under vacuo to yield the crude product (omsChol) which was directly used with Boc-Gly-Ser from Example 16.

Example 18. Preparation of Cholesterylglycinylserinate (Boc-Gly-Ser-Chol)

Potassium tert-butoxide (0.1 mol) was added into a tetrahydrofuran solution (100 mL) of Boc-Gly-Ser and Cholesterol mesylate (0.1 mol) from Example 17. The mixture was stirred for 6 hours at about 65° C. The resulting solution was washed with saline and methylene chloride layer was isolated, dried over sodium sulfate and solvent removed under vacuo to yield an intermediate product of Boc-gly-ser-chol and was used directly without further purification.

saturated sodium bicarbonate solution (~10%) and the organic layer was dried over sodium sulfate and solvent was removed under vacuo. The resulting intermediate of $NH_2$-Gly-Ser-Chol-$PEG_{17}$ was directly transferred to the the next step without further purification. $NH_2$-Gly-Ser-Chol-$PEG_{17}$ (0.1 mol) and dried lactobionic acid (0.1 mol) was mixed in methanol (100 mL) and the reaction was initiated by adding triethylamine (0.1 mol). The reaction was reflux in a water bath of 60-65° C. for 16 hours under constant stirring and solvent was removed under vacuo. The resulting waxy crude product was washed with hexanes and dried under vacuo to yield a pale to yellowish solid (85 to 95%) as showed in Chemical Structure 18.

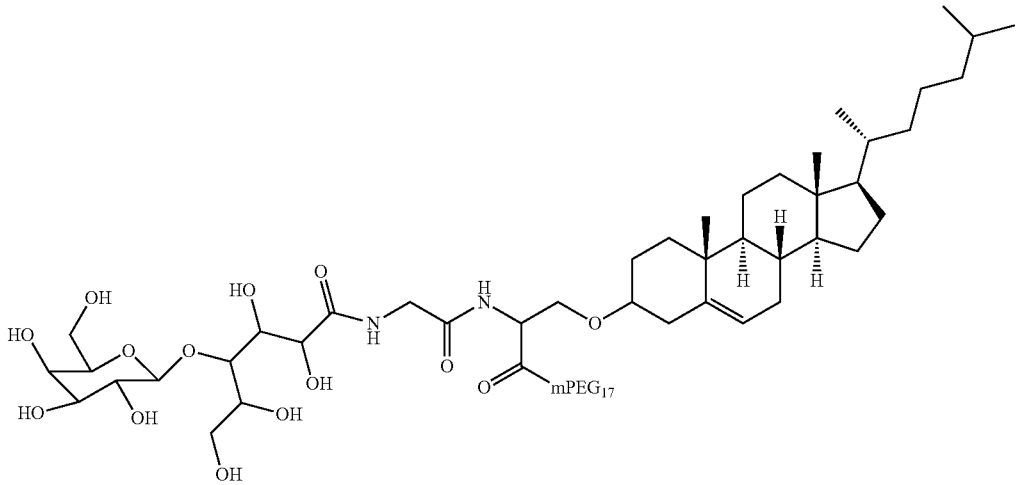

Chemical structure 18

Example 19. Preparation of PEG-cholesterylglycinylserinate (Boc-glyserchol-PEG)

Heptaetheylene glycol methyl ether (0.1 mol) and Boc-gly-ser-chol (0.1 mol) from the Example 18 was mixed with N,N'-Dicyclohexylcarbodiimide (0.1 mol) in tetrahydrofuran (100 mL). The mixture was kept at ambient room temperature under constant stirring for over night (about 16 hours) and the the reaction was checked for completion by TLC or HPLC. The solution was filtered and solvent was removed under reduced vacuo. The crude product was purified using a silica gel column with the eluent of hexanes/ethyl acetate (1:1, v/v). This intermediate product of Boc-glyserchol-$PEG_{17}$ was used for the final synthetic step.

Example 20. Preparation of $PEG_{17}$-cholesterylglycinylserinyllactonate

The intermediate product of Boc-Gly-Ser-Chol-$PEG_{17}$ (0.1 mol) from Example 19 was dissolved in methylene chloride (50 mL) and trifluoroacetic acid (1 mol) was added. The mixture was stirred for 2 hours to remove the amino-protecting group. The reaction was quenched by adding Example 21. Preparation of $N^\epsilon$-tert-butyloxycarbonyl(Boc)-lysine-cholesterol $N^\epsilon$-tert-butyloxycarbonyl(Boc)-lysine (0.2 mol) in 150 mL of methylene chloride was transferred to a round-bottomed flask equipped with a mechanical stirrer. Triethylamine (0.4 mol) is added to the flask and the reaction mixture is cooled down to 0 and 10° C. in an ice-water bath under constant stirring. Cholesteryl chloride (0.18 mol) in 100 mL of methylene chloride was added dropwise. The reaction mixture was allowed to continue under constant stirring for 2 hours after the addition of Cholesteryl chloride was completed. The solution was concentrated to give the crude product of $N^\epsilon$-tert-butyloxycarbonyl(Boc)-$N^\alpha$-cholesterol lysine (yield ~60%), which was used directly for the next step Example 22. Preparation of $N^\epsilon$-Boc-lysine-cholesterol-mPEG Equivalent amount of monomethoxyPEG was mixed with $N^\epsilon$-Boc-$N^\alpha$-cholesterol-lysine (from Example 21) in 200 mL THF/DCM (1/1. v/v) and the reaction was started with adding equal amounts of DCC as the catalyst at room temperature under constantly stirring for overnight. The completion of the reaction was monitored by TLC or HPLC. The solid was filtered out and the solution was concentrated under reduced pressure. The crude product was purified by column chromatography with silica gel (eluent: hexanes/ethyl acetate) with a yield of 50% or higher which was used directly for the next step.

Example 23. Preparation of $N^\varepsilon$-lysine-$N^\alpha$-cholesterol-mPEG

Trifluoroacetic acid (10 equivalents) was added to the DCM solution of $N^\varepsilon$-Boc-lysine-cholesterol-mPEG intermediate (from Example 22) and the mixture was stirred for 2 hours. The mixture was carefully quenched by adding sodium bicarbonate solution and the organic layer was dried over sodium sulfate and concentrated after removed the salt to quantitatively yield the intermediate $N^\varepsilon$-lysine-cholesterol-mPEG, which was used directly at the next step.

Example 24. Preparation $N^\varepsilon$-lactobionyl-$N^\alpha$-cholesterol-mPEG-lysinate Lactobionic acid was converted into intramolecular ester by removing water in toluene and mixed with equal molar quantity of $N^\varepsilon$-lysine-$N^\alpha$-cholesterol-mPEG reacted at room temperature in methanol to obtain $N^\varepsilon$-lactobionyl-$N^\alpha$-cholesterol-mPEG-lysinate (Chemical structure 19), The reaction mixture was loaded on a layer of silica gel and air dried. A silica gel column was prepared in a fit filter funnel to give a column volume of about 1 L. The predried reaction mixture was placed on the top of the column and the column was eluted with acetone/hexanes 200 mL of acetone/Isopropyl alcohol (⅕) and 500 mL of 100% acetone. The eluents containing compound was concentrated in vacuo to $N^\varepsilon$-tert-butyloxycarbonyl(Boc)-$N^\alpha$-cholesterol lysine (yield ~80%).

aminopentanol, aminohexanol. Some of these PEG-carbohydrate conjugates are shown in Table 8.

In another aspect, the polymer chain may be replaced by other polymer(s) such as polymethylene glycol or polypropylene glycol or a mixture of the repeating units of methylene glycol, ethylene glycol and propylene glycol. Hydrophilic polymers useful in forming the polymer-carbohydrate conjugates of the invention include polyethyleneglycol (PEG) and other polyalkene oxide polymers, polyoxyethylene alkyl ethers, polyvinylpyrrolidone, Poly(allylamine), Poly(1-glycerol methacrylate), Poly(2-ethyl-2-oxazoline), Poly(2-hydroxyethyl methacrylate/methacrylic acid)/poly(2-hydroxyethyl methacrylate), Poly(2-vinylpyridine), Poly(acrylamide/acrylic acid), Poly(acrylic acid), Poly(butadiene/maleic acid), Poly(ethyl acrylate/acrylic acid), Poly(ethylene oxide-b-propylene oxide), Poly(ethylene/acrylic acid), Poly(methacrylic acid), Poly(maleic acid), Poly(N-iso-propylacrylamide), Poly(N-vinylpyrrolidone/vinyl acetate), Poly(styrenesulfonic acid), Poly(styrenesulfonic acid/maleic acid), Poly(vinyl acetate), Poly(vinyl phosphoric acid), Poly(vinylamine), Polyacrylamide, Polyacrylic Acid, Polyaniline, Polyethylenimine, Pullulan, Polymethacrylamide. Copolymers and block copolymers based on the list above may also be used. The free polymers are water-soluble at room temperature, as well as non-toxic. They do not elicit an appreciable immunogenic response in mammals. Hydrophilic polymers with narrow molecular weight distributions are preferable. Because of already existing acceptance in the pharmaceutical business, PEG is the preferred hydrophilic polymer.

Example 25. Oral Solution Compositions

PEG-carbohydrate conjugates were pre-dissolved in ¼ of the total volume of water added to a vessel equipped with a Chemical structure 19

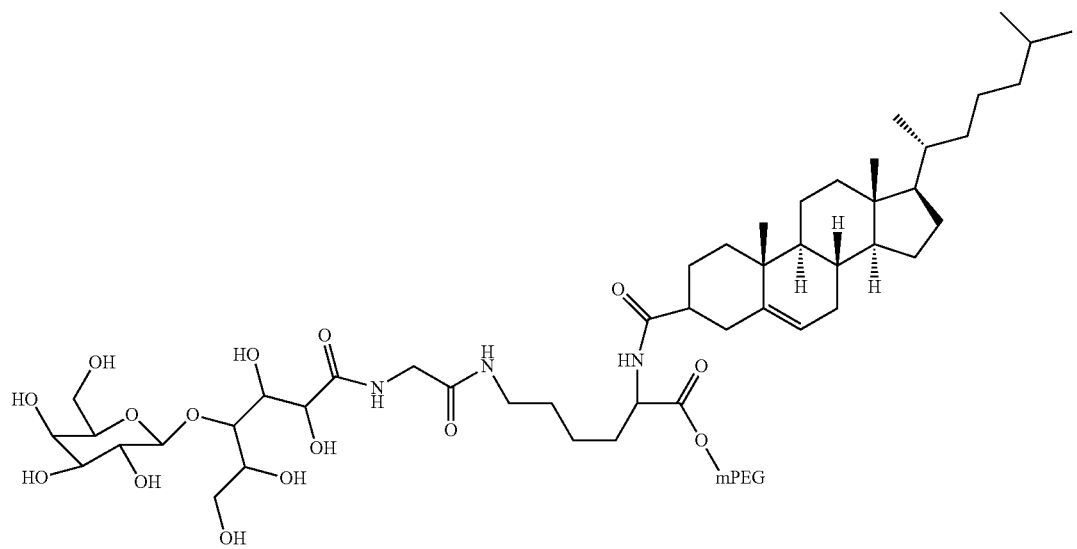

Similar synthetic methods from the Examples 1 to 24 may be utilized for the preparations of other PEG-carbohydrate conjugates; It also further demonstrated that selected molecules may be chemically extended and modified to provide said third or fourth available binding position or site, appropriate molecules include and not limited to aminoalcohols and diamines consisting of ethylenediamine, diaminopropane, ethanolamine, and aminopropanol, aminobutanol, mixer propeller. The drug substance was pre-dissolved in small amounts of diluted acid or base added then charged into the vessel with constant mixing. Mixing continued until the solution was visually homogeneous. Pre-dissolved excipients were slowly added to the vessel with adequate mixing. Mixing continued until fully a homogenous solution was achieved. A sample formulation is described in Table 7.

TABLE 7

| Ingredient | mg/mL |
| --- | --- |
| Drug Substance (active) | 30.0 |
| PEG-carbohydrate conjugates | 100 |
| Sodium Hydroxide | See below |
| Hydrochloric Acid | See below |
| Sodium Benzoate | 2.0 |
| Artificial Flavor | 5.0 |
| Purified Water | qs 1 mL |

The PEG-carbohydrate conjugates may be any of PEG-carbohydrate conjugates described in the invention with a PEG chain consisting of between about 10 and 45 subunits. Sodium hydroxide is used to prepare a 10% w/w solution in purified water. The targeted pH is in a range of 4.0 to 7.0. NaOH is used to adjust pH if necessary. The drug may be modafinil or nifedapine or esomeprazole or rapamycin or a fungicide or antitumor agent or another active agent.

Example 26. Injection Solution Compositions

All product contact equipment must be clean and sanitized. Pre-dissolved PEG-carbohydrate conjugate (at ¼ of the total volume) was added to a vessel equipped with a mixer propeller. The solid drug substance was pre-dissolved in a small amount of diluted acid or base (this step is eliminated for liquid drugs) and then charged to the vessel with constant mixing. Mixing continued until the solution was visually homogenous. Pre-dissolved excipients were slowly added to the vessel with adequate mixing. Mixing continued until fully a homogenous solution was achieved. Stainless steel cover for premix vessel to help maintain nitrogen overlay, at least two jacketed, pressurizable, stainless steel tanks equipped with agitation and capable of nitrogen overlay were needed. The mixture in the tank with a nitrogen overlay and agitation was held for 1 hour to reduce dissolved oxygen content in the product. The tank impeller mixing speed was approximately 45-50 RPM and compressed air supply pressure to the mixer was between 10-13 psig. Mixing rates may be adjusted as required to prevent foaming of product. Using aseptic technique, a 5 mL sample as taken for pH measurement. If necessary, 10% sodium hydroxide solution or 6N hydrochloric acid was used to adjust the pH of the product to 6.0-8.0. Filled the product in a sterile-filtered nitrogen environment into washed and sterilized 5-mL Type 1 glass vials and each vial was sealed with a sterilized 13-mm pharma grade rubber solution stopper and crimped with a sanitized 13-mm pharma grade flip-off aluminum seal. A final autoclave process could be used if necessary. A sample formulation is described in Table 8.

TABLE 8

| Ingredient | mg/mL |
| --- | --- |
| Drug Substance (Active) | 10.0 |
| PEG-carbohydrate conjugate | 30 |
| Sodium chloride | 9 |
| Sodium hydroxide (NaOH) | for pH adjustment |
| Hydrochloric acid (HCl) | for pH adjustment |
| Water for Injection | qs 1.0 mL |

The PEG-carbohydrate conjugate may be any of PEG-carbohydrate conjugates described in the invention with a PEG chain consisting of between about 10 and 45 subunits. Sodium hydroxide is used to prepare a 10% w/w solution in purified water. The targeted pH is in a range of 4.0 to 7.5. NaOH is used to adjust pH if necessary. The drug may be modafinil or nifedapine or esomeprazole or rapamycin or a fungicide or antitumor agent or anesthetic agent or another active agent.

Example 27. Topical Cream Composition

Pre-dissolved PEG-carbohydrate conjugate (at ¼ of the total volume) was added to a stainless steel vessel equipped with propeller type mixing blades. The drug substance was pre-dissolved in the mixture of organic acid, ethanol and glycerin then charged to the vessel with constant mixing. Mixing continued until the drug was visually dispersed in the conjugates at a temperature to 60°-65° C. Glycerin and ethyoxydiglycol were added with mixing. Finally Carbopol ETD 2020, ethanol, purified water and triethylamine were added with mixing. Mixing continued until fully a homogenous cream was achieved. The formulation is described in Table 9.

TABLE 9

| Ingredient | % |
| --- | --- |
| Drug Substance (Active) | 1.0 |
| PEG-carbohydrate conjugate | 10 |
| Carbopol ETD 2020 | 0.5 |
| Ethyoxydiglycol | 1.0 |
| Ethanol | 5.0 |
| Glycerin | 1.0 |
| Triethylamine | 0.20 |
| Organic acid | 3 |
| Sodium hydroxide | See below |
| Purified water | qs 100 |

The PEG-carbohydrate conjugate may be any of PEG-carbohydrate conjugates described in the invention with a PEG chain consisting of between about 10 and 45 subunits. Organic acid may be lactic acid or pyruvic acid or glycolic acid. Sodium hydroxide is used to adjust pH if necessary. The targeted pH range was between 3.5 and 7.0. The drug may be itraconazole, posaconazole, voriconazole or equaconazole, Terbinafine, Amorolfine, Naftifine, Butenafine, Benzoic acid, Sodium bicarbonate, Ciclopirox, Tolnaftate, Undecylenic acid, Flucytosine, Griseofulvin, Haloprogin, Fluocinolone acetonide or azithromycin.

Example 28. Topical Solution Composition

The topical solution was prepared as in Example 25; a sample formulation is described in Table 10.

TABLE 10

| Ingredient | % |
| --- | --- |
| Drug Substance (Active) | 1.0 |
| PEG-carbohydrate conjugates | 5.0 |
| α-Tocopherol | 0.5 |
| Organic acid | 3.0 |
| Ethanol | 5.0 |
| Sodium Benzoate | 0.2 |
| Sodium Hydroxide | See Below |
| Purified Water | qs 100 |

The PEG-carbohydrate may be any of PEG-carbohydrate conjugates described in the invention with a PEG chain consisting of between about 10 and 45 subunits. Organic acid may be lactic acid or pyruvic acid or glycolic acid. Sodium hydroxide is used to adjust pH if necessary. The targeted pH range was between 3.5 and 7.0. The drug may be itraconazole, posaconazole, voriconazole or equaconazole, Terbinafine, Amorolfine, Naftifine, Butenafine, Benzoic acid, Ciclopirox, Tolnaftate, Undecylenic acid, Flucytosine, Griseofulvin, Haloprogin, Sodium bicarbonate or Fluocinolone acetonide or azithromycin.

Example 29. Anti-Infective Ophthalmic Compositions

Pre-dissolved PEG-carbohydrate-sterol conjugate (at ¼ of the total volume) was added to a vessel equipped with a mixer propeller. The azithromycin drug substance was added with constant mixing. Mixing continued until the drug was visually dispersed in the solution. Pre-dissolved excipients and sterile purified water were slowly added to the vessel with adequate mixing. Mixing continued until fully a homogenous solution was achieved followed by sterile filtration and packaging. A sample formulation is described in Table 11.

TABLE 11

| Ingredient | mg/mL |
|---|---|
| Active | 15 |
| PEG-carbohydrate conjugate | 50 |
| Sodium Hydroxide | See below |
| Hydrochloric Acid | See below |
| Sodium Chloride | 9 |
| Purified water | qs 1 mL |

The PEG-carbohydrate may be any of PEG-carbohydrate-sterol conjugates described in the invention with a PEG chain consisting of between about 8 and 45 subunits. Sodium hydroxide is used to prepare a 10% w/w solution in purified water. The targeted pH is in a range of 6.5 to 7.8. Diluted NaOH or HCl may be used to adjust pH if necessary. The active may be azithromycin or itraconazole or posaconazole or voriconazole or another active agent.

Example 30. Preparation of Docetaxel Solution for Injection

A docetaxel solution suitable for intravenous delivery is prepared as follows. 4% (w/v) of CDL-mPEG$_{17}$ (see table 8) in Saline was added to a vessel equipped with a mixer propeller and 1.5% (w/v) of docetaxel was pre-dissolved in ethanol (1% of total volume, v/v) and charged into the vessel with constant mixing at ambient room temperature. Mixing was continued until the solution was visually homogeneous. Equal volume of Saline was added to the vessel with adequate mixing. Mixing continued for another 30 minutes or until a homogenous solution was achieved. A sample formulation is described in Table 12.

TABLE 12

| Ingredient | mg/mL |
|---|---|
| Docetaxel | 0.75 |
| Ethanol | 10.0 |
| CDL-mPEG$_{17}$ | 20.0 |
| Sodium Chloride | 9.0 |
| Sodium Hydroxide | See below |
| Hydrochloric Acid | See below |
| Purified Water | qs 1 mL |

The PEG-carbohydrate conjugate may be any of PEG-carbohydrate conjugates described in the invention with a PEG chain consisting of between about 10 and 45 subunits. Sodium hydroxide is used to prepare a 10% w/w solution in purified water. The targeted pH is in a range of 4.0 to 7.5. Diluted NaOH or HCl may be used to adjust pH if necessary.

Example 31. Pharmacokinetic Profile of Docetaxel Formulations

Groups of three male mice (B6D2F1), 4 weeks old and weights of 25 to 32 grams were used for the studies. Pharmacokinetics (PK) were performed on heparinized mouse plasma samples obtained typically at after the bolus IV injection at 5, 15, 45 min and 1, 2, 3, 6, 12 and 24 hours for Docetaxel. Samples were analyzed using a HPLC-MS method. To determine the level of the drug, the drug was first isolated from plasma with a sample pre-treatment. Acetonitrile were used to remove proteins in samples. An isocratic HPLC-MS/MS method was then used to separate the drugs from any potential interference. Drug levels were measured by MS detection with a multiple reaction monitoring (MRM) mode. PK data was analyzed using the WinNonlin program (ver. 6.3, Pharsight) noncompartmental models of analysis.

Figure 2:
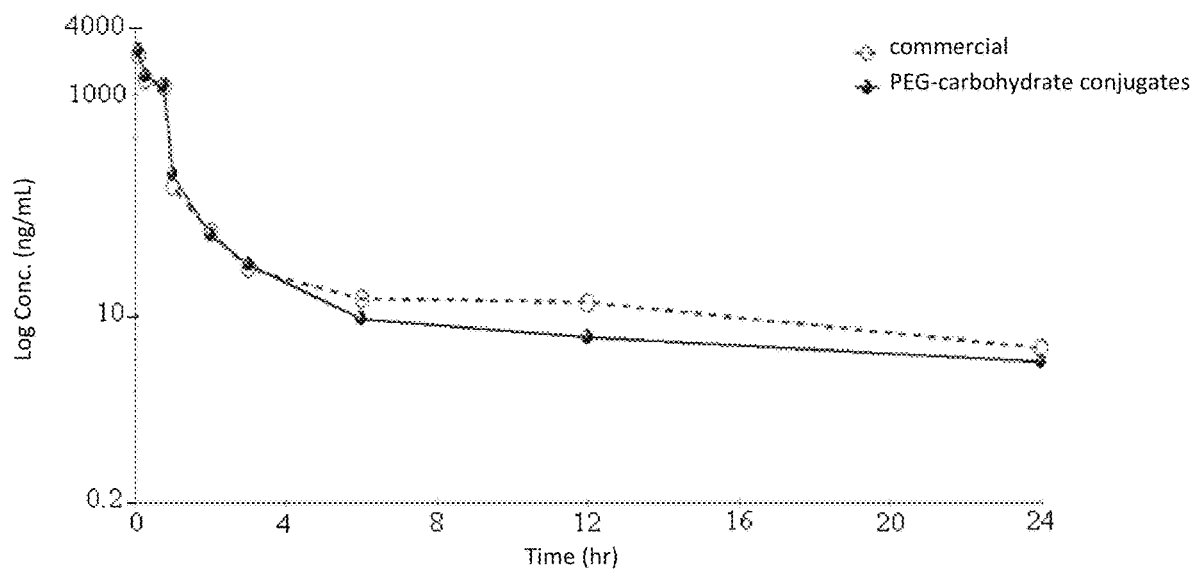
FIG. 2 shows pharmacokinetic profiles of Docetaxel formulations with (a) a commercial product and (b) Docetaxel solution consisting of 2% of a PEG-carbohydrate-sterol conjugate.

FIG. 2 shows mouse PK profiles of Docetaxel formulations with (a) 0.74 mg/mL Docetaxel in a a commercial product consisting of 2.5% Polysorbate 80 and 1.5% ethanol in saline) and (b) 0.74 mg/mL Docetaxel in a formulation consisting of 2% of CDL-mPEG$_{17}$ and 1% ethanol in saline solution. The drug was administered intravenously and the dosing strength was 10 mg/kg. From the non-compartmental calculations, the AUC were 1707.5 ng·min/mL with a half-life of 9.8 hours for the commercial docetaxel solution (a) and 1739.4 ng·min/mL with a half-life of 14.3 hours for the docetaxel in CDL-mPEG$_{17}$ solution (b), respectively.

Example 32. Preparation of Paclitaxel Solution for Injection

A paclitaxel solution suitable for intravenous delivery is prepared as follows. 6% (w/v) of CDL-mPEG$_{17}$ (see table 8) in Saline was added to a vessel equipped with a mixer propeller and 2.4% (w/v) of docetaxel was pre-dissolved in 1% NaOH-ethanol (1% of total volume, v/v) and charged into the vessel with constant mixing at ambient room temperature. Mixing was continued until the solution was visually homogeneous. Equal volume of Saline was added to the vessel with adequate mixing. Mixing continued for another 30 minutes or until a homogenous solution was achieved. A sample formulation is described in Table 13.

TABLE 13

| Ingredient | mg/mL |
|---|---|
| Paclitaxel | 12.0 |
| Ethanol | 10.0 |
| CDL-mPEG$_{17}$ | 20.0 |
| Sodium Chloride | 9.0 |
| Sodium Hydroxide | See below |
| Hydrochloric Acid | See below |
| Purified Water | qs 1 mL |

The PEG-carbohydrate may be any of PEG-carbohydrate conjugates described in the invention with a PEG chain consisting of between about 10 and 45 subunits. Sodium hydroxide is used to prepare a 10% w/w solution in purified water. The targeted pH is in a range of 4.0 to 7.5. Diluted NaOH or HCl may be used to adjust pH if necessary.

Example 33. Solubility of the PEG-Carbohydrate Conjugates

The water solubility of the PEG-carbohydrate conjugates may be estimated by the LogP calculations. The overall hydrophilic-lipophilic balance is dependant on the each of the carrier groups. The samples of the conjugates are listed in Table 14. While the solubility is increased with trisaccaride as the sugar carrier but the cost production is much higher, the solubility of the conjugates is lower with monsasscharide carrier. Thus a disaccharide is well balanced as a water solubility enhancer and most suitable from scale-up productions and economic considerations.

TABLE 14
| Conjugate | Structure | LogP |
|---|---|---|
| Cholesterypropane-diamineisomaltotriose-mPEG$_{11}$ monosaccharide unit: 3 | 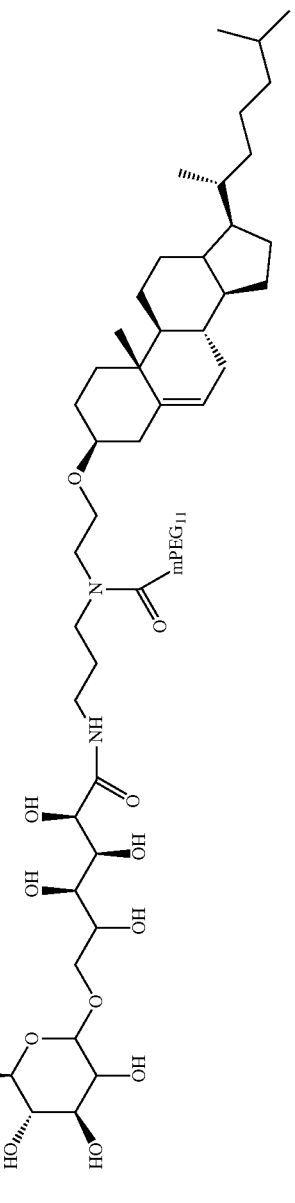 | −0.69 |
| Cholesterypropane-diaminelactobionate-mPEG$_{11}$ monosaccharide unit: 2 | 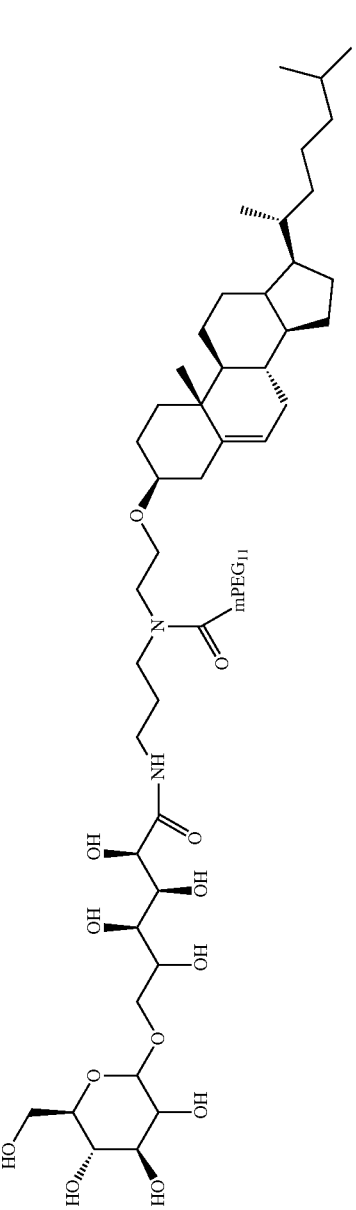 | 0.44 |

TABLE 14-continued
| Conjugate | Structure | LogP |
|---|---|---|
| Cholesteryltriethylene-tetraminelactobionate-di-mPEG$_{11}$ monosaccharide unit: 2 | 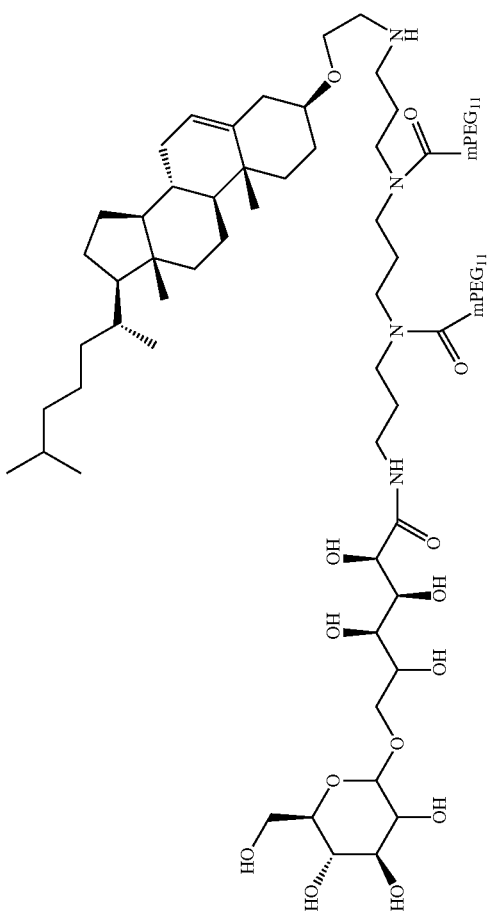 | −1.94 |
| Cholesterypropane-diaminelaminaribiose-mPEG$_{11}$ monosaccharide unit: 2 | 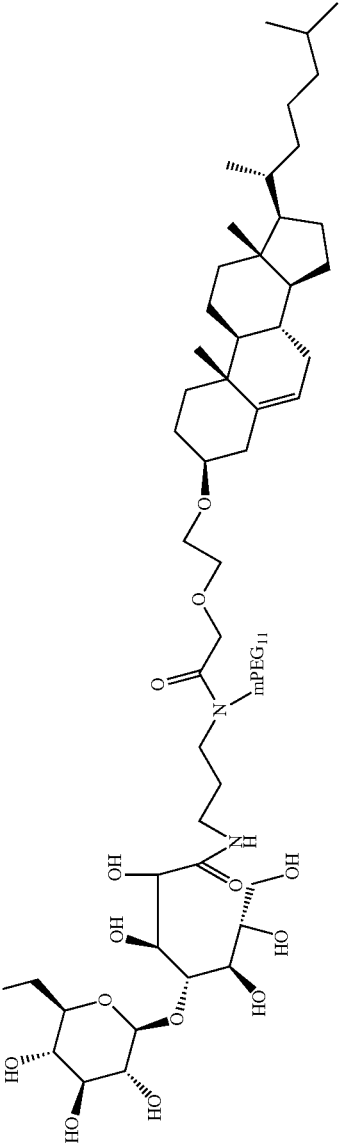 | 1.82 |

TABLE 14-continued

| Conjugate | Structure | LogP |
|---|---|---|
| Oleoylpropanediamine-lactobiona-temPEG$_{11}$ monosaccharide unit: 2 | 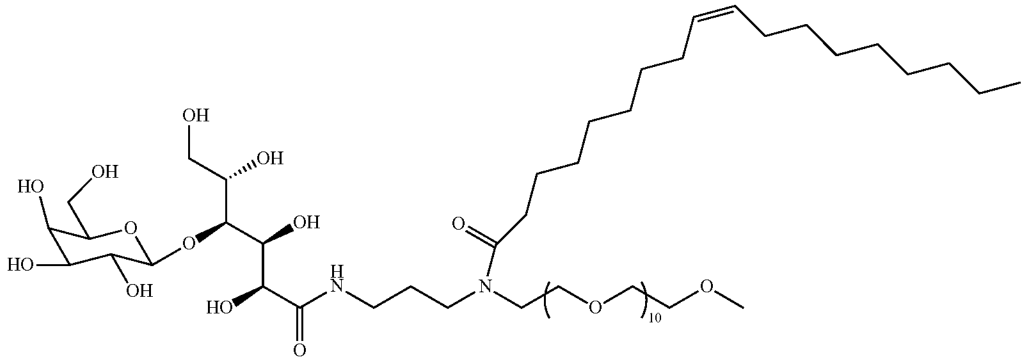 | −0.03 |
| Cholesterypropane-diaminegluconate-mPEG$_{11}$ monosaccharide unit: 1 | 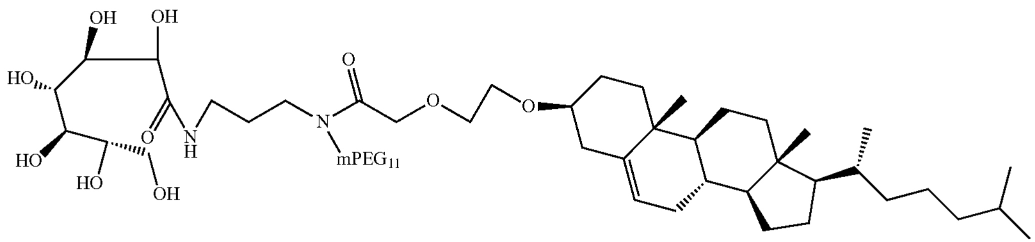 | 2.27 |
| Cholesterypropane-diamineascorbate-mPEG$_{11}$ monosaccharide unit: 1 | 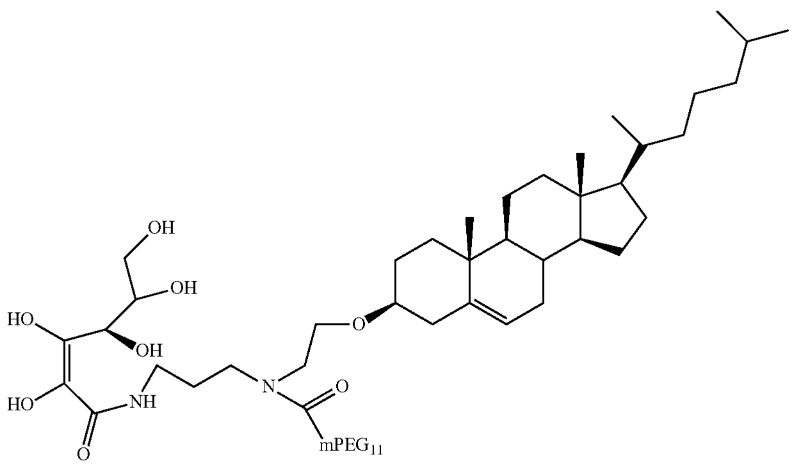 | 2.86 |

TABLE 14-continued
| Conjugate | Structure | LogP |
|---|---|---|
| Tocopherylpropane-diaminelactobionate-mPEG₁₁ monosaccharide unit: 2 | 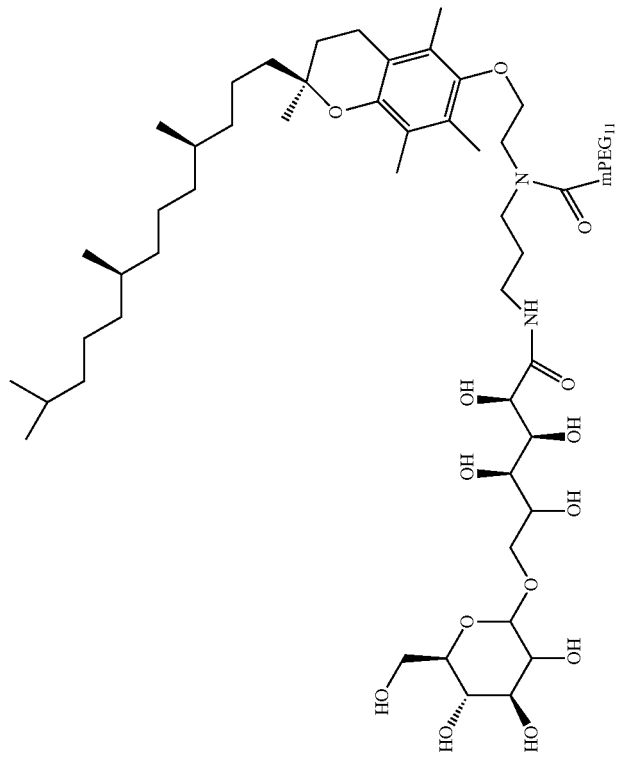 | 3.39 |

TABLE 14-continued
| Conjugate | Structure | LogP |
|---|---|---|
| Tocopherylpropane-diamineisomaltotriose-mPEG$_{11}$ monosaccharide unit: 3 | 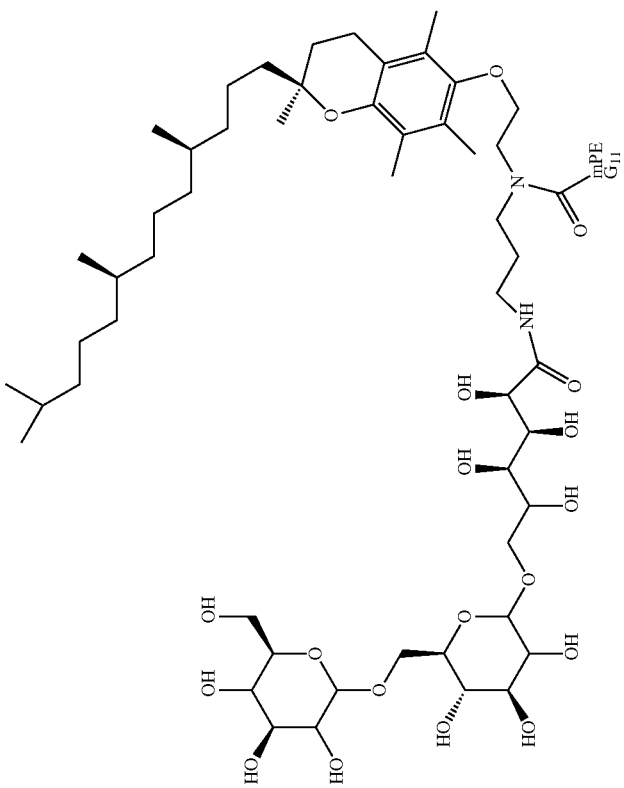 | 2.57 |
| Retinoylpropane-diaminelactobionate-mPEG$_{11}$ monosaccharide unit: 2 | 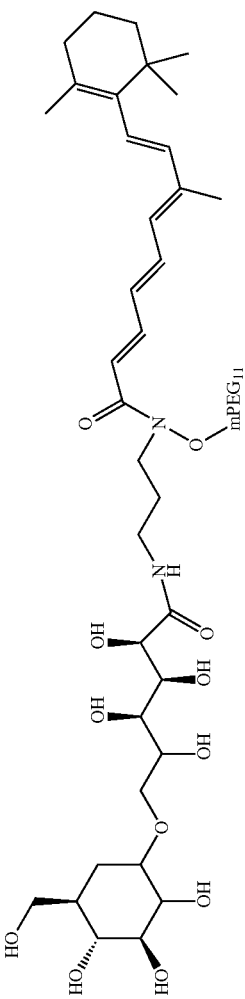 | −1.80 |

TABLE 14-continued
| Conjugate | Structure | LogP |
|---|---|---|
| Retinoyl diethylene-triamineisomaltotriose-mPEG$_{11}$ monosaccharide unit: 3 | 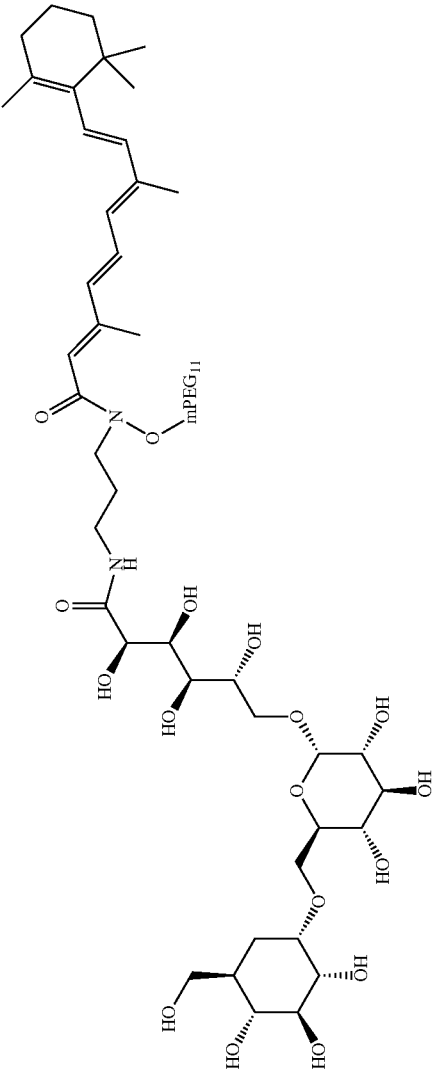 | -3.71 |
| Cholecalciferol-diethylene-triamineisomal-totriose-mPEG$_{11}$ monosaccharide unit: 3 | 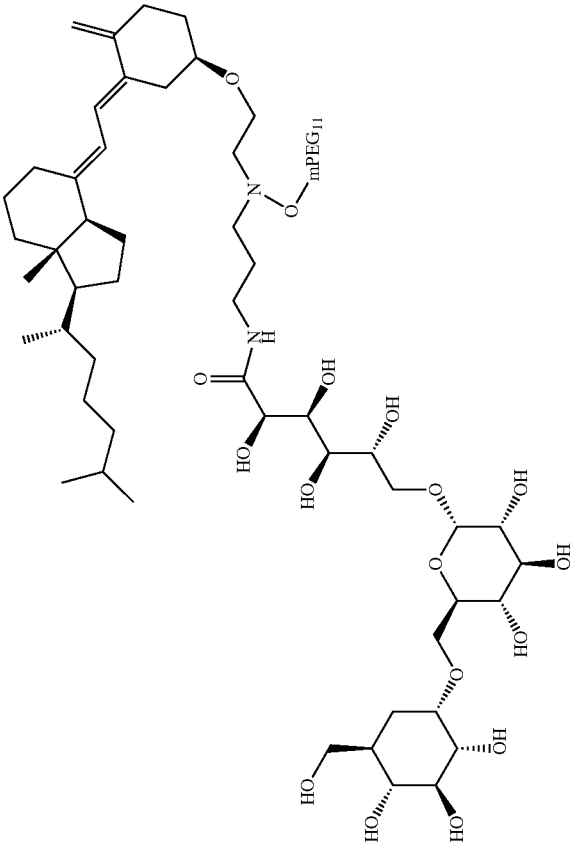 | -0.73 |

As demonstrated in Reach Schemes 1 to 9, monosaccharides, disaccharides included but not limited to sucrose, lactulose, galactose, lactose, galactose, maltose, trehalose, cellobiose, kojibiose, nigerose, isomaltose, trehalose, sophorose, laminaribiose, gentiobiose, turanose, maltulose, palatinose, gentiobiulose, mannobiose, melibiose, melibiulose, rutinose, rutinulose and xylobiose, trisaccharides included but limited to isomaltotriose, nigerotriose, maltotriose, melezitose, maltotriulose, raffinose and kestose, are all suitable to make a polymer-carbohydrate conjugate. Due to a weaker solubility enhancement of monosaccharides as showed in the Example 29 and significantly higher costs of production with trisaccharides, disacaharides such as lactobionic acid is most suitable for chemical development strategies, developing a robust synthetic route that yields appropriate physical/chemical properties and clinically suitable in drug formulations.

Example 34. Solubility Study of Propofol

1% (w/v) of propofol was prepared in a saline based solution with different PEG-carbohydrate conjugates. Table 15 listed the minimum concentration of the conjugates required to solubilize propofol as a solubility test reference. While tocopherylpropanediaminelactobionate-mPEG$_{11}$ demonstrated the lowest molar concentration for solubilizing propofol, much high conjugate concentration was required for cholesterypropanediaminegluconate-mPEG$_{11}$ and an emulsion was formed with stearylpropane-diamine-lactobionate-mPEG$_{11}$ regardless the lipid concentration.

TABLE 15

| Conjugate | Concentration (% w/v) |
|---|---|
| Cholesterypropanediaminegluconate-mPEG$_{11}$ | 5.3 |
| Cholesterypropanediamineascorbate-mPEG$_{11}$ | 4.6 |
| Cholesterypropanediaminelactobionate-mPEG$_{11}$ | 3.2 |
| Tocopherylpropanediaminelactobionate-mPEG$_{11}$ | 3.3 |
| Retinoyl propanediaminelactobionate-mPEG$_{11}$ | 2.9 |
| Cholecalciferol-diethylene-triamineisomaltotriose-mPEG$_{11}$ | 2.2 |
| Cholesterypropanediamineisomaltotriose-mPEG$_{11}$ | 2.0 |
| Cholesterytriethylenetetramine-lactobionate-bis-mPEG$_{11}$ | 1.6 |
| Stearylpropanediaminelactobionate-mPEG$_{11}$ | 3 to 10 (Emulsion) |

In another aspect, the invention comprises a method of solubilizing a water-insoluble agent, i.e., a drug compound that, because of low solubility in water, typically requires formulation with a pharmaceutically acceptable carrier for effective delivery to an intended site of action. Such delivery may be intravenous, oral, topical, subdermal, sublingual, or any other mode of drug delivery. The invention also includes compositions for such delivery. Both the methods and the compositions related to delivery of water-insoluble agents employ the PEG-carbohydrate conjugates of the present invention and the methods and materials described above.

Example 35. Solubility Study of Voriconazole

1% (w/v) of voricazole was prepared in a saline based solution with different PEG-carbohydrate conjugates. Table 16 listed the minimum concentrations of the conjugates required to solubilize voriconazole as a solubility test reference. While it demonstrated that the lowest polymer to drug concentration ratio was N,N,N-cholesterol-lactobionoyl-mPEG(12)-propanediamine for solubilizating voricanazole, much high concentration of N,N,N-oleoyl-lactobionoyl-mPEG(12)-propanediamine was required for the sample solution with the same voriconazole content. This is largely due to a relative stronger hydrophobic interactions of cholesterol to the solute than those of oleic acid. The example further demonstrated the significant difference between sterols (with a ring structure) and fatty acids (linear compounds) as the lipophilic carriers for solubilizating hydrophobic compounds, even though the conjugates with fatty acids have more negative values of LogP, and thus a small difference in HLB values may have a large impact in the solubilization of lipophilic compounds.

TABLE 16

| Polymer | LogP | HLB[1] | Solubilizing Voriconazole (min. polymer to drug ratio) |
|---|---|---|---|
| N,N,N-cholesterol-lactobionoyl-mPEG(19)propanediamine | −0.81 | 14.9 | 15 |
| N,N,N-cholesterol-lactobionoyl-mPEG(12)propanediamine | −0.44 | 15.0 | 10 |
| N,N,N-oleoyl-lactobionoyl-mPEG(12)propanediamine | −1.94 | 16.0 | 20 |

[1]Hydrophilic-lipophilic balance

Unlike nature occurring lipids such as phospholipids, the conjugates of the present invention do not have a critical micellar concentration (CMC). Micelles only form when the concentration of surfactant is greater than the CMC, and the temperature of the system is greater than the critical micelle temperature. The present polymer-carbohydrate-sterol conjugates may form aggregates spontaneously at any given concentration.

The present invention discloses a novel polymer-carbohydrate conjugate system having at least one of carbohydrate moiety that may be used as a safe and biocompatible vehicle for drug or molecule delivery. A therapeutic, diagnostic or cosmetic agent may be solubilized or encapsulated in those polymer-carbohydrate conjugates to form a solution or micro-suspension.

Generally, the invention includes compositions and methods for synthesizing polymer-carbohydrate conjugates comprising a glycerol backbone or a multiamine or amino acid with a polymer (PEG) chain, a sugar (carbohydrate) and a sterol or "fat soluble" vitamin or alike group bonded to the backbone. Spacer or linker groups including amino acids may be included between the backbone and the PEG chains, carbohydrates or lipophilic groups. Furthermore, the terminal end of PEG chain may be a charged or polar moiety. For example, in at least one aspect of the present disclosure, a chemical compound carrier for improving the biocompatibility of a therapeutic agent and for increasing the solubility of a hydrophobic or lipophilic agent in water is disclosed. The carrier may comprise a molecular structure represented by the formula:

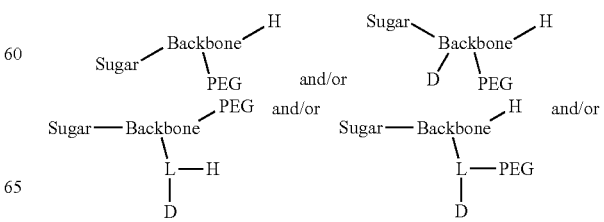

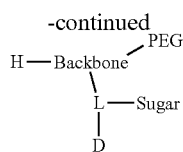

wherein: H is a lipophilic carrier void of steroid acids and fatty acids; Sugar is a carbohydrate comprises saccharide; PEG is a polymer of polyethylene glycols; D is a secondary sterol or lipophilic vitamin or PEG or carbohydrate; Backbone is a molecule having three or four available binding positions and being void of a drug moiety, said Backbone comprising at least one of glycerol, glycerol-like analogues, diamines, triamines, tetraamine, diaminoalcohol, aminoalcohols, aminodiol, aminotriols, amino acids, and polyamines; and L is a coupler comprising at least one of glycerol or glycerol-like analogues having three available binding positions, diamines, triamines, diaminoalcohol, aminoalcohols, aminodiols, aminotriols, and amino acids having three available binding positions.

The compounds of the present invention are effective to formulate compositions of active agents, such gemcitabin or platinum drugs, whereby side effects and toxicities associated with therapeutic treatments are reduced.

In the present invention, the permeation enhancement properties of PEG-carbohydrate conjugates may increase the in vivo targeted delivery of drugs, reduce toxicity and improve oral bioavailability of various drugs.

Solutions comprising conjugates of the present invention with solubilized active agents that may incorporate many active agents, including but not limited to propofol, cisplatin, docetaxel, voriconizole and alfaxalone.

One feature or aspect of an embodiment is believed at the time of the filing of this patent application to possibly reside broadly in a chemical compound or a method of making a compound represented by the formula:

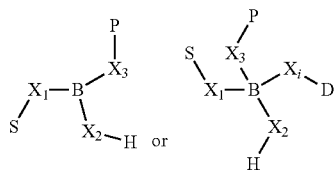

where $X_1$, $X_2$, $X_3$ and $X_4$ are representing a type of linking process of alkylation, etherification, esterification or amidation, B is a central backbone, H is sterol or a lipo-vitamin selected from the group including and not limited to cholesterol or sterols, carotenoids, cholecalciferol, retinoids and tocopherols, or alike molecule; S is a carbohydrate, P is a polymer and D is a duplication of H, S or P. In presence of cholesterol as the primary lipohilic carrier, the fourth carrier (D) may be a fatty acid or polyunsaturated alcohol or lipid molecule in additional to sterols or lipo-vitamins, preferably the fatty acid is consisting of 5 to 22 carbons. The order of conjugating position for each carrier is not restricted on the backbone. Wherein "B" comprises glycerol or glycerol-liking having three available binding positions or diamines, triamines, tetraamine and polyamines or diaminoalcohol or amino acids having three available binding positions and "H" comprises cholesterol or sterols having a single hydroxyl group or tocopherols or tocotrienols or cholecalciferol or retinols, retinals, and retinoic acid.

Another feature or aspect of an embodiment is demonstrated at the time of the filing of this patent application to possibly reside broadly in a chemical compound or a method of making a compound wherein a polymer-carbohydrate conjugate with defined carriers is made by a method comprising the steps of:
a. selecting a central backbone void drug moieties with at least three available sites for the conjugations between the three carriers and the central backbone;
b. selecting a polymer as the first career;
c. selecting a terminal group on the polymer carrier
d. selecting a sterol or lipophilic vitamin as the second carrier;
e. selecting a carbohydrate as the third carrier
f. selecting a polymer or sterol or lipophilic vitamin or carbohydrate as the fourth carrier
g. alternatively selecting a hydrophobic compound other than sterol or lipophilic vitamin as the fourth carrier;
h. selecting a linker or linkers for coupling reactions of alkylation including N-alkylation or O-alkylation or esterification or etherification or amidation between carriers and center backbones.

Yet another feature or aspect of an embodiment is demonstrated at the time of the filing of this patent application to possibly reside broadly in a chemical compound or a method of making a compound where the order of each conjugation step is not restricted and may further comprise the steps of alkylation, etherification, esterification or amidation:
a. protecting the hydroxyl or amino group;
b. bonding the first carrier to the central backbone;
c. bonding the second carrier to the central backbone;
d. removing the hydroxyl or amino protecting group; and
e. bonding the third carrier to the central protecting group.

Still another feature or aspect of an embodiment is demonstrated at the time of the filing of this patent application to possibly reside broadly in a chemical compound or a method of making a compound wherein suitable molecules may be used as the backbone including glycerol or glycerol-like analogues or multiamines or amino acids or triols or diols with a carboxy group or amine or diamines with a hydroxyl or carboxy group and extensible amines or alcohols, wherein the hydrophobic carrier is a sterol or lipophilic vitamin.

Another feature or aspect of an embodiment is demonstrated at the time of the filing of this patent application to possibly reside broadly in a chemical compound or a method of making a compound wherein the polymer is a PEG having subunits between 5 and 45. The PEG chain may consist of between about 3 and 45 subunits. More preferably the PEG chain consists of between about 5 and 25 subunits. Still more preferably the PEG chain consists of between about 8 and 25 subunits.

Yet another feature or aspect of an embodiment is demonstrated at the time of the filing of this patent application to possibly reside broadly in a chemical compound or a method of making a compound where the polymer is a branched PEG having 2 or more subchains each chain having PEG subunits between 5 and 45.

Still another feature or aspect of an embodiment is demonstrated at the time of the filing of this patent application to possibly reside broadly a chemical compound or a method of making a compound wherein the PEG-carbohydrate conjugate is a compound represented by the formulas of the General Structure 1 trough 15.

A further feature or aspect of an embodiment is demonstrated at the time of the filing of this patent application to possibly reside broadly in a chemical compound or a method of making a compound having a acyclic carrier group wherein the hydrophobic group is selected from sterols including cholesterol, stigmasterol, ergosterol, hopanoids, phytosterol, sitosterol, campesterol, brassicasterol, avenasterol adosterol) excluding steroid acids, stanols (saturated steroid alcohols or hydrogenated sterols) or lipophilic vitamins: Vitamin E including and not limited to tocopherols and tocotrienols, Vitamin D including and not limited to cholecalciferol and ergocalciferol, and Vitamin A including and not limited to retinoids, retinol, retinal, retinoic acid, and carotenoids, Another feature or aspect of an embodiment is demonstrated at the time of the filing of this patent application to possibly reside broadly in a chemical compound or a method of making a compound having nonsterol or nonvitamins as the fourth carrier group wherein the hydrophobic groups may be selected from saturated fatty acids and unsaturated fatty acids or xanthophylls, astaxanthin, auroxanthin, capsanthin, capsorubin, chrysanthemaxanthin, crocetin, crocin, cryptoxanthin, fucoxanthin, kryptoxanthin, lutein, neoxanthin, rubixanthin, violaxanthin, zeaxanthin and polyunsaturated fatty acids as listed in Table 5 or polyunsaturated fatty alcohols including native polyunsaturated alcohols such as farnesol, solanesol and dodecaprenol. It is preferable to have the cholesterol as the primary lipophilic carrier which may reduce or suppress the hemolytic activity of a fatty acid.

Further feature or aspect of an embodiment is demonstrated at the time of the filing of this patent application to possibly reside broadly in a chemical compound or a method of making a compound wherein the sugar is a carbohydrate including monosaccharides or disaccharides or oligosaccharides selected from Table 4 and their analogues or derivatives are including but not limited to ascorbic acid, sugar acids, amino sugars including but not limited to ascorbic acid, gluconic acid, glucaric acid, glucuronic acid, galacturonic acid, steviol glycoside (Rebaudioside A), sucralose, lactitol, maltitol, isomalt, maltotriitol, maltotetraitol, mogrosides, glycyrrhizin, inulin and osladin.

Yet another feature or aspect of an embodiment is demonstrated at the time of the filing of this patent application to possibly reside broadly in a chemical compound or a method of making a compound wherein the linker is selected from the group consisting of —S—, —O—, —N—, —OCOO—, and the linkers in Tables 2 and 3 to form covalent bonds of ester or ether or amide between carriers and center backbones. While a conjugation reaction of alkylation or etherification or esterification or amidation is preferable with or without adding linker group, the carriers or center backbones may be chemically modified prior to the final coupling reactions. Those of chemical modifications may be carried out with one or more of the linker groups.

Another feature or aspect of an embodiment is demonstrated at the time of the filing of this patent application to possibly reside broadly in a chemical compound or a method of making a compound wherein preferable amino acid linkers are proline, glycine, alanine, lysine, cysteine, valine, isoleucine, leucine, methionine, phenylalanine, histidine, tryptophan, tyrosine, selenocysteine, and arginine.

Another feature or aspect of an embodiment is demonstrated at the time of the filing of this patent application to possibly reside broadly in a chemical compound or a method of making a compound wherein the PEG chain is perfectible monodisperse for intravenous administration of pharmaceutical agents and the monodisperse PEG chain may contain a few numbers of oligomers. The preferable number of oligomers is 1 to 10, more preferable is 3 to 10.

Yet another feature or aspect of an embodiment is demonstrated at the time of the filing of this patent application to possibly reside broadly in a chemical compound or a method of making a compound wherein the PEG chain is perfectible monodisperse for intravenous administration of pharmaceutical agents and the monodisperse PEG chain ranging from 65% to 150% of averaged (or targeted) molecular weights.

Yet another feature or aspect of an embodiment is demonstrated at the time of the filing of this patent application to possibly reside broadly in a chemical compound or a method of making a compound wherein the PEG chains are replaced by polymers selected from the group consisting of polymethylene glycol, polypropylene glycol, and copolymers comprised of a at least two of the monomers selected from the group consisting of methylene glycol, ethylene glycol and propylene glycol.

Still another feature or aspect of an embodiment is demonstrated at the time of the filing of this patent application to possibly reside broadly in a chemical compound or a method of making a compound wherein the terminal (R) group is preferably easily polarized or negatively or positively charged head-groups such as alkoxy moieties, amines, amino acids, and oligosaccharides.

A further feature or aspect of an embodiment is demonstrated at the time of the filing of this patent application to possibly reside broadly in a chemical compound or a method of making a compound wherein the composition for delivery of an active agent, comprising: a chemical compound is represented by the formula:

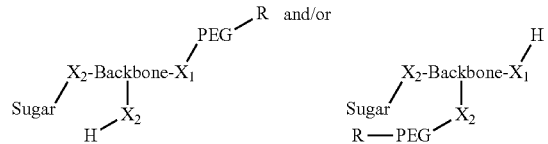

where $X_1$, $X_2$ and $X_3$ are representing a type of linking process of N-alkylation, esterification or etherification or amidation; and the active agent is a poorly water soluble compound of Biopharmaceutics classification II or IV including but not limited to alfaxalone, propofol, docetaxel, paclitaxel, voriconazole and posaconazole.

Another feature or aspect of an embodiment is demonstrated at the time of the filing of this patent application to possibly reside broadly in a method of delivering a compound, the method comprising preparing a polymer-carbohydrate conjugate(s) based formulation of the compound, where the formulation comprises a PEG-carbohydrate conjugate having the three carrier groups and the active agent is an antiviral or antitumor compound including but not limited to gentamicin, platiniums, efavirenz, darunavir and emtricitabine.

Still another feature or aspect of an embodiment is demonstrated at the time of the filing of this patent application to possibly reside broadly in a method of delivering a compound, the method comprising preparing a polymer-carbohydrate conjugate(s) in which the chemical compound may be synthesized from Backbones having two accessible binding positions or sites and selected from the group consisting of aminoalcohols, diamines, ethylenediamine, diaminopropane, ethanolamine, aminopropanol, aminobutanol, aminopentanol, amino-1-hexanol, the central backbone may be chemically extended and modified to provide said third or a fourth available binding position or site, i.e., a similar coupling procedure as showed in the General Structure 17.

Yet another feature or aspect of an embodiment is demonstrated at the time of the filing of this patent application to possibly reside broadly in a method of preparing a pharmaceutical formulation of a therapeutic agent, the method comprising:
a. determining a therapeutic target;
b. determining a mode of administration;
c. determining the physiological conditions the PEG-carbohydrate conjugates based formulation will encounter in reaching the therapeutic target using the mode of administration; and selecting a PEG-carbohydrate conjugate having one or more linkers between the three carriers including one or two PEG chains, one or two carbohydrates and one or two hydrophobic carriers (at least one sterol or lipophilic vitamin) and a central backbone, where such selecting is informed by the physiological conditions; and combining the PEG-carbohydrate conjugates and the therapeutic agent in a pharmaceutical formulation.

Another feature or aspect of an embodiment is demonstrated at the time of the filing of this patent application to possibly reside broadly in a chemical compound or a method of making a compound wherein the therapeutic agent is agent is an anesthetic or CNS (central nervous system) agent; and where the weight ratio of the PEG-carbohydrate conjugate to the drug compound is between about 1 and about 20.

Yet another feature or aspect of an embodiment is demonstrated at the time of the filing of this patent application to possibly reside broadly in a chemical compound or a method of making a compound wherein the therapeutic agent is a fungicide or immunosuppressant or antitumor agent or anesthetic agent; and where the weight ratio of the PEG-carbohydrate conjugate to the drug compound is between about 1 and about 30.

Another feature or aspect of an embodiment is to differentiate the present invention chemically and physically from the previous patent publications US2012/202,979 and US2012/202,890; in the present invention, a sterol with sole hydroxyl group excluding water soluble steroid acids is incorporated. As demonstrated in Tables 1, 15 and 16, such structures increased lipophilic properties was not mentioned or utilized in the previous inventions. For instance, the PEG-carbohydrate-cholesterol conjugates and PEG-carbohydrate-lipo-vitamin conjugates were demonstrated for the first time.

While preferred embodiments of the present invention have been described, those skilled in the art will recognize that other and further changes and modifications may be made without departing from the spirit of the invention, and all such changes and modifications should be understood to fall within the scope of the invention.

The invention claimed is:
1. A composition comprising a hydrophobic or a lipophilic therapeutic agent and chemical compound of formula (I):

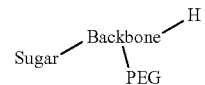

wherein:
Backbone is a molecule having at least three available binding positions or sites to which a lipophilic carrier, a carbohydrate carrier, and a polymer carrier are bound, respectively, said Backbone is selected from the group consisting of glycerol, diamines, triamines, tetraamines, diaminoalcohols, aminoalcohols, amino acids having three available binding positions; provided that Backbone is not a drug moiety;
H is the lipophilic carrier bound to Backbone, and H is selected from the group consisting of sterols, cholecalciferol, ergocalciferol, retinoids, carotenoids, tocopherols, cholesterol and tocotrienols; provided that H is not a steroidal acid or a fatty acid
Sugar is the carbohydrate carrier bound to Backbone, and Sugar is selected from the group consisting of a disaccharide sugar acid; and
PEG is the polymer carrier bound to Backbone, and PEG is a polyethylene glycol polymer having between 5 and 45 subunits and a terminal group (R) comprising methoxy.
2. The composition of claim 1, wherein said at least three available binding positions or sites of the chemical compound are an amino, hydroxyl, or carboxylic group.
3. The chemical compound of claim 1, wherein sterol is selected from the group consisting of cholesterol, stigmasterol, ergosterol, phytosterol, sitosterol, campesterol, brassicasterol, avenasterol, adosterol, and stanols; or wherein H is a retinoid selected from the group consisting of retinals, retinoic acid, and tretinoin.

* * * * *